(12) United States Patent
Cheng et al.

(10) Patent No.: US 7,816,353 B2
(45) Date of Patent: Oct. 19, 2010

(54) P70S6 KINASE MODULATORS AND METHOD OF USE

(75) Inventors: Wei Cheng, Edison, NJ (US); Erick Wang Co, San Diego, CA (US); Moon Hwan Kim, Palo Alto, CA (US); Rhett Ronald Klein, Chicago, IL (US); Donna T. Le, San Jose, CA (US); Amy Lew Tsuhako, Milpitas, CA (US); John M. Nuss, Danville, CA (US); Wei Xu, Danville, CA (US)

(73) Assignee: Exelixis, Inc., South San Francisco, CA (US)

( * ) Notice: Subject to any disclaimer, the term of this patent is extended or adjusted under 35 U.S.C. 154(b) by 470 days.

(21) Appl. No.: 10/576,653

(22) PCT Filed: Oct. 22, 2004

(86) PCT No.: PCT/US2004/035470

§ 371 (c)(1),
(2), (4) Date: Nov. 16, 2006

(87) PCT Pub. No.: WO2005/039506

PCT Pub. Date: May 6, 2005

(65) Prior Publication Data

US 2007/0208020 A1    Sep. 6, 2007

Related U.S. Application Data

(60) Provisional application No. 60/514,432, filed on Oct. 24, 2003, provisional application No. 60/551,429, filed on Mar. 8, 2004.

(51) Int. Cl.
| | | |
|---|---|---|
| C07D 239/38 | (2006.01) | |
| C07D 413/04 | (2006.01) | |
| C07D 413/12 | (2006.01) | |
| C07D 403/12 | (2006.01) | |
| A61K 31/505 | (2006.01) | |
| A61K 31/5355 | (2006.01) | |
| A61K 31/506 | (2006.01) | |
| A61K 31/496 | (2006.01) | |
| A61K 31/501 | (2006.01) | |
| C07D 211/88 | (2006.01) | |
| C07D 251/38 | (2006.01) | |
| C07D 487/04 | (2006.01) | |
| C07D 491/048 | (2006.01) | |
| A61K 31/44 | (2006.01) | |
| A61K 31/53 | (2006.01) | |
| A61K 31/519 | (2006.01) | |
| A61K 31/4355 | (2006.01) | |

(52) U.S. Cl. ............... 514/235.8; 514/272; 514/252.14; 514/344; 514/245; 514/262.1; 514/302; 544/321; 544/122; 544/238; 544/295; 544/262; 546/288; 546/115

(58) Field of Classification Search ............... 514/256, 514/269, 272, 274, 275, 235.8, 252.14; 544/297, 544/298, 309, 322, 323, 334, 335, 321, 122, 544/238, 295
See application file for complete search history.

(56) References Cited

U.S. PATENT DOCUMENTS

| | | | | |
|---|---|---|---|---|
| 2,354,505 | A * | 7/1944 | D Alelio et al. | 544/317 |
| 3,470,183 | A * | 9/1969 | Roth | 544/278 |
| 3,670,077 | A * | 6/1972 | Freeman et al. | 514/86 |
| 5,017,701 | A * | 5/1991 | Grinter et al. | 544/276 |
| 5,502,187 | A * | 3/1996 | Ayer et al. | 544/117 |
| 5,837,708 | A * | 11/1998 | Breu et al. | 514/274 |
| 5,939,462 | A * | 8/1999 | Connell et al. | 514/665 |
| 6,031,072 | A * | 2/2000 | Blaschuk et al. | 530/317 |
| 6,107,297 | A * | 8/2000 | Kindon et al. | 514/252.02 |
| 6,107,301 | A * | 8/2000 | Aldrich et al. | 514/261.1 |
| 6,303,618 | B1 * | 10/2001 | Griffin et al. | 514/45 |
| 6,849,631 | B2 * | 2/2005 | Carini | 514/253.01 |
| 7,176,310 | B1 * | 2/2007 | Baughman et al. | 544/253 |
| 2003/0053366 | A1 | 3/2003 | Lee | |
| 2003/0204083 | A1 * | 10/2003 | Giencke et al. | 544/211 |
| 2007/0155739 | A1 * | 7/2007 | Sucholeiki et al. | 514/230.5 |
| 2007/0249578 | A1 * | 10/2007 | Inghardt et al. | 514/210.18 |

FOREIGN PATENT DOCUMENTS

| | | | |
|---|---|---|---|
| DE | 2547691 | * | 4/1976 |
| GB | 635582 | * | 4/1950 |
| GB | 763041 | * | 12/1956 |
| JP | 51052184 | * | 5/1976 |
| JP | 63122684 | * | 5/1988 |

(Continued)

OTHER PUBLICATIONS

Font, et al., Journal of Combinatorial Chemistry (2003), 5(3), 311-321.-HAVE.*

(Continued)

*Primary Examiner*—James O Wilson
*Assistant Examiner*—Cecilia M Jaisle
(74) *Attorney, Agent, or Firm*—McDonnell Boehnen Hulbert & Berghoff LLP

(57) ABSTRACT

Compounds of formula III:

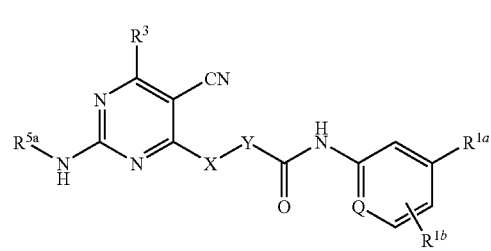

wherein $R^{5a}$, $R^3$, X, Y, Q, $R^{1a}$ and $R^{1b}$ are as defined in the specification, pharmaceutically acceptable salts thereof, and methods of use thereof.

11 Claims, No Drawings

FOREIGN PATENT DOCUMENTS

| | | | |
|---|---|---|---|
| JP | 2001139472 | * | 5/2001 |
| JP | 2002037787 | * | 2/2002 |
| JP | 2003221337 | * | 8/2003 |
| WO | WO 9724122 | * | 7/1997 |
| WO | WO 9809960 | * | 3/1998 |
| WO | WO 9835944 | * | 9/1998 |
| WO | WO 9843968 | * | 10/1998 |
| WO | WO 0020393 | * | 4/2000 |
| WO | WO 0192264 A1 | * | 12/2001 |
| WO | WO 03048164 | * | 6/2003 |
| WO | WO 03048165 | * | 6/2003 |
| WO | WO 2005030734 | * | 4/2005 |
| WO | WO 2005033072 | * | 4/2005 |

OTHER PUBLICATIONS

Baraldi, et al., Bioorganic & Medicinal Chemistry (2003), 11(19), 4161-4169.-HAVE.*
Sasaki, et al., Bioorganic & Medicinal Chemistry Letters (2002), 12(16), 2073-2077.-HAVE.*
El-Tombary, et al., Farmaco (1999), 54(7), 486-495-HAVE.*
Hardy, et al., Experimental Parasitology (1997), 87(3), 157-169.-have.*
Jantova, et al., Folia Biologica (Prague) (1997), 43(2), 83-89.*
Abd El-Fattah, Indian Journal of Heterocyclic Chemistry (1995), 4(3), 199-202.*
Ismail, Journal of the Serbian Chemical Society (1994), 59(6), 353-8.*
Spirkova, et al., Collection of Czechoslovak Chemical Communications (1994), 59(1), 222-6.*
Cocco, et al., Journal of Heterocyclic Chemistry (1992), 29(5), 1341-7.*
Temple, et al., Journal of Medicinal Chemistry (1992), 35(26), 4809-12.*
Ogawa, et al., Chemical & Pharmaceutical Bulletin (1992), 40(5), 1315-17.*
Seada, et al., Asian Journal of Chemistry (1992), 4(3), 604-14.*
Ogawa, et al., Chemical & Pharmaceutical Bulletin (1992), 40(2), 343-50.*
Harnden, et al., Australian Journal of Chemistry (1990), 43(1), 55-62.*
Youssef, Egyptian Journal of Pharmaceutical Sciences (1989), 30(1-4), 465-72.*
Hurst, et al., Australian Journal of Chemistry (1988), 41(8), 1209-19.*
Bailey, et al., Biochemistry (1989), 28(2), 494-504.*
Sharanin, et al., Khimiya Geterotsiklicheskikh Soedinenii (1987), (10), 1377-84.*
Nohara, et al., Tetrahedron Letters (1987), 28(12), 1287-90.*
Dunaev, et al., Khimiko-Farmatsevticheskii Zhurnal (1986), 20(10), 1198-202.*
Nair, et al., Journal of Organic Chemistry (1981), 46(16), 3354-7.*
Vasilev, et al., Doklady Bolgarskoi Akademii Nauk (1980), 33(6), 849-51.*
Roth, et al., Journal of Organic Chemistry (1980), 45(18), 3651-7.*
Walsh, et al., Journal of Chemical Research, Synopses (1980), (2), 38-9.*
Vorbrueggen, et al., Angewandte Chemie (1976), 88(21), 724-5.*
Pfleiderer, et al., Chemische Berichte (1971), 104(7), 2293-2312.*
Roth, Journal of Medicinal Chemistry (1969), 12(2), 227-32.*
Pfleiderer, et al., Chemische Berichte (1966), 99(9), 3008-21.*
Polya, et al., Journal of the Chemical Society, (Dec. 1964), 4986-92.*
Noell, et al., Journal of Medicinal & Pharmaceutical Chemistry (1962), 5, 1074-85.*
Davis, et al., Journal of the American Chemical Society (1960), 82, 2633-40.*
Bell, et al., Journal of the American Chemical Society (1960), 82, 1469-71.*
Boon, et al., Journal of the Chemical Society (1957) 2146-58.*
Kilroe Smith, et al., Tetrahedron (1957), 1, 38-44.*
Boon, et al., Journal of the Chemical Society (1951) 591-6.*
Wikipedia, Sirolimus, updated Feb. 28, 2009, <http://en.wikipedia.org/wiki/Sirolimus>, downloaded Mar. 19, 2009.*
Sawyers, et al., Nature Reviews—Cancer, Mar. 2008, vol. 8.*
Gomez-Cambronero, et al., J. Immunology, 2003, 6846-6855.*
Buset, et al., Canc. Res. 46, 5426-5430, Oct. 1986.*
Eidelberg, et al., Brain (1997), 120, 1315-1324.*
Mackie, et al., J. Clinical Endocrinology & Metabolism 91(7):2665-2671, 2006.*
McDermott, et al., Brit. J. Surgery, vol. 77, #10, 1179-1182, 2005.*

* cited by examiner

P70S6 KINASE MODULATORS AND METHOD OF USE

CROSS-REFERENCE TO RELATED APPLICATIONS

This application claims priority to U.S. provisional patent application 60/514,432 filed on Oct. 24, 2003, entitled "p70S6 Kinase Modulators and Method of Use," and 60/551,429 filed on Mar. 8, 2004, entitled "p70S6 Kinase Modulators and Methods of Use"; which is hereby incorporated by reference in its entirety for all purposes.

BACKGROUND OF THE INVENTION

1. Field of the Invention

This invention relates to compound for modulating protein kinase enzymatic activity for modulating cellular activities such as proliferation, differentiation, programmed cell death, migration, chemoinvasion and metabolism. Even more specifically, the invention relates to compounds which inhibit, regulate and/or modulate kinase receptor signal transduction pathways related to the changes in cellular activities as mentioned above, compositions which contain these compounds, and methods of using them to treat kinase-dependent diseases and conditions.

2. Summary of Related Art

Improvements in the specificity of agents used to treat cancer is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms.

Protein kinases are enzymes that catalyze the phosphorylation of proteins at the hydroxy groups of tyrosine, serine and threonine residues of proteins. The kinase complement of the human genome contains 518 putative protein kinase genes [Manning et al., Science, (2002), 298, 1912]. The consequences of this activity include effects on cell differentiation, proliferation, transcription, translation, metabolism, cell cycle progression, apoptosis, metabolism cytoskeletal rearrangement and movement; i.e., protein kinases mediate the majority of signal transduction in eukaryotic cells. Furthermore, abnormal protein kinase activity has been related to a host of disorders, ranging from relatively non-life threatening diseases such as psoriasis to cancer. Chromosomal mapping has revealed that over 200 kinases map to disease loci, including cancer, inflammatory and metabolic disease.

Tyrosine kinases can be categorized as receptor type or non-receptor type. Receptor-type tyrosine kinases have an extracellular, a transmembrane, and an intracellular portion, while non-receptor type tyrosine kinases are wholly intracellular.

Receptor-type tyrosine kinases are comprised of a large number of transmembrane receptors with diverse biological activity. In fact, about 20 different subfamilies of receptor-type tyrosine kinases have been identified. One tyrosine kinase subfamily, designated the HER subfamily, is comprised of EGFR (HER1), HER2, HER3, and HER4. Ligands of this subfamily of receptors identified so far include epithelial growth factor, TGF-alpha, amphiregulin, HB-EGF, betacellulin and heregulin. Another subfamily of these receptor-type tyrosine kinases is the insulin subfamily, which includes INS-R, IGF-IR, and IR-R. The PDGF subfamily includes the PDGF-alpha and -beta receptors, CSFIR, c-kit and FLK-II. Then there is the FLK family, which is comprised of the kinase insert domain receptor (KDR), fetal liver kinase-1 (FLK-1), fetal liver kinase-4 (FLK-4) and the fms-like tyrosine kinase-1 (Flt-1). The PDGF and FLK families are usually considered together due to the similarities of the two groups. For a detailed discussion of the receptor-type tyrosine kinases, see Plowman et al., DN&P 7(6): 334-339, 1994, which is hereby incorporated by reference.

The non-receptor type of tyrosine kinases is also comprised of numerous subfamilies, including Src, Frk, Btk, Csk, Abl, Syk/Zap70, Fes/Fps, Fak, Jak, and Ack. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen, Oncogene, 8:2025-2031 (1993), which is hereby incorporated by reference.

Serine-theoronine kinases play critical roles in intracellular signal transduction and include the multiple families, including STE, CKI, AGC, CAMK, and CMGC. Important subfamilies include, the MAP kinases, p38, JNK and ERK, which modulate signal transduction resulting from such diverse stimuli as mitogenic, stress, proinflammatory and antiapoptotic pathways. Members of the MAP kinase subfamily have been targeted for therapeutic intervention, including p38a, JNK isozymes and Raf.

Since protein kinases and their ligands play critical roles in various cellular activities, deregulation of protein kinase enzymatic activity can lead to altered cellular properties, such as uncontrolled cell growth associated with cancer. In addition to oncological indications, altered kinase signaling is implicated in numerous other pathological diseases. These include, but are not limited to: immunological disorders, cardiovascular diseases, inflammatory diseases, and degenerative diseases. Therefore, both receptor and non-receptor protein kinases are attractive targets for small molecule drug discovery.

One particularly attractive goal for therapeutic use of kinase modulation relates to oncological indications. For example, modulation of protein kinase activity for the treatment of cancer has been demonstrated successfully with the FDA approval of Gleevec® (imatinib mesylate, produced by Novartis Pharmaceutical Corporation of East Hanover, N.J.) for the treatment of Chronic Myeloid Leukemia (CML) and gastrointestinal stroma cancers. Gleevec is a selective Abl kinase inhibitor.

Modulation (particularly inhibition) of cell proliferation and angiogenesis, two key cellular processes needed for tumor growth and survival (Matter A. Drug Disc Technol 2001 6, 1005-1024), is an attractive goal for development of small-molecule drugs. Anti-angiogenic therapy represents a potentially important approach for the treatment of solid tumors and other diseases associated with dysregulated vascularization, including ischemic coronary artery disease, diabetic retinopathy, psoriasis and rheumatoid arthritis. As well, cell antiproliferative agents are desirable to slow or stop the growth of tumors.

The enzyme, p70S6 kinase (p70S6K) is a serine-theoronine kinase that is a component of the phosphatidylinositol 3 kinase (PI3K)/Akt kinase pathway. Both Akt and p70S6K are downstream of phosphatidylinositol-3 kinase (PI3K), and undergo phosphorylation and activation in response to growth factors such as IGF-1, EGF, TGF-α and HGF. The enzyme p70S6K modulates protein synthesis by phosphorylation of the S6 ribosomal protein promoting translation. A role for p70S6K in tumor cell proliferation and protection of cells from apoptosis is supported based on its participation in growth factor receptor signal transduction, overexpression and activation in tumor tissues [Pene et al. (2002) Oncogene 21, 6587; Miyakawa et al. (2003) Endocrin J. 50, 77, 83; Le et al. (2003) Oncogene 22, 484]. Clinical inhibition of p70S6K activation was observed in renal carcinoma patients treated with CCI-779 (rapamycin ester), an inhibitor of the upstream activating kinase, mTOR. A significant linear association between disease progression and inhibition of p70S6K activity was reported [Peralba et al. (2003) Clinical Cancer Research 9, 2887].

Recently, the enzyme p70S6K was found to be implicated in metabolic diseases and disorders. It was reported that the absence of P70S6K protects against age- and diet-induced obesity while enhancing insulin sensitivity [Um et al. (2004) Nature 431, 200-205 and Pende et al. (2000) Nature 408, 994-997]. A role for p70S6K in metabolic diseases and disorders such as obesity, diabetes, metabolic syndrome, insulin resistance, hyperglycemia, hyperaminoacidemia, and hyperlipidemia is supported based upon the findings.

Accordingly, the identification of small-molecule compounds that specifically inhibit, regulate and/or modulate the signal transduction of kinases, particularly p70S6K, is desirable as a means to treat or prevent disease states associated with abnormal cell proliferation and metabolism is an object of this invention.

SUMMARY OF THE INVENTION

In one aspect, the present invention provides compounds for modulating the activity of p70S6 kinases and methods of treating diseases mediated by the activity of p70S6K utilizing the compounds and pharmaceutical compositions thereof. Diseases mediated by p70S6K activity include, but are not limited to, diseases characterized in part by migration, invasion, proliferation, and other biological activities associated with invasive cell growth, and metabolism.

In another aspect, the invention provides methods of screening for modulators of p70S6K activity. The methods comprise combining a composition of the invention, typically p70S6K, and at least one candidate agent and determining the effect of the candidate agent on the p70S6K activity.

In yet another aspect, the invention also provides pharmaceutical kits comprising one or more containers filled with one or more of the ingredients of pharmaceutical compounds and/or compositions of the present invention, including, p70S6K enzyme activity modulators as described herein. Such kits can also include, for example, other compounds and/or compositions (e.g., diluents, permeation enhancers, lubricants, and the like), a device(s) for administering the compounds and/or compositions, and written instructions in a form prescribed by a governmental agency regulating the manufacture, use or sale of pharmaceuticals or biological products, which instructions can also reflects approval by the agency of manufacture, use or sale for human administration.

In still yet another aspect, the invention also provides a diagnostic agent comprising a compound of the invention and, optionally, pharmaceutically acceptable adjuvants and excipients.

These and other features and advantages of the present invention will be described in more detail below with reference to the associated drawings.

DETAILED DESCRIPTION OF THE INVENTION

The compositions of the invention are used to treat diseases associated with abnormal and or unregulated cellular activities. Disease states which can be treated by the methods and compositions provided herein include, but are not limited to, cancer (further discussed below), immunological disorders such as rheumatoid arthritis, graft-host diseases, multiple sclerosis, psoriasis; cardiovascular diseases such as artheroscrosis, myocardioinfarction, ischemia, stroke and restenosis; metabolic disorders and diseases such as diabetes, obesity and hypercholesterolemia; and other inflammatory and degenerative diseases such as interbowel diseases, osteoarthritus, macular degeneration, diabetic retinopathy.

It is appreciated that in some cases the cells may not be in a hyper- or hypo-proliferative and/or migratory state (abnormal state) and still require treatment. For example, during wound healing, the cells may be proliferating "normally", but proliferation and migration enhancement may be desired. Alternatively, reduction in "normal" cell proliferation and/or migration rate may be desired.

Embodiment [0022]:

The present invention comprises a compound for modulating p70S6K activity according to Formula I,

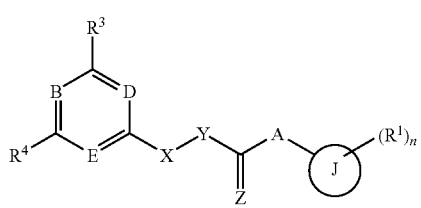

I or a pharmaceutically acceptable salt, hydrate, or prodrug thereof, wherein,

B, D, and E are each independently either =N— or =C($R^2$)—, provided at least one of B, D, and E is =N—;

at each occurrence, each of $R^1$, $R^2$, and $R^3$ is independently selected from —H, halogen, trihalomethyl, —CN, —$NO_2$, —$OR^5$, —$N(R^5)OR^5$, —$ON(R^5)R^5$, —$N(R^5)N(R^5)R^5$, —$N(R^5)R^5$, —$S(O)_{0-2}R^5$, —$SO_2N(R^5)R^5$, —$CO_2R^5$, —$C(O)N(R^5)R^5$, —$N(R^5)SO_2R^5$, —$N(R^5)C(O)R^5$, —$N(R^5)CO_2R^5$, —$C(O)R^5$, —$C(=NR^7)N(R^5)R^5$, —$C(=NR^7)R^5$, —$C(=NR^7)OR^5$, —$N(R^5)C(=NR^7)N(R^5)R^5$, optionally substituted lower alkyl, optionally substituted lower alkenyl, optionally substituted lower alkynyl, optionally substituted aryl, optionally substituted heterocyclyl, optionally substituted heterocyclylalkyl, and optionally substituted arylalkyl;

n is zero to five;

$R^4$ is selected from —H, halogen, —CN, —$NO_2$, —$N(R^5)OR^5$, —$ON(R^5)R^5$, —$N(R^5)N(R^5)R^5$, —$OR^5$, —$N(R^5)R^5$, —$S(O)_{0-2}R^5$, —$SO_2N(R^5)R^5$, —$CO_2R^5$, —$C(O)N(R^5)R^5$, —$N(R^5)SO_2R^5$, —$N(R^5)C(O)R^5$, —$N(R^5)CO_2R^5$, —$C(O)R^5$, —$C(=NR^7)N(R^5)R^5$, —$C(=NR^7)R^5$, —$C(=NR^7)OR^5$, —$N(R^5)C(=NR^7)N(R^5)R^5$, optionally substituted lower alkyl, optionally substituted lower alkenyl, optionally substituted lower alkyl, optionally substituted heterocyclyl, optionally substituted heterocyclylalkyl, and optionally substituted arylalkyl;

$R^2$ and $R^3$, together with the atom or atoms to which they are attached, can combine to form a three- to seven-membered optionally substituted heterocyclyl, optionally substituted aryl, or optionally substituted cycloalkyl;

$R^2$ and $R^4$, together with the atom or atoms to which they are attached, can combine to form a three- to seven-membered optionally substituted heterocyclyl, optionally substituted aryl, or optionally substituted cycloalkyl;

each $R^5$ is independently selected from —H, optionally substituted lower alkyl, optionally substituted aryl, optionally substituted lower arylalkyl, optionally substituted heterocyclyl, optionally substituted lower heterocyclylalkyl, and a single bond to an atom of $R^1$;

two of $R^5$, together with the atom or respective atoms to which they are attached, can combine to form an optionally substituted three- to seven-membered heterocyclic;

$R^5$ and $R^6$, together with the atom or atoms to which they are attached, can combine to form a five- to seven-membered optionally substituted heterocyclyl;

$R^5$ and $R^7$, together with the atom or atoms to which they are attached, can combine to form a five- to seven-membered optionally substituted heterocyclyl;

each of X and Y is independently selected from —C(=O)—, —C($R^6$)$R^6$—, —O—, —N($R^5$)—, —C(=N$R^7$)—, and —S(O)$_{0-2}$—; provided when X is —O— or —N($R^5$)—, then Y cannot be —C(H)$R^{6a}$—, where $R^{6a}$ is —C($R^{20}$)($R^{21}$)$R^{22}$ wherein at least one of $R^{20}$, $R^{21}$ and $R^{22}$ is selected from phenyl, napthyl, cyclohexyl, dihydronapthyl tetrahydronapthyl, and a five- to six-membered heteroaryl, each optionally substituted;

or X and Y can combine to form either —C($R^6$)=C($R^6$)— or —C≡C—;

Z is selected from O, S, and a double bond to an atom of $R^1$;
A is either —N($R^5$)— or a single bond;

each $R^6$ is independently selected from —H, halogen, trihalomethyl, —CN, —NO$_2$, —NH$_2$, —O$R^5$, —N($R^5$)$R^5$, —S(O)$_{0-2}$$R^5$, —SO$_2$N($R^5$)$R^5$, —CO$_2$$R^5$, —C(O)N($R^5$)$R^5$, —N($R^5$)SO$_2$$R^5$, —N($R^5$)C(O)$R^5$, —N($R^5$)CO$_2$$R^5$, —C(O)$R^5$, optionally substituted lower alkyl, optionally substituted aryl, optionally substituted heterocyclyl, optionally substituted heterocyclylalkyl, optionally substituted arylalkyl, and a single bond to an atom of $R^2$ of D or E when said either D or E is =C($R^2$)—;

two of $R^6$, together with the atom or atoms to which they are attached, can combine to form one of an optionally substituted three to seven-membered alicyclic, an optionally substituted three to seven-membered heteroalicyclic, and a double bond to an atom of $R^2$ of D or E when said either D or E is =C($R^2$)—;

each $R^7$ is independently selected from —H, —CN, —NO$_2$, —N($R^5$)$R^5$, —O$R^5$, —S(O)$_{0-2}$$R^5$, —SO$_2$N($R^5$)$R^5$, —CO$_2$$R^5$, optionally substituted lower alkyl, optionally substituted lower alkenyl, optionally substituted lower alkynyl, and a single bond to a carbon of 3; and J is selected from an optionally substituted five- to ten-membered aryl and an optionally substituted five- to ten-membered heteroaryl;

provided the compound is not one of: 2-(2-amino-5-cyano-6-methylsulfanyl-pyrimidin-4-ylsulfanyl)-N-(3-trifluoromethyl-phenyl)-acetamide, 2-{[2-amino-5-cyano-6-(methylthio)pyrimidin-4-yl]thio}-N-[3-(butyloxy)phenyl]acetamide, 2-{[2-amino-5-cyano-6-(methylthio)pyrimidin-4-yl]thio}-N-1,3-benzothiazol-2-ylacetamide, 2-{[2-amino-5-cyano-6-(methylthio)pyrimidin-4-yl]thio}-N-(5-ethyl-1,3,4-thiadiazol-2-yl)acetamide, 2-{[2-amino-5-cyano-6-(methylthio)pyrimidin-4-yl]thio}-N-(4-methyl-1,3-thiazol-2-yl)acetamide, 2-amino-4-{[2-(3,5-dimethyl-1H-pyrazol-1-yl)-2-oxoethyl]thio}-6-(methylthio)pyrimidine-5-carbonitrile, 2-{[2-amino-5-cyano-6-(methylthio)pyrimidin-4-yl]thio}-N-1,3-thiazol-2-ylacetamide, 2-(5-cyano-2-methylsulfanyl-pyrimidin-4-ylsulfanyl)-N-phenyl-acetamide, 5-amino-2-methylsulfanyl-thieno[2,3-d]pyrimidine-6-carboxylic acid phenylamide, 2-(6-amino-5-cyano-2-methylsulfanyl-pyrimidin-4-ylsulfanyl)-N-phenyl-acetamide, 4,5-diamino-2-(2-methoxy-ethoxy)-thieno[2,3-d]pyrimidine-6-carboxylic acid phenylamide, 2-(5-cyano-6-phenyl-2-phenylcarbamoylmethylsulfanyl-pyrimidin-4-ylsulfanyl)-N-phenyl-acetamide, and a 2-(6-amino-3,5-dicyano-pyridin-2-ylsulfanyl)-N-phenyl-acetamide derivative.

Embodiment [0023]:
In one example, the compound is according to Embodiment [0022], wherein J is either a six-membered aryl or a five- to six-membered heteroaryl.

Embodiment [0024]:
In another example, the compound is according to Embodiment [0023], wherein D is =C($R^2$)—.

Embodiment [0025]:
In another example, the compound is according to Embodiment [0024], wherein $R^4$ is —N($R^5$)$R^5$.

Embodiment [0026]:
In another example, the compound is according to Embodiment [0025], of Formula II,

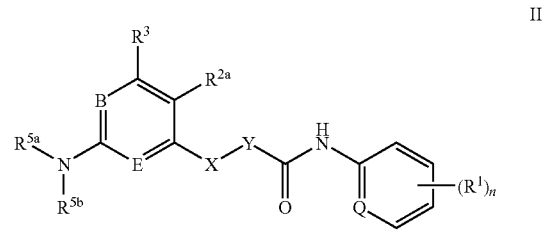

wherein, $R^1$, $R^2$, $R^3$, $R^5$, n, B, E, X, and Y are as defined above; and Q is either =N— or =C(H)—.

Embodiment [0027]:
In another example, the compound is according to Embodiment [0026], wherein $R^{2a}$ is selected from halogen, —CN, —C(=O)N($R^5$)$R^5$, —CF$_3$, —CO$_2$$R^5$, —C($R^5$)=C($R^5$)$R^5$, —C≡C—$R^5$, and —NO$_2$;

Embodiment [0028]:
In another example, the compound is according to Embodiment [0027], wherein at least one of $R^{5a}$ and $R^{5b}$ is —H.

Embodiment [0029]:
In another example, the compound is according to Embodiment [0028], wherein $R^3$ is selected from —O$R^5$, —N$R^5$$R^5$, and —S(O)$_{0-2}$$R^5$.

Embodiment [0030]:
In another example, the compound is according to Embodiment [0029], wherein at least one of B and E is =N—.

Embodiment [0031]:
In another example, the compound is according to Embodiment [0030], wherein $R^1$ is selected from halogen, —O$R^5$, —N$R^5$$R^5$, —S(O)$_{0-2}$$R^5$, —NO$_2$, perhaloalkyl, optionally substituted lower alkyl, optionally substituted aryl, and optionally substituted arylalkyl.

Embodiment [0032]:
In another example, the compound is according to Embodiment [0031], wherein $R^1$ is selected from halogen, —O$R^5$, —N$R^5$$R^5$, —S(O)$_{0-1}$$R^5$, —NO$_2$, perhaloalkyl, and optionally substituted lower alkyl.

Embodiment [0033]:
In another example, the compound is according to Embodiment [0032], wherein A is —N($R^5$)—.

Embodiment [0034]:

In another example, the compound is according to Embodiment [0033], of Formula III,

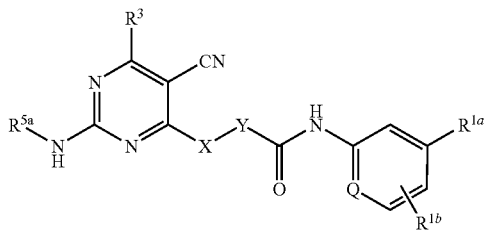

wherein, $R^3$, $R^5$, X, Y, and Q are as defined above; $R^{1a}$ is selected from halogen, lower perfluoroalkyl, —$NO_2$, —$OR^5$, and optionally substituted $C_{1-4}$alkyl; and $R^{1b}$ is selected from halogen, —$OR^5$, —$N(R^5)R^5$, —$SR^5$, perfluoroalkyl, and optionally substituted lower alkyl.

Embodiment [0035]:

In another example, the compound is according to Embodiment [0034], wherein $R^{1a}$ is selected from —$NO_2$, halogen, perfluoroalkyl, haloalkyl, optionally substituted $C_{1-2}$alkyl, and optionally substituted —O—$C_{1-2}$alkyl.

Embodiment [0036]:

In another example, the compound is according to Embodiment [0035], wherein $R^3$ is selected from optionally substituted —O—$C_{1-4}$alkyl, —O—$C_{1-4}$ perfluoroalkyl, optionally substituted —N(H)$C_{1-4}$alkyl, optionally substituted —N($C_{1-4}$ alkyl)$C_{1-4}$alkyl, optionally substituted —S(O)$_{0-2}$—$C_{1-4}$alkyl, and optionally substituted —S(O)$_{0-2}$—$C_{14}$ perfluoroalkyl.

Embodiment [0037]:

In another example, the compound is according to Embodiment [0036], wherein Y is either —N(H)— or —C($R^6$)$R^6$—.

Embodiment [0038]:

In another example, the compound is according to Embodiment [0037], wherein X is selected from —O—, —N($R^5$)— and —S—.

Embodiment [0039]:

In another example, the compound is according to Embodiment [0038], wherein Y is —C($R^6$)$R^6$—; wherein each $R^6$ is independently selected from —H, halogen, trihalomethyl, —$NH_2$, optionally substituted —O—$C_{1-4}$alkyl, optionally substituted —N(H)$C_{1-4}$alkyl, optionally substituted —S—$C_{1-4}$alkyl, optionally substituted lower alkyl, optionally substituted heterocyclyl, and optionally substituted heterocyclylalkyl.

Embodiment [0040]:

In another example, the compound is according to Embodiment [0039], wherein Y is —C(H)$R^6$—; wherein $R^6$ is independently selected from —H, halogen, trihalomethyl, —$NH_2$, optionally substituted —O—$C_{1-4}$alkyl, optionally substituted —N(H)$C_{1-4}$alkyl, optionally substituted —S—$C_{1-4}$alkyl, optionally substituted lower alkyl, optionally substituted heterocyclyl, and optionally substituted heterocyclylalkyl.

Embodiment [0041]:

In another example, the compound is according to Embodiment [0040], wherein Q is =CH—.

Embodiment [0042]:

In another example, the present invention comprises a compound for modulating p70S6K activity according to Formula IV,

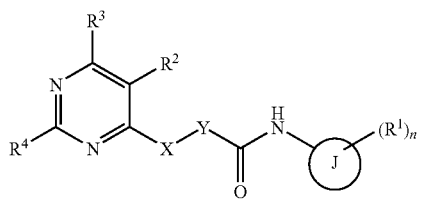

or a pharmaceutically acceptable salt, hydrate, or prodrug thereof, wherein, $R^1$ is selected from halogen, —$OR^5$, —$N(R^5)R^5$, —$S(O)_{0-2}$ $R^5$, —$NO_2$, —$C(O)R^5$, perhaloalkyl, optionally substituted lower alkyl, optionally substituted aryl, and optionally substituted arylalkyl.

n is zero to five;

$R^2$ is selected from halogen, —CN, —C(=O)N($R^5$)$R^5$, —$CF_3$, —$CO_2R^5$, —C($R^5$)=C($R^5$)$R^5$, —C≡C—$R^5$, and —$NO_2$;

$R^3$ is selected from —H, halogen, trihalomethyl, —CN, —$NO_2$, —$OR^5$, —N($R^5$)$OR^5$, —ON($R^5$)$R^5$, —N($R^5$)N($R^5$)$R^5$, —N($R^5$)$R^5$, —$S(O)_{0-2}R^5$, —$SO_2N(R^5)R^5$, —$CO_2R^5$, —C(O)N($R^5$)$R^5$, —N($R^5$)$SO_2R^5$, —N($R^5$)C(O)$R^5$, —N($R^5$)$CO_2R^5$, —C(O)$R^5$, —C(=$NR^7$)N($R^5$)$R^5$, —C(=$NR^7$)$R^5$, —C(=$NR^7$)$OR^5$, —N($R^5$)C(=$NR^7$)N($R^5$)$R^5$, optionally substituted lower alkyl, optionally substituted lower alkenyl, optionally substituted lower alkynyl, optionally substituted aryl, optionally substituted heterocyclyl, optionally substituted heterocyclylalkyl, and optionally substituted arylalkyl;

$R^4$ is selected from —CN, halogen, —$NO_2$, —N($R^5$)$OR^5$, —ON($R^5$)$R^5$, —N($R^5$)N($R^5$)$R^5$, —$OR^5$, —N($R^5$)$R^5$, —$SO_2N(R^5)R^5$, —C(O)N($R^5$)$R^5$, —C(=$NR^7$)N($R^5$)$R^5$, —C(=$NR^7$)$R^5$, —C(=$NR^7$)$OR^5$, —N($R^5$)C(=$NR^7$)N($R^5$)$R^5$, optionally substituted lower alkyl, optionally substituted heterocyclyl, and optionally substituted heterocyclylalkyl;

each $R^5$ is independently selected from —H, optionally substituted lower alkyl, optionally substituted aryl, optionally substituted lower arylalkyl, optionally substituted heterocyclyl, and optionally substituted lower heterocyclylalkyl;

two of $R^5$, together with the atom or respective atoms to which they are attached, can combine to form an optionally substituted three- to seven-membered heterocyclic;

$R^5$ and $R^6$, together with the atom or atoms to which they are attached, can combine to form a five- to seven-membered optionally substituted heterocyclyl;

$R^5$ and $R^7$, together with the atom or atoms to which they are attached, can combine to form a five- to seven-membered optionally substituted heterocyclyl;

each of X and Y is independently selected from —C(=O)—, —C($R^6$)$R^6$—, —O—, —N($R^5$)—, —C(=$NR^7$)—, and —$S(O)_{0-2}$—; provided when X is —O— or —N($R^5$)—, then Y cannot be —C(H)$R^{6a}$—, where $R^{6a}$, is —C($R^{20}$)($R^{21}$)$R^{22}$ wherein at least one of $R^{20}$, $R^{21}$ and $R^{22}$ is selected from phenyl, napthyl, cyclohexyl, dihydronapthyl tetrahydronapthyl, and a five- to six-membered heteroaryl, each optionally substituted;

or X and Y can combine to form either —C($R^6$)=C($R^6$)— or —C≡C—;

each $R^6$ is independently selected from —H, halogen, trihalomethyl, —CN, —$NO_2$, —$NH_2$, —$OR^5$, —$N(R^5)R^5$, —$S(O)_{0-2}R^5$, —$SO_2N(R^5)R^5$, —$CO_2R^5$, —$C(O)N(R^5)R^5$, —$N(R^5)SO_2R^5$, —$N(R^5)C(O)R^5$, —$N(R^5)CO_2R^5$, —$C(O)R^5$, optionally substituted lower alkyl, optionally substituted aryl, optionally substituted heterocyclyl, optionally substituted heterocyclylalkyl, optionally substituted arylalkyl, and a single bond to an atom of $R^1$;

two of $R^6$, together with the atom or atoms to which they are attached, can combine to form either an optionally substituted three to seven-membered alicyclic or an optionally substituted three to seven-membered heteroalicyclic;

each $R^7$ is independently selected from —H, —CN, —$NO_2$, —$N(R^5)R^5$, —$OR^5$, —$S(O)_{0-2}R^5$, —$SO_2N(R^5)R^5$, —$CO_2R^5$, optionally substituted lower alkyl, optionally substituted lower alkenyl, optionally substituted lower alkynyl, and a single bond to a carbon of J; and J is selected from an optionally substituted five- to ten-membered aryl and an optionally substituted five- to ten-membered heteroaryl;

provided the compound is not one of: 2-(2-amino-5-cyano-6-methylsulfanyl-pyrimidin-4-ylsulfanyl)-N-(3-trifluoromethyl-phenyl)-acetamide, 2-{[2-amino-5-cyano-6-(methylthio)pyrmidin-4-yl]thio}-N-[3-(butyloxy)phenyl] acetamide, 2-{[2-amino-5-cyano-6-(methylthio)pyrimidin-4-yl]thio}-N-1,3-benzothiazol-2-ylacetamide, 2-{[2-amino-5-cyano-6-(methylthio)pyrimidin-4-yl]thio}-N-(5-ethyl-1,3,4-thiadiazol-2-yl)acetamide, 2-{[2-amino-5-cyano-6-(methylthio)pyrimidin-4-yl]thio}1-N-(4-methyl-1,3-thiazol-2-yl)acetamide, 2-amino-4-{[2-(3,5-dimethyl-1H-pyrazol-1-yl)-2-oxoethyl]thio}-6-(methylthio)pyrimidine-5-carbonitrile, 2-{[2-amino-5-cyano-6-(methylthio)pyrimidin-4-yl]thio}-N-1,3-thiazol-2-ylacetamide, 2-(5-cyano-2-methylsulfanyl-pyrimidin-4-ylsulfanyl)-N-phenyl-acetamide, 5-amino-2-methylsulfanyl-thieno[2,3-d]pyrimidine-6-carboxylic acid phenylamide, 2-(6-amino-5-cyano-2-methylsulfanyl-pyrimidin-4-ylsulfanyl)-N-phenyl-acetamide, 4,5-diamino-2-(2-methoxy-ethoxy)-thieno[2,3-d]pyrimidine-6-carboxylic acid phenylamide, 2-(5-cyano-6-phenyl-2-phenylcarbamoylmethylsulfanyl-pyrimidin-4-ylsulfanyl)-N-phenyl-acetamide, and a 2-(6-amino-3,5-dicyano-pyridin-2-ylsulfanyl)-N-phenyl-acetamide derivative.

Embodiment [0043]:

In another example, the compound, is according to Embodiment [0042], wherein $R^4$ is —$NR^{5a}R^{5b}$; wherein at least one of $R^{5a}$ and $R^{5b}$ is —H.

Embodiment [0044]:

In another example, the compound is according to Embodiment [0043], wherein X is selected from —O—, —$N(R^5)$—, and —$S(O)_{0-2}$—.

Embodiment [0045]:

In another example, the compound is according to Embodiment [0044], wherein Y is either —$C(R^6)R^6$— or —$N(R^5)$—.

Embodiment [0046]:

In another example, the compound is according to Embodiment [0045], wherein J is either phenyl or pyridyl.

Embodiment [0047]:

In another example, the compound is according to Embodiment [0046], wherein $R^4$ is —$NH_2$.

Embodiment [0048]:

In another example, the compound is according to Embodiment [0047], wherein at least one of $R^1$ is selected from halo, —$NO_2$, —$OR^5$, perfluoroalkyl, haloalkyl, and optionally substituted $C_{1-4}$alkyl.

Embodiment [0049]:

In another example, the compound is according to Embodiment [0048], of Formula V,

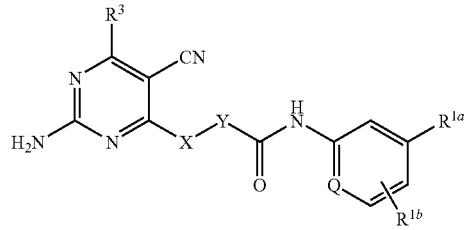

wherein $R^1$, $R^3$, X, and Y are as defined above; and Q is either =N— or =C(H)—.

Embodiment [0050]:

In another example, the compound is according to Embodiment [0049], wherein $R^{1a}$ is selected from halo, lower perfluoroalkyl, —$NO_2$, optionally substituted —O—$C_{1-4}$alkyl, and optionally substituted $C_{1-4}$alkyl.

Embodiment [0051]:

In another example, the compound is according to Embodiment [0050], wherein $R^3$ is selected from optionally substituted —O—$C_{1-4}$alkyl, —O—$C_{1-4}$ perfluoroalkyl, optionally substituted —N(H)$C_{1-4}$alkyl, optionally substituted —N($C_{1-4}$alkyl)$C_{1-4}$alkyl, optionally substituted —$S(O)_{0-2}$—$C_{1-4}$alkyl, and optionally substituted —$S(O)_{0-2}$—$C_{1-4}$ perfluoroalkyl.

Embodiment [0052]:

In another example, the compound is according to Embodiment [0051], wherein Y is —$C(R^6)R^6$—; wherein each $R^6$ is independently selected from —H, halogen, trihalomethyl, —$NH_2$, optionally substituted —O—$C_{1-4}$alkyl, optionally substituted —N(O)$C_{1-4}$alkyl, optionally substituted —S—$C_{1-4}$alkyl, optionally substituted lower alkyl, optionally substituted heterocyclyl, and optionally substituted heterocyclylalkyl.

Embodiment [0053]:

In another example, the compound is according to Embodiment [0052], wherein Y is —C(H)$R^6$—; wherein $R^6$ is independently selected from —H, halogen, trihalomethyl, —$NH_2$, optionally substituted —O—$C_{1-4}$alkyl, optionally substituted —N(H)$C_{1-4}$alkyl, optionally substituted —S—$C_{1-4}$alkyl, optionally substituted lower alkyl, optionally substituted heterocyclyl, and optionally substituted heterocyclylalkyl.

Embodiment [0054]:

In another example, the compound is according to Embodiment [0053], wherein Q is =C(H)—.

Embodiment [0055]:

In another example, the compound is according to Embodiment [0022], selected from

TABLE 1

| Entry | Name | Structure |
|---|---|---|
| 1 | 2-[(3-cyano-4,6-dimethyl-5-nitropyridin-2-yl)oxy]-N-[3-(trifluoromethyl)phenyl]acetamide | 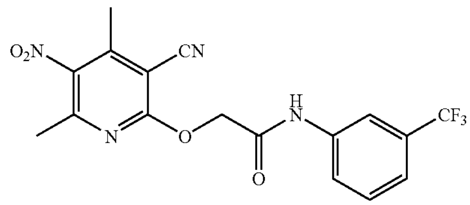 |
| 2 | $N^2$-(2-amino-6-chloropyrimidin-4-yl)-N-[3-(trifluoromethyl)phenyl]glycinamide | 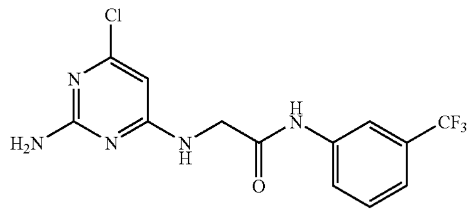 |
| 3 | [2-amino-6-(methylthio)pyrimidin-4-yl]methyl [3-(trifluoromethyl)phenyl]carbamate | 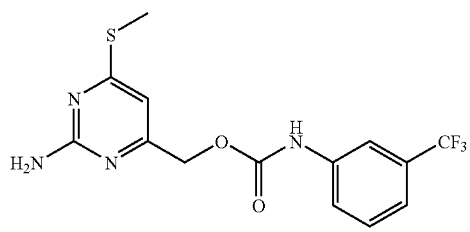 |
| 4 | 2-{[2-amino-5-cyano-6-(methylthio)pyrimidin-4-yl]thio}-N-[5-(trifluoromethyl)pyridin-2-yl]acetamide | 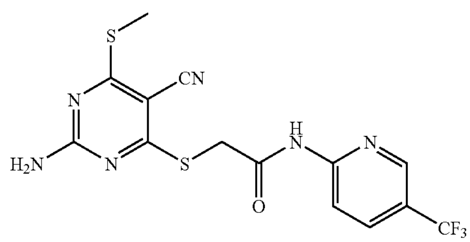 |
| 5 | $N^2$-[2-amino-6-(methylthio)pyrimidin-4-yl]-N-[3-(trifluoromethyl)phenyl]glycinamide | 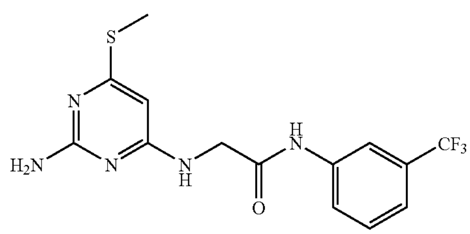 |
| 6 | 2-{[2-amino-6-(methylthio)pyrimidin-4-yl]oxy}-N-[3-(trifluoromethyl)phenyl]acetamide | 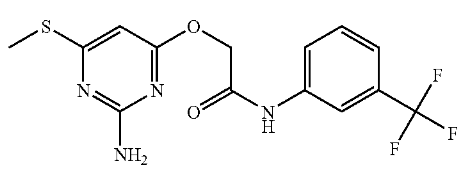 |
| 7 | 2-{[2-amino-5-cyano-6-(methylthio)pyrimidin-4-yl]thio}-N-[3-(methyloxy)phenyl]acetamide | 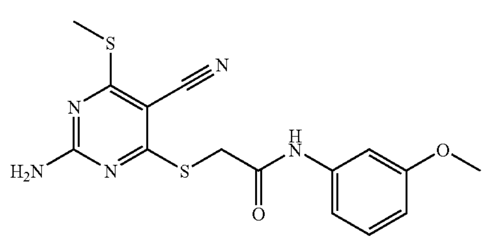 |

TABLE 1-continued

| Entry | Name | Structure |
|---|---|---|
| 8 | N²-(2-amino-6-morpholin-4-ylpyrimidin-4-yl)-N-[3-(trifluoromethyl)phenyl]glycinamide | 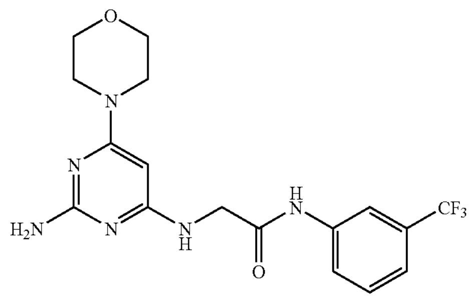 |
| 9 | 2-{[2-amino-5-cyano-6-(methylthio)pyrimidin-4-yl]thio}-N-(4-chlorophenyl)acetamide | 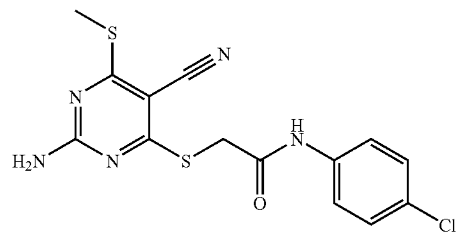 |
| 10 | 2-{[2-amino-6-(1H-1,2,3-benzotriazol-1-yloxy)pyrimidin-4-yl]thio}-N-[3-(trifluoromethyl)phenyl]acetamide | 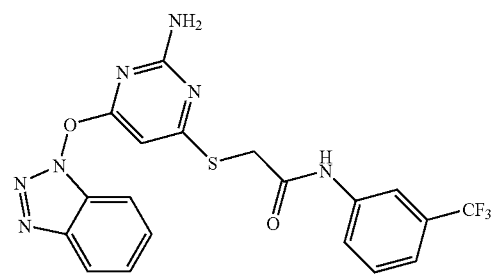 |
| 11 | 2-{[2-amino-5-cyano-6-(methylthio)pyrimidin-4-yl]thio}-N-(3-chlorophenyl)acetamide | 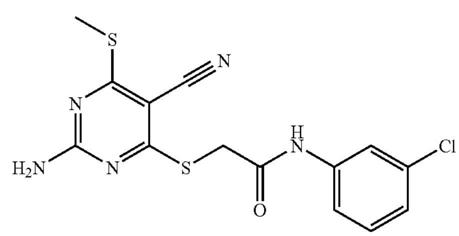 |
| 12 | N²-(2-amino-6-chloro-5-formylpyrimidin-4-yl)-N-[3-(trifluoromethyl)phenyl]glycinamide | 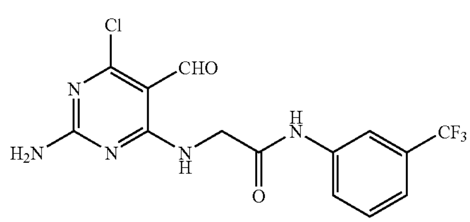 |
| 13 | N²-[2-amino-5-formyl-6-(methylthio)pyrimidin-4-yl]-N-[3-(trifluoromethyl)phenyl]glycinamide | 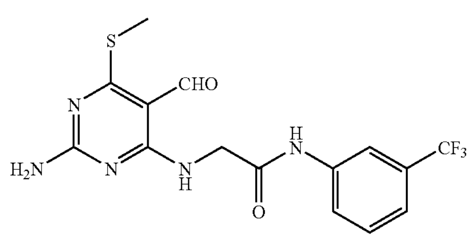 |

TABLE 1-continued

| Entry | Name | Structure |
|-------|------|-----------|
| 14 | 2-{[2-amino-5-cyano-6-methylthio)pyrimidin-4-yl]oxy}-N-[3-(trifluoromethyl)phenyl]acetamide | 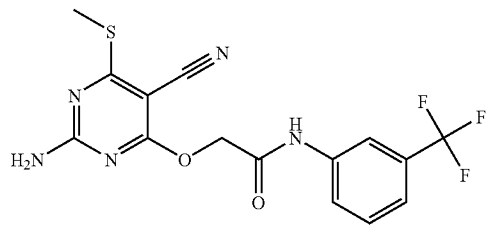 |
| 15 | 2-{(2-amino-6-chloropyrimidin-4-yl)thio]-N-[3-(trifluoromethyl)phenyl]acetamide | 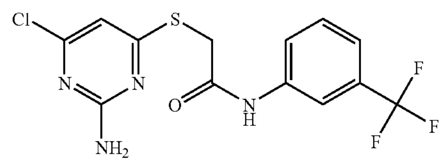 |
| 16 | 2-{(2-amino-5-cyano-6-(methylthio)pyrimidin-4-yl]thio}-N-methyl-N-[3-(trifluoromethyl)phenyl]acetamide | 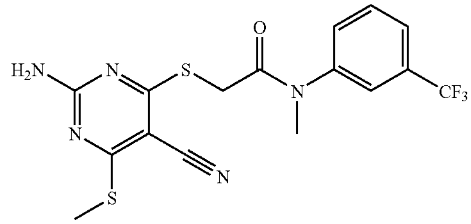 |
| 17 | $N^2$-[4-amino-6-(methylthio)-1,3,5-triazin-2-yl]-N-[3-(trifluoromethy])phenyl]glycinamide | 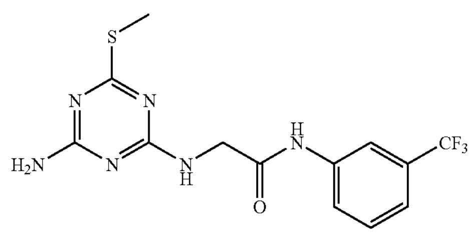 |
| 18 | $N^2$-[4-(dimethylamino)-6-(methylthio)-1,3,5-triazin-2-yl]-N-[3-(trifluoromethyl)phenyl]glycinamide | 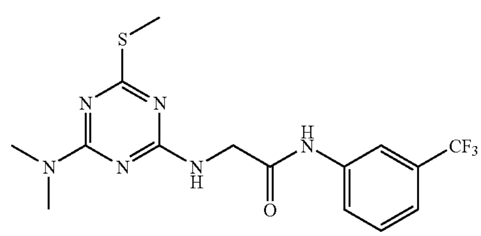 |
| 19 | $N^2$-[4-(methylamino)-6-(methylthio)-1,3,5-triazin-2-yl]-N-[3-(trifluoromethyl)phenyl]glycinamide | 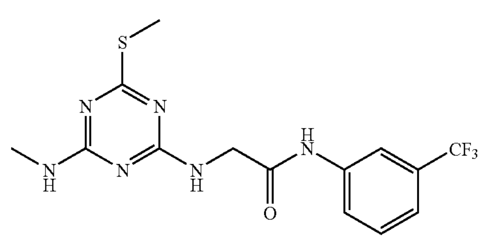 |
| 20 | $N^2$-[2-amino-5-cyano-6-(methylthio)pyrimidin-4-yl]-N-[3-(trifluoromethyl)phenyl]glycinamide | 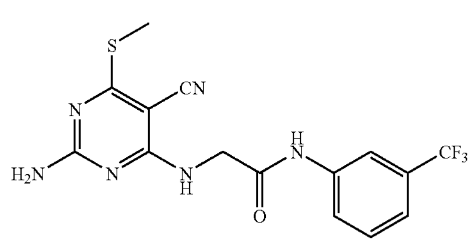 |

TABLE 1-continued

| Entry | Name | Structure |
|---|---|---|
| 21 | 2-{[2-amino-5-cyano-6-(methylthio)pyrimidin-4-yl]thio}-N-[3-(trifluoromethyl)phenyl]acetamide | 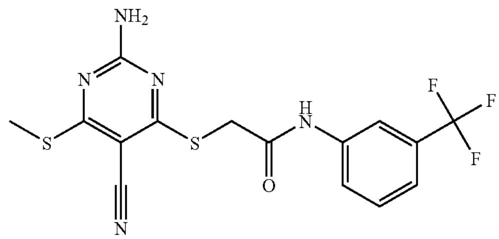 |
| 22 | 2-([2-amino-5-cyano-6-(methylthio)pyrimidin-4-yl]thio}-N-[3-(butyloxy)phenyl]acetamide | 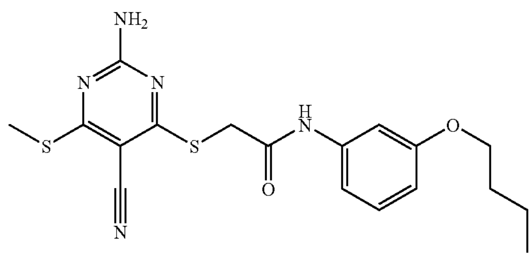 |
| 23 | 2-([2-amino-5-cyano-6-(methylthio)pyrimidin-4-yl]thio}-N-1,3-benzothiazol-2-ylacetamide | 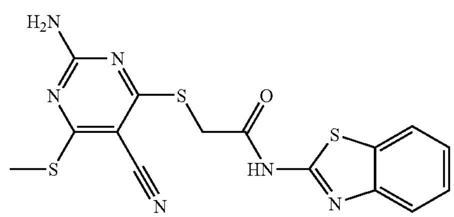 |
| 24 | 2-{[2-amino-5-cyano-6-(methylthio)pyrimidin-4-yl]thio}-N-(5-ethyl-1,3,4-thiadiazol-2-yl)acetamide | 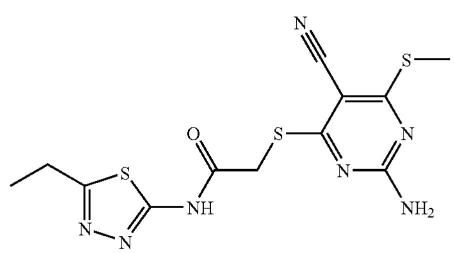 |
| 25 | 2-{[2-amino-5-cyano-6-(methylthio)pyrimidin-4-yl]thio}-N-(4-methyl-1,3-thiazol-2-yl)acetamide | 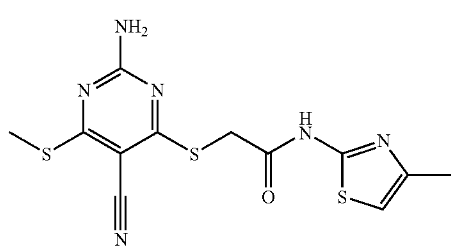 |
| 26 | 2-amino-4-{[2-(3,5-dimethyl-1H-pyrazol-1-yl)-2-oxoethyl]thio}-6-(methylthio)pyrimidine-5-carbonitrile | 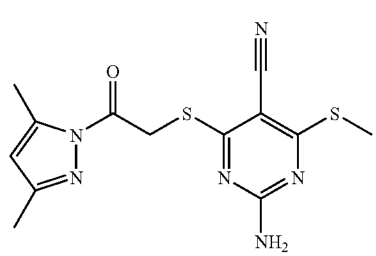 |

TABLE 1-continued

| Entry | Name | Structure |
|---|---|---|
| 27 | 2-{[2-amino-5-cyano-6-(methylthio)pyrimidin-4-yl]thio}-N-1,3-thiazol-2-ylacetamide | 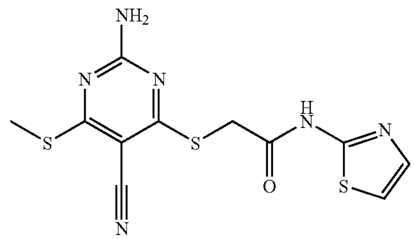 |
| 28 | ethyl 5-[({[2-amino-5-cyano-6-(methylthio)pyrimidin-4-yl]thio}acetyl)amino]-4-cyano-3-methylthiophene-2-carboxylate | 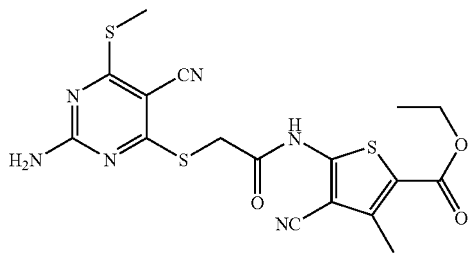 |
| 29 | 2-{[2-amino-5-cyano-6-(methylthio)pyrimidin-4-yl]thio}-N-pyridin-2-ylacetamide | 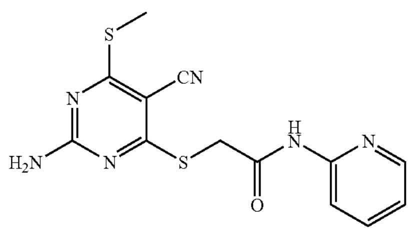 |
| 30 | 2-amino-4-({2-[2,5-bis(methyloxy)phenyl]-2-oxoethyl}thio)-6-(methylthio)pyrimidine-5-carbonitrile | 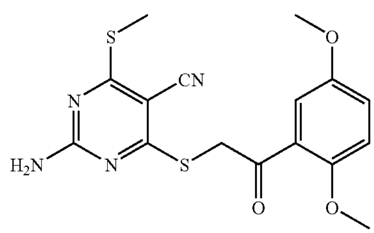 |
| 31 | 2-{[2-amino-5-cyano-6-(methylthio)pyrimidin-4-yl]thio}-N-[4-fluoro-3-(trifluoromethyl)phenyl]acetamide | 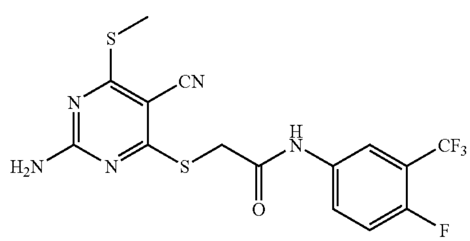 |
| 32 | 2-[(2,6-diaminopyrimidin-4-yl)thio]-N-[4-fluoro-3-(trifluoromethyl)phenyl]acetamide | 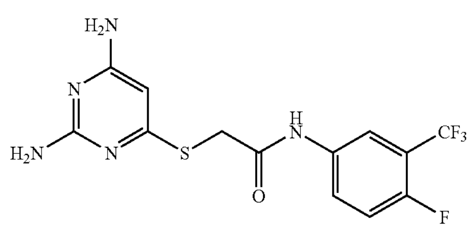 |

TABLE 1-continued

| Entry | Name | Structure |
|---|---|---|
| 33 | 2-[(2,6-diaminopyrimidin-4-yl)thio]-N-[3-(trifluoromethyl)phenyl]acetamide | 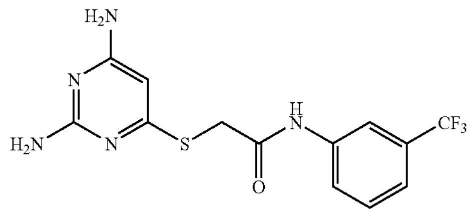 |
| 34 | 2-{[2-amino-5-cyano-6-(methylthio)pyrimidin-4-yl]thio}-N-[4-chloro-3-(trifluoromethyl)phenyl]acetamide | 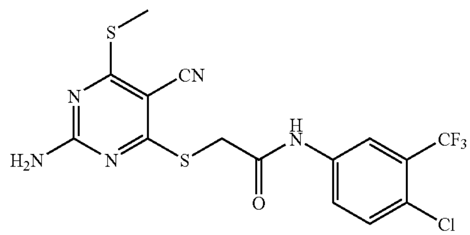 |
| 35 | 2-amino-4-(methylthio)-6-({2-oxo-1-[3-(trifluoromethyl)phenyl]pyrrolidin-3-yl}thio)pyrimidine-5-carbonitrile | 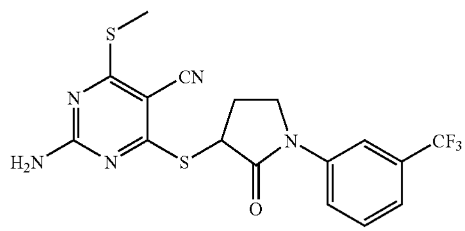 |
| 36 | 2-{[2-amino-5-cyano-6-(methylthio)pyrimidin-4-yl]thio}-N-[6-(trifluoromethyl)pyridin-2-yl]acetamide | 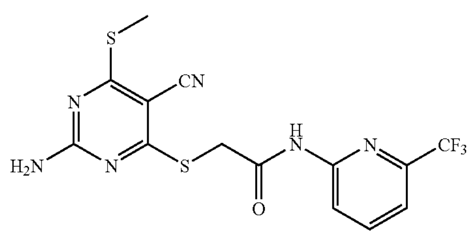 |
| 37 | 2-{[2-amino-5-cyano-6-(methylthio)pyrimidin-4-yl]thio}-N-[4-(trifluoromethyl)pyridin-2-yl]acetamide | 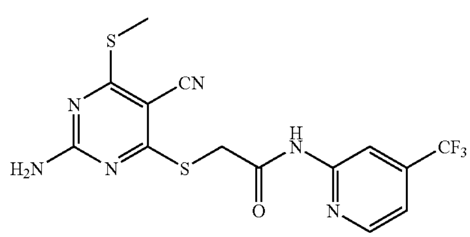 |
| 38 | {6-(methylthio)-2-[(phenylmethyl)amino]pyrimidin-4-yl}methyl [3-(trifluoromethyl)phenyl]carbamate | 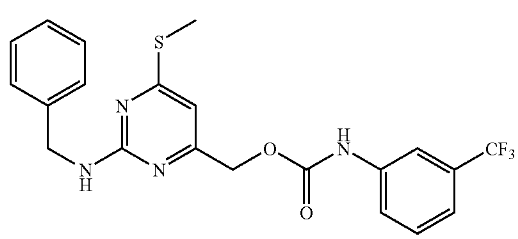 |

TABLE 1-continued

| Entry | Name | Structure |
|---|---|---|
| 39 | [6-(methylamino)-2-(methylthio)pyrimidin-4-yl]methyl[3-(trifluoromethyl)phenyl]carbamate | 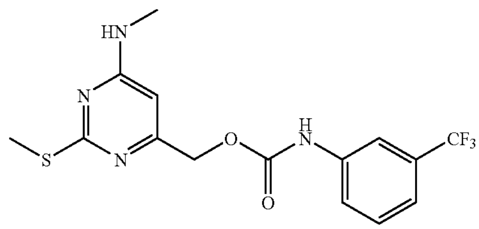 |
| 40 | {2-(methylthio)-6-[(phenylmethyl)amino]pyrimidin-4-yl}methyl[3-(trifluoromethyl)phenyl]carbamate | 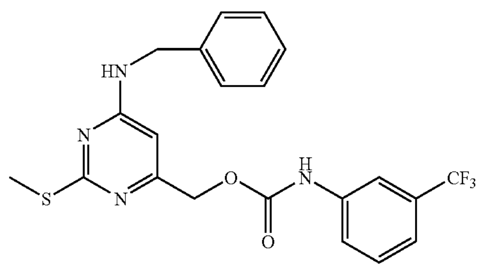 |
| 41 | 2-{[2-(acetylamino)-5-cyano-6-(methylthio)pyrimidin-4-yl]thio}-N-[3-(trifluoromethyl)phenyl]acetamide | 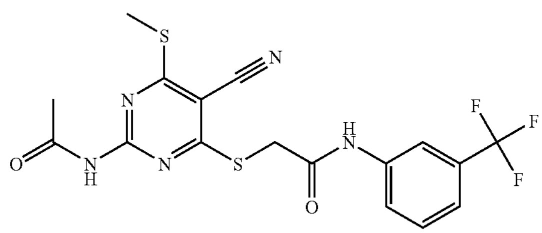 |
| 42 | (2S)-2-{[2-amino-5-cyano-6-(methylthio)pyrimidin-4-yl]oxy}-N-[3-(trifluoromethyl)phenyl]propanamide | 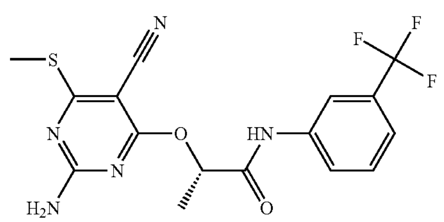 |
| 43 | 2-[(2-amino-6-chloro-5-formylpyrimidin-4-yl)thio)-N-[3-(trifluoromethyl)phenyl]acetamide | 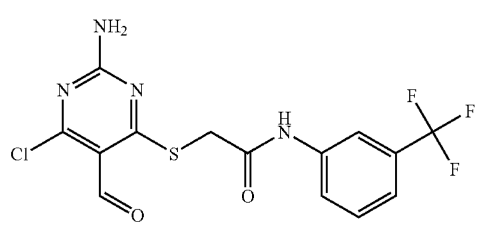 |
| 44 | | 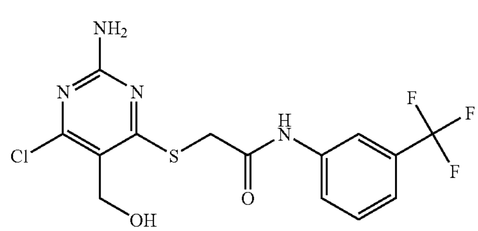 |

TABLE 1-continued

| Entry | Name |
|---|---|
| 45 | 2-{[2-amino-5-formyl-6-(methylamino)pyrimidin-4-yl]thio}-N-[3-(trifluoromethyl)phenyl]acetamide |
| 46 | 2-{[2-amino-5-formyl-6-(methylthio)pyrimidin-4-yl]oxy}-N-[3-(trifluoromethyl)phenyl]acetamide |
| 47 | 2-{[4-amino-6-(methylthio)-1,3,5-triazin-2-yl]oxy}-N-[3-(trifluoromethyl)phenyl]acetamide |
| 48 | 2-{[2-amino-6-(methylthio)pyrimidin-4-yl]thio}-N-[3-(trifluoromethyl)phenyl]acetamide |
| 49 | 2-amino-4-(methylthio)-6-{[2-oxo-2-(3-oxo-3,4-dihydro-2H-1,4-benzoxazin-6-yl)ethyl]thio}pyrimidine-5-carbonitrile |
| 50 | 2-[(2-amino-6-chloro-5-formylpyrimidin-4-yl)oxy]-N-[3-(trifluoromethyl)phenyl]acetamide |
| 51 | 2-{[2-amino-5-formyl-6-(phenylthio)pyrimidin-4-yl]thio}-N-[3-(trifluoromethyl)phenyl]acetamide |

TABLE 1-continued

| Entry | Name | Structure |
|---|---|---|
| 52 | 2-{[2-amino-5-(hydroxymethyl)-6-(phenylthio)pyrimidin-4-yl]thio}-N-[3-(trifluoromethyl)phenyl]acetamide | 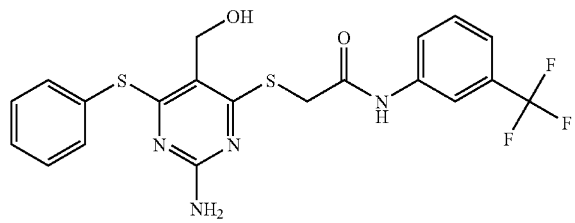 |
| 53 | 2-{[2-amino-5-cyano-6-(methylthio)pyrimidin-4-yl]thio}-N-[2-methyl-3-(trifluoromethyl)phenyl]acetamide | 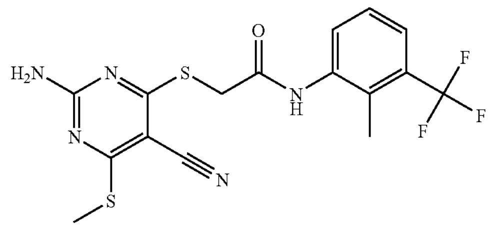 |
| 54 | 2-{[2-amino-5-cyano-6-(methylthio)pyrimidin-4-yl]thio}-N-[2-(methyloxy)-5-(trifluoromethyl)phenyl]acetamide | 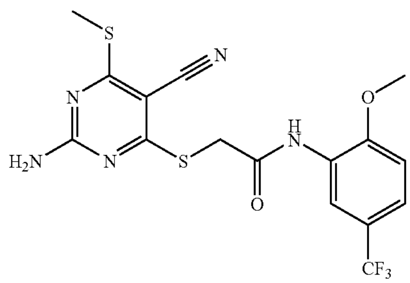 |
| 55 | 2-{[2-amino-5-cyano-6-(methylthio)pyrimidin-4-yl]thio}-N-[2-chloro-5-(trifluoromethyl)phenyl]acetamide | 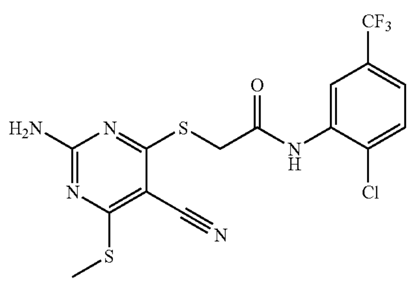 |
| 56 | 2-{[2-amino-5-(hydroxymethyl)-6-(methylthio)pyrimidin-4-yl]oxy}-N-[3-(trifluoromethyl)phenyl]acetamide | 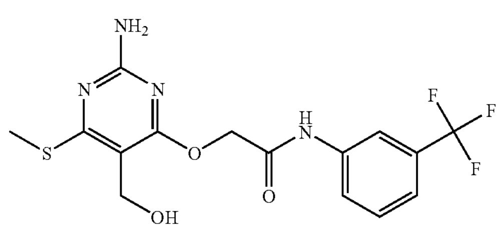 |
| 57 | $N^2$-(6-amino-1H-pyrazolo[3,4-d]pyrimidin-4-yl)-N-[3-(trifluoromethyl)phenyl]glycinamide | 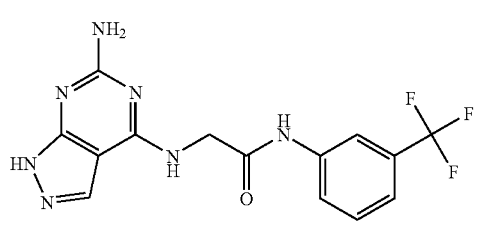 |

TABLE 1-continued

| Entry | Name | Structure |
|---|---|---|
| 58 | N²-[2-amino-5-[(E)-hydrazonomethyl]-6-(methylthio)pyrimidin-4-yl]-N-[3-(trifluoromethyl)phenyl]glycinamide | 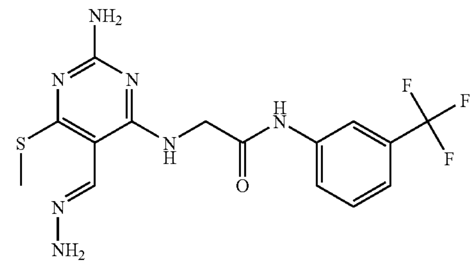 |
| 59 | N²-[2-amino-5-[(E)-(hydroxyimino)methyl]-6-(methylthio)pyrimidin-4-yl]-N-[3-(trifluoromethyl)phenyl]glycinamide | 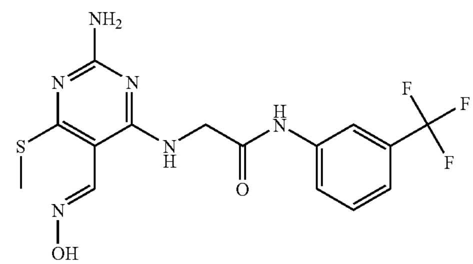 |
| 60 | N²-[2-amino-5-cyano-6-(methylthio)pyrimidin-4-yl]-N-[3-(trifluoromethyl)phenyl]-L-alaninamide | 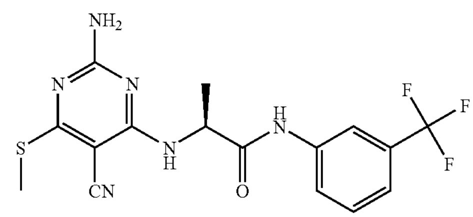 |
| 61 | 2-{[2-amino-5-cyano-6-(methylamino)pyrimidin-4-yl]thio}-N-[3-(trifluoromethyl)phenyl]acetamide | 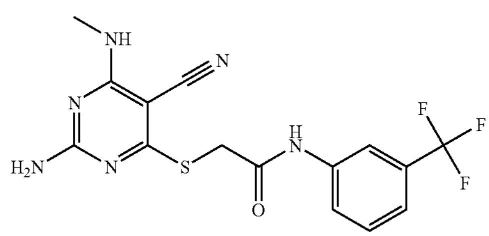 |
| 62 | 2-{[2-amino-5-cyano-6-(methylthio)pyrimidin-4-yl]thio}-N-[2-amino-5-(trifluoromethyl)phenyl]acetamide | 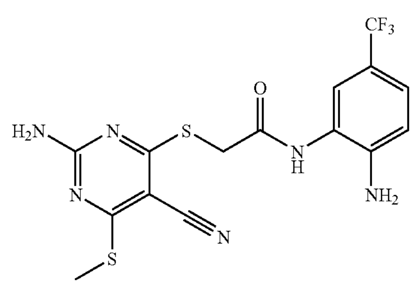 |
| 63 | 2-amino-4-(methylthio)-6-({[6-(trifluoromethyl)-1H-benzimidazol-2-yl]methyl}thio)pyrimidine-5-carbonitrile | 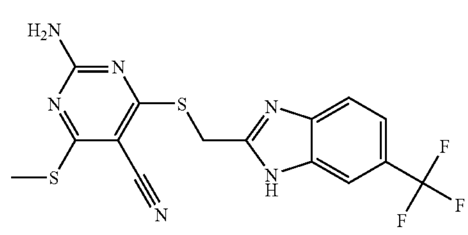 |

TABLE 1-continued

| Entry | Name | Structure |
|---|---|---|
| 64 | 2-[2-amino-5-cyano-6-(methylthio)pyrimidin-4-yl]-N-[3-(trifluoromethyl)phenyl]hydrazine-carboxamide | 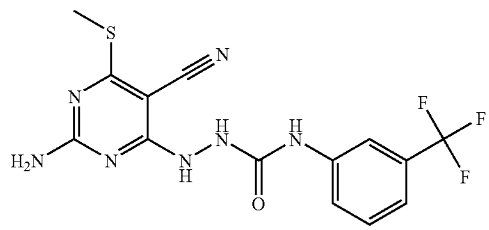 |
| 65 | N²-[5-cyano-2-(methylamino)-6-(methylthio)pyrimidin-4-yl]-N-[3-(trifluoromethyl)phenyl]glycinamide | 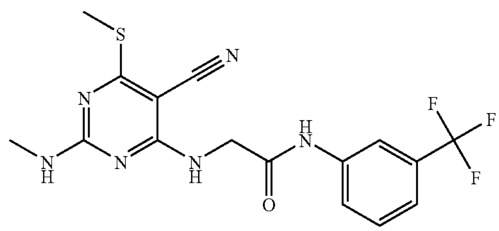 |
| 66 | 2-{[2-amino-5-cyano-6-(dimethylamino)pyrimidin-4-yl]thio}-N-[3-(trifluoromethyl)phenyl]acetamide | 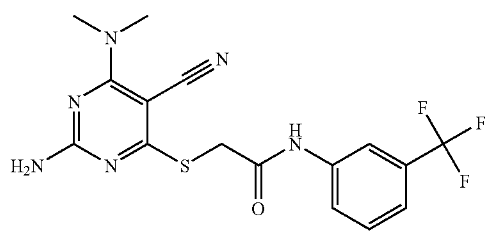 |
| 67 | (S)-1-[2-amino-5-cyano-6-(methylthio)pyrimidin-4-yl]-N-[3-(trifluoromethyl)phenyl]prolinamide | 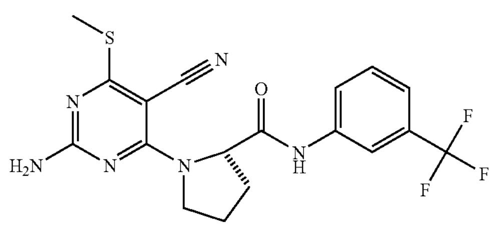 |
| 68 | (2R)-2-{[2-amino-5-cyano-6-(methylthio)pyrimidin-4-yl]oxy}-N-[3-(trifluoromethyl)phenyl]propanamide | 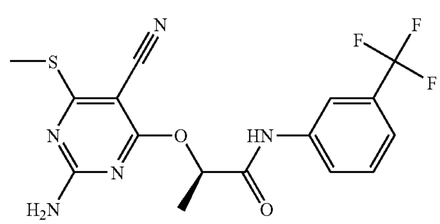 |
| 69 | 1-{[2-amino-5-cyano-6-(methylthio)pyrimidin-4-yl]oxy}-N-[3-(trifluoromethyl)phenyl]cyclopropane carboxamide | 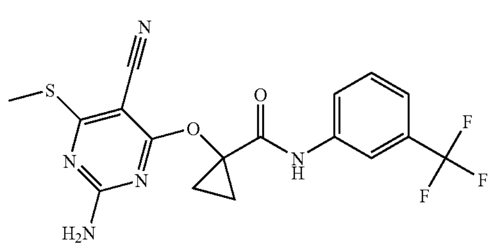 |

TABLE 1-continued

| Entry | Name | Structure |
|---|---|---|
| 70 | (2S)-2-{[2-amino-5-cyano-6-(methylthio)pyrimidin-4-yl]oxy}-3-methyl-N-[3-(trifluoromethyl)phenyl]butanamide | 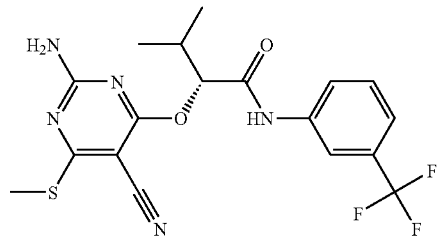 |
| 71 | $N^2$-[5-cyano-2-(dimethylamino)-6-(methylthio)pyrimidin-4-yl]-N-[3-(trifluoromethyl)phenyl]glycinamide | 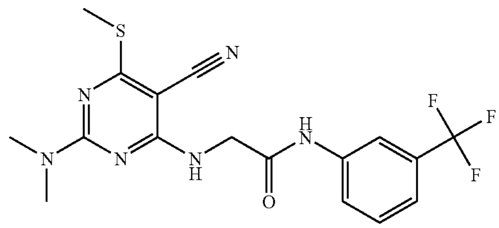 |
| 72 | $N^2$-[2-amino-5-cyano-6-(methylthio)pyrimidin-4-yl]-$N^2$-methyl-N-[3-(trifluoromethyl)phenyl]glycinamide | 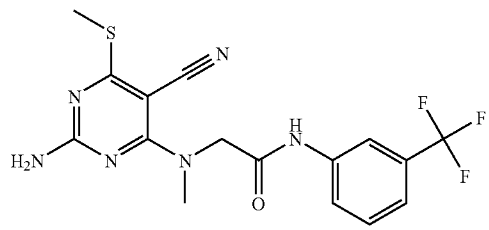 |
| 73 | 1-{[2-amino-5-cyano-6-(methylthio)pyrimidin-4-yl]amino}-N-[3-(trifluoromethyl)phenyl]cyclopropanecarboxamide | 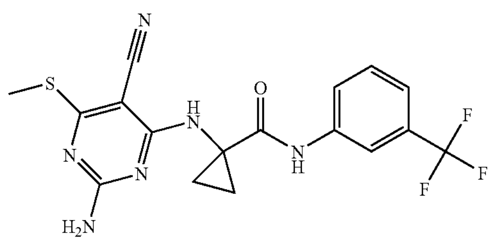 |
| 74 | $N^2$-[2-amino-5-cyano-6-(methylsulfinyl)pyrimidin-4-yl]-N-[3-(trifluoromethyl)phenyl]-L-alaninamide | 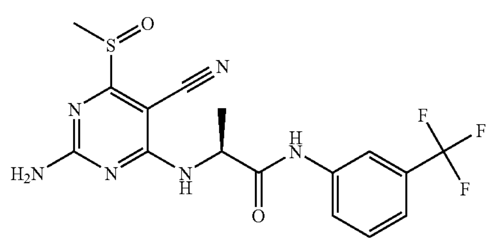 |
| 75 | $N^2$-[2-amino-5-cyano-6-(methylsulfonyl)pyrimidin-4-yl]-N-[3-(trifluoromethyl)phenyl]-L-alaninamide | 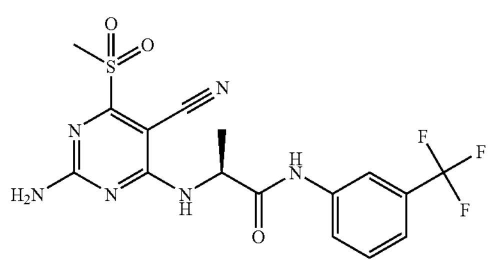 |

TABLE 1-continued

| Entry | Name |
|---|---|
| 76 | N²-(5-cyano-2-morpholin-4-ylpyrimidin-4-yl)-N-[3-(trifluoromethyl)phenyl]glycinamide |
| 77 | 2-{[2-amino-5-cyano-6-(methylthio)pyrimidin-4-yl]thio}-N-[3,5-bis(trifluoromethyl)phenyl]acetamide |
| 78 | N²-[2-amino-5-cyano-6-(methyloxy)pyrimidin-4-yl]-N-[3-(trifluoromethyl)phenyl]-L-alaninamide |
| 79 | N²-[2-amino-5-cyano-6-(methylthio)pyrimidin-4-yl]-N-[2-(methyloxy)-5-(trifluoromethyl)phenyl]-L-alaninamide |
| 80 | N²-[2-amino-5-cyano-6-(methylthio)pyrimidin-4-yl]-N-[2-chloro-5-(trifluoromethyl)phenyl]-L-alaninamide |
| 81 | N²-[2-amino-5-cyano-6-(methylthio)pyrimidin-4-yl]-2-methyl-N-[3-(trifluoromethyl)phenyl]alaninamide |

TABLE 1-continued

| Entry | Name | Structure |
|---|---|---|
| 82 | N²-[2-amino-5-cyano-6-(methylthio)pyrimidin-4-yl]-N-{3-[(4-methylpiperazin-1-yl)carbonyl]phenyl}-L-alaninamide | 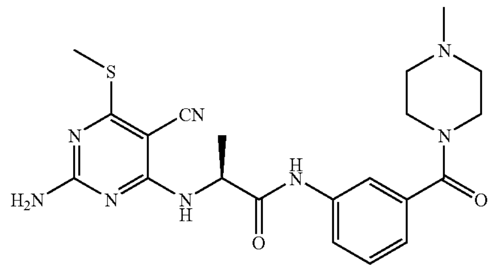 |
| 83 | N²-[2-amino-5-cyano-6-(methylthio)pyrimidin-4-yl]-N-[3-(trifluoromethyl)phenyl]-D-alaninamide | 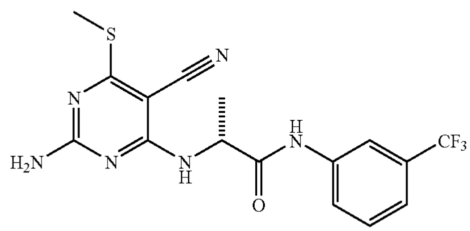 |
| 84 | 2-[(2-amino-5-cyano-6-morpholin-4-ylpyrimidin-4-yl)thio]-N-[3-(trifluoromethyl)phenyl]acetamide | 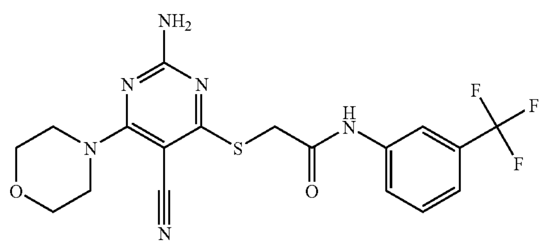 |
| 85 | (R)-1-[2-amino-5-cyano-6-(methylthio)pyrimidin-4-yl]-N-[3-(trifluoromethyl)phenyl]prolinamide | 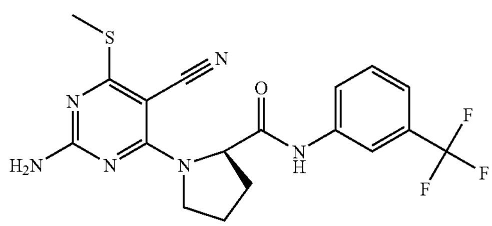 |
| 86 | N²-[2-amino-5-cyano-6-(methylthio)pyrimidin-4-yl]-N-[3-(trifluoromethyl)phenyl]-L-ornithinamide | 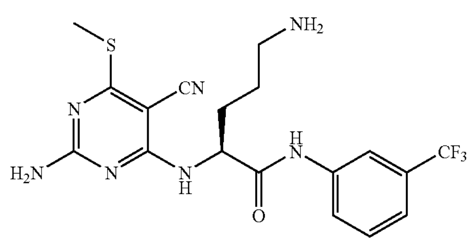 |
| 87 | N²-[2-amino-5-cyano-6-(methylthio)pyrimidin-4-yl]-N-2-[2-(dimethylamino)ethyl]-N-[3-(trifluoromethyl)phenyl]glycinamide | 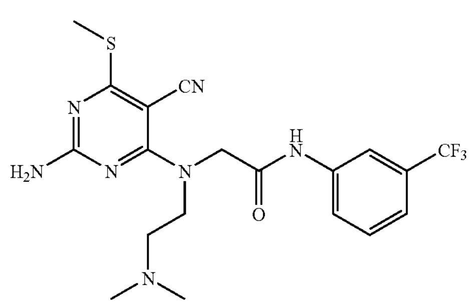 |

TABLE 1-continued

| Entry | Name | Structure |
|---|---|---|
| 88 | N²-[2-amino-5-cyano-6-(ethyloxy)pyrimidin-4-yl]-N-[3-(trifluoromethyl)phenyl]-L-alaninamide | 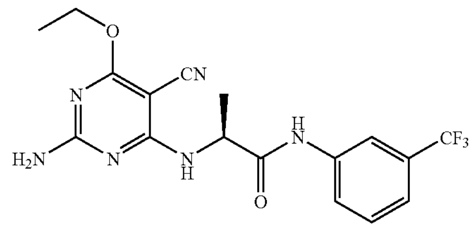 |
| 89 | N²-(2,6-diamino-5-cyanopyrimidin-4-yl)-N-[3-(trifluoromethyl)phenyl]-L-alaninamide | 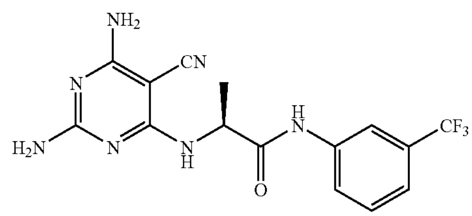 |
| 90 | N²-(2-amino-5-cyanopyrimidin-4-yl)-N-[3-(trifluoromethyl)phenyl]-L-alaninamide | 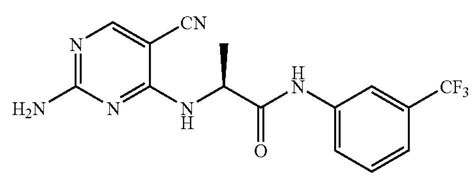 |
| 91 | N²-[2-amino-5-cyano-6-(methylthio)pyrimidin-4-yl]-N-2-methyl-N-[3-(trifluoromethyl)phenyl]-L-alaninamide | 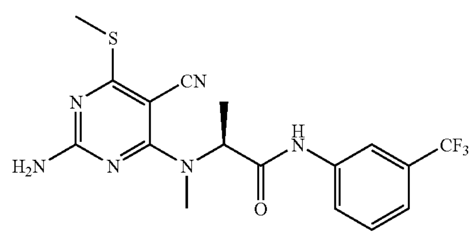 |
| 92 | N²-[2-amino-5-cyano-6-(methyhio)pyrimidin-4-yl]-N-(3-{[2-(diethylamino)ethyl]oxy}phenyl)-L-alaninamide | 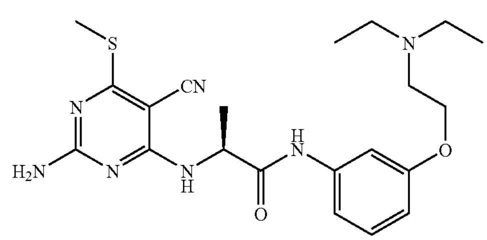 |
| 93 | 2-[2-amino-5-cyano-6-(methylthio)pyrimidin-4-yl]-1,2-dimethyl-N-[3-(trifluoromethyl)phenyl]hydrazinecarboxamide | 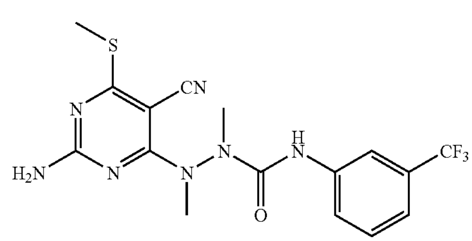 |

TABLE 1-continued

| Entry | Name | Structure |
|---|---|---|
| 94 | $N^2$-[2-amino-5-cyano-6-(methylthio)pyrimidin-4-yl]-N-[3-amino-5-(trifluoromethyl)phenyl]-L-alaninamide | 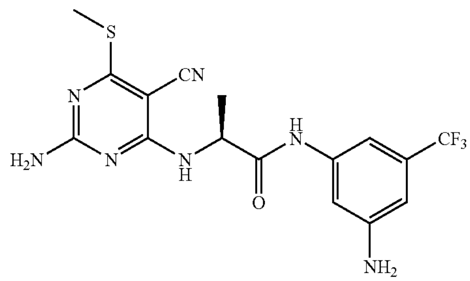 |
| 95 | ethyl [1-[2-amino-5-cyano-6-(methylthio)pyrimidin-4-yl]-2-({[3-(trifluoromethyl)phenyl]amino}carbonyl)hydrazino]acetate | 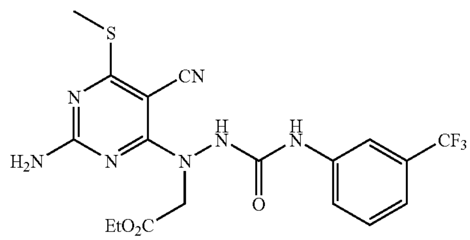 |
| 96 | 2-[2-amino-5-cyano-6-(methylthio)pyrimidin-4-yl]-2-methyl-N-[3-(trifluoromethyl)phenyl]hydrazinecarboxamide | 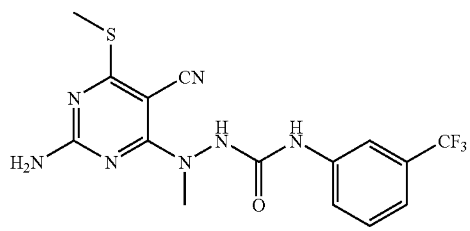 |
| 97 | 3,5-diamino-4,6-dimethyl-N-[3-(trifluoromethyl)phenyl]furo[2,3-b]pyridine-2-carboxamide | 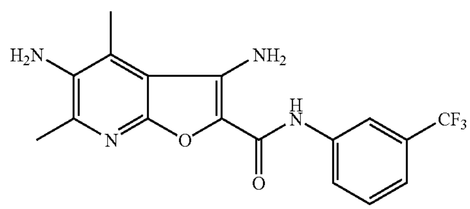 |
| 98 | 3-amino-4,6-dimethyl-5-nitro-N-[3-(trifluoromethyl)phenyl]furo[2,3-b]pyridine-2-carboxamide | 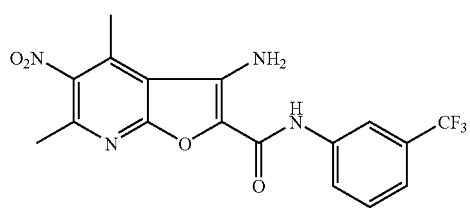 |
| 99 | $N^2$-(2-amino-5-cyano-6-hydroxypyrimidin-4-yl)-N-[3-(trifluoromethyl)phenyl]-L-alaninamide | 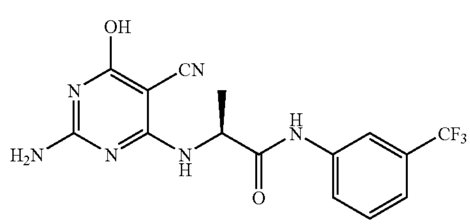 |
| 100 | $N^2$-[5-cyano-2-(methylthio)pyrimidin-4-yl]-N-[3-(trifluoromethyl)phenyl]glycinamide | 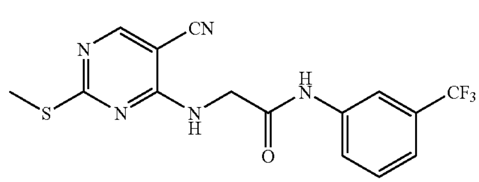 |

TABLE 1-continued

| Entry | Name | Structure |
|---|---|---|
| 101 | $N^2$-[2-amino-5-cyano-6-(methylthio)pyrimidin-4-yl]-N-2-(tetrahydro-2H-pyran-4-ylmethyl)-N-[3-(trifluoromethyl)phenyl]glycinamide | 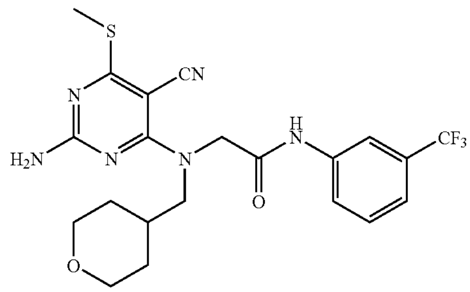 |
| 102 | $N^2$-(2-amino-5-cyano-6-{[2-(dimethylamino)ethyl]oxy}pyrimidin-4-yl)-N-[3-(trifluoromethyl)phenyl]-L-alaninamide | 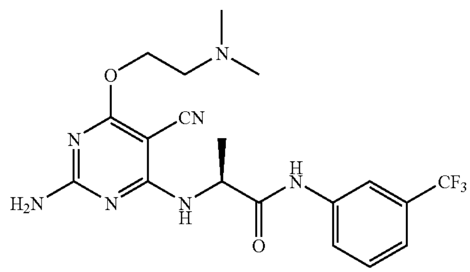 |
| 103 | $N^2$-[2-amino-5-cyano-6-(methylthio)pyrimidin-4-yl]-N-6-{[(1,1-dimethylethyl)oxy]carbonyl}-N-[3-(trifluoromethyl)phenyl]-L-lysinamide | 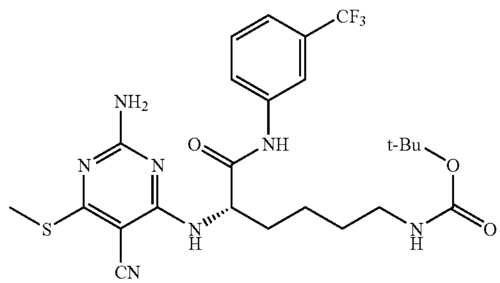 |
| 104 | 2-amino-4-(methylthio)-6-(methyl{(1S)-1-[6-(trifluoromethyl)-1H-benzimidazol-2-yl]ethyl}amino)pyrimidine-5-carbonitrile | 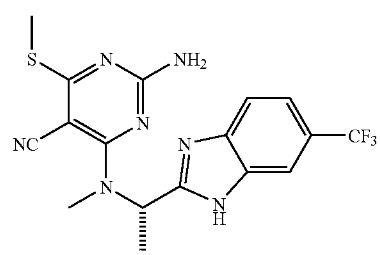 |
| 105 | $N^2$-[2-amino-5-cyano-6-(methylthio)pyrimidin-4-yl]-N-2-[2-(tetrahydro-2H-pyran-4-yl)ethyl]-N-[3-(trifluoromethyl)phenyl]glycinamide | 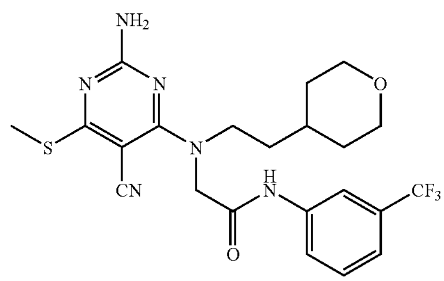 |

TABLE 1-continued

| Entry | Name | Structure |
|---|---|---|
| 106 | N²-[2-amino-5-cyano-6-(methylthio)pyrimidin-4-yl]-N-[3-{[2-(diethylamino)ethyl]amino}-5-(trifluoromethyl)phenyl]-L-alaninamide | 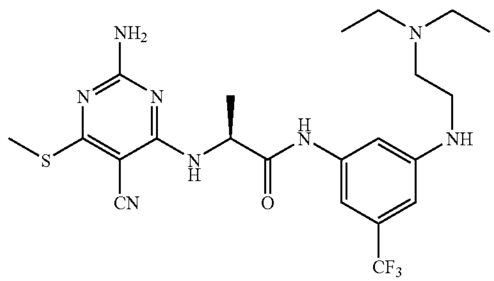 |
| 107 | 2-amino-4-(methylthio)-6-({[(1S)-1-[6-(trifluoromethyl)-1H-benzimidazol-2-yl]ethyl}amino)pyrimidine-5-carbonitrile | 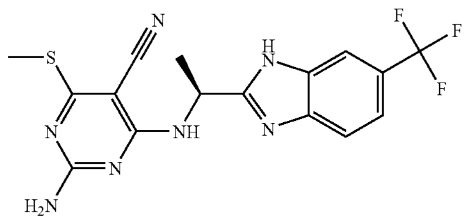 |
| 108 | 2-{2-amino-5-cyano-6-[1-(3-trifluoromethyl-phenylcarbamoyl)-1S-ethylamino]-pyrimidin-4-ylamino}-N-(3-trifluoromethyl-phenyl)-2S-propionamide | 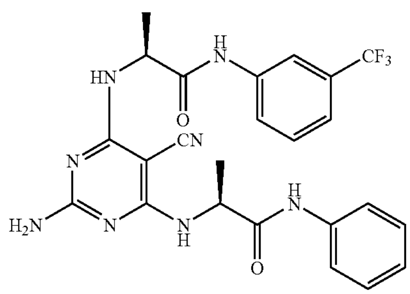 |
| 109 | N²-[2-amino-5-cyano-6-(methylthio)pyrimidin-4-yl]-N-2-methyl-N-(3-methylphenyl)glycinamide | 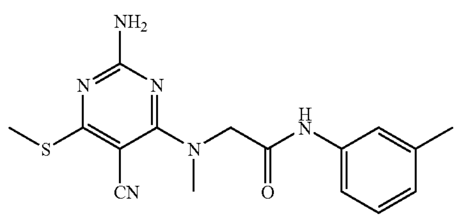 |
| 110 | N²-[2-amino-5-cyano-6-(methylthio)pyrimidin-4-yl]-N-2-methyl-N-[3-(1-methylethyl)phenyl]glycinamide | 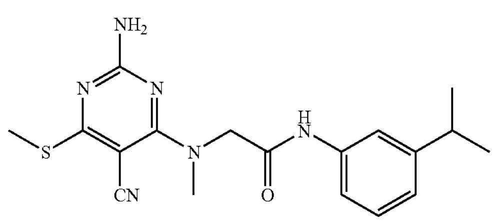 |
| 111 | N²-[2-amino-5-cyano-6-(methylthio)pyrimidin-4-yl]-N-5-[imino(nitroamino)methyl]-N-[3-(trifluoromethyl)phenyl]-L-ornithinamide | 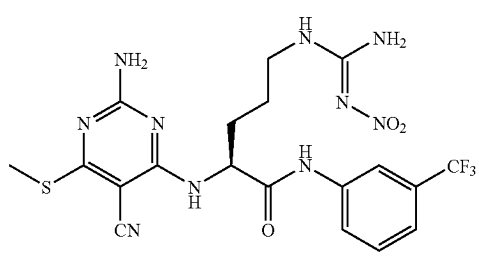 |

TABLE 1-continued

| Entry | Name | Structure |
|---|---|---|
| 112 | methyl 3-({N-[2-amino-5-cyano-6-(methylthio)pyrimidin-4-yl]-L-alanyl}amino)-5-(trifluoromethyl)benzoate | 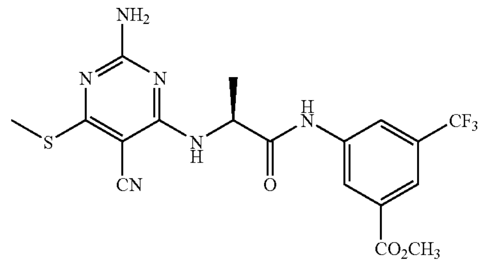 |
| 113 | $N^2$-[2-amino-5-cyano-6-(methylthio)pyrimidin-4-yl]-N-(3-nitrophenyl)-L-alaninamide | 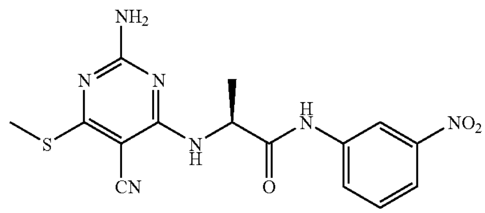 |
| 114 | $N^2$-[2-amino-5-cyano-6-(methylthio)pyrimidin-4-yl]-N-[3-(trifluoromethyl)phenyl]-L-lysinamide | 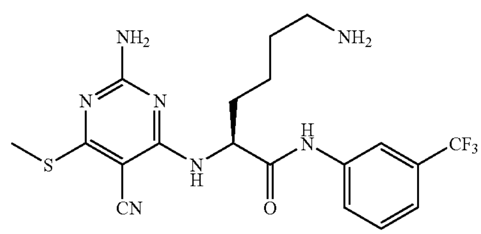 |
| 115 | $N^2$-[2-amino-5-cyano-6-(propyloxy)pyrimidin-4-yl]-N-[3-(trifluoromethyl)phenyl]-L-alaninamide | 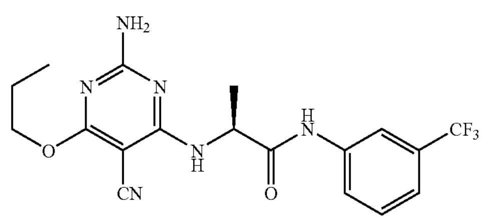 |
| 116 | $N^2$-[5-cyano-2-{[2-(methyloxy)ethyl]amino}-6-(methylthio)pyrimidin-4-yl]-N-[3-(trifluoromethyl)phenyl]-L-alaninamide | 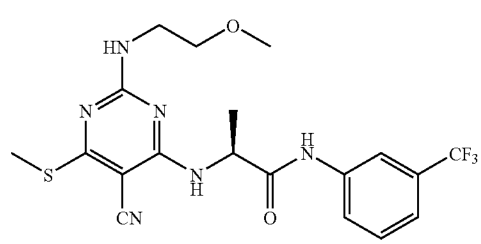 |
| 117 | $N^2$-[2-amino-5-cyano-6-(methylthio)pyrimidin-4-yl]-N-[3-(trifluoromethyl)phenyl]-L-argininamide | 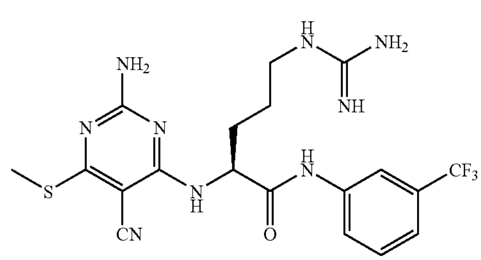 |

TABLE 1-continued

| Entry | Name | Structure |
|---|---|---|
| 118 | N²-[2-amino-5-cyano-6-(methylsulfinyl)pyrimidin-4-yl]-N-2-methyl-N-[3-(trifluoromethyl)phenyl]-L-alaninamide | 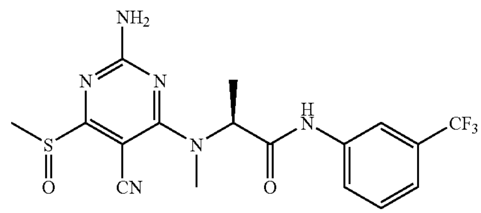 |
| 119 | N²-[2-amino-5-cyano-6-(methyloxy)pyrimidin-4-yl]-N-2-methyl-N-[3-(trifluoromethyl)phenyl]-L-alaninamide | 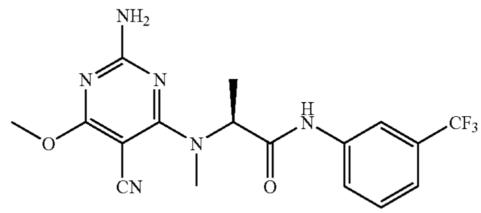 |
| 120 | N²-[2-amino-5-cyano-6-(propyloxy)pyrimidin-4-yl]-N-2-methyl-N-[3-trifluoromethyl)phenyl]-L-alaninamide | 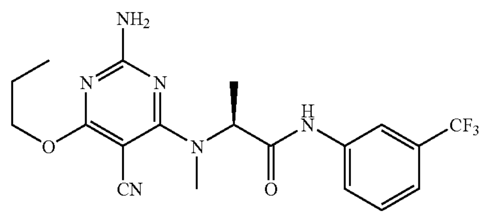 |
| 121 | N²-[2-amino-5-cyano-6-(ethyloxy)pyrimidin-4-yl]-N-2-methyl-N-[3-(trifluoromethyl)phenyl]-L-alaninamide | 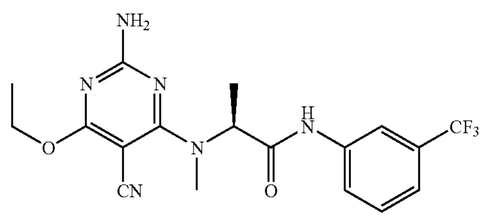 |
| 122 | N²-{2-amino-5-cyano-6-[(1-methylethyl)oxy]pyrimidin-4-yl}-N-[3-(trifluoromethyl)phenyl]-L-alaninamide | 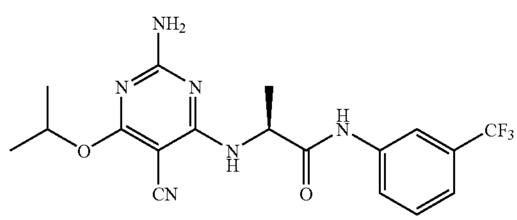 |
| 123 | N⁵-acetyl-N-2-[2-amino-5-cyano-6-(methylthio)pyrimidin-4-yl]-N-[3-(trifluoromethyl)phenyl]-L-ornithinamide | 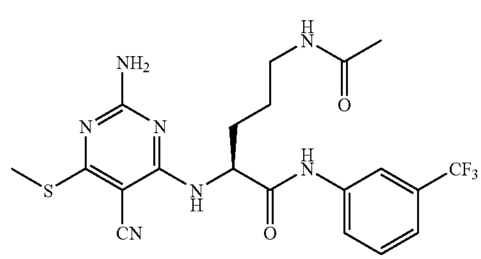 |
| 124 | N²-[2-amino-5-cyano-6-(methylthio)pyrimidin-4-yl]-N-(3-aminophenyl)-L-alaninamide | 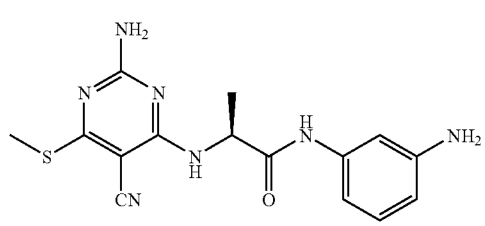 |

TABLE 1-continued

| Entry | Name | Structure |
|---|---|---|
| 125 | 3-({N-[2-amino-5-cyano-6-(methylthio)pyrimidin-4-yl]-L-alanyl}amino)-N-[2-(dimethylamino)ethyl]-5-(trifluoromethyl)benazmide | 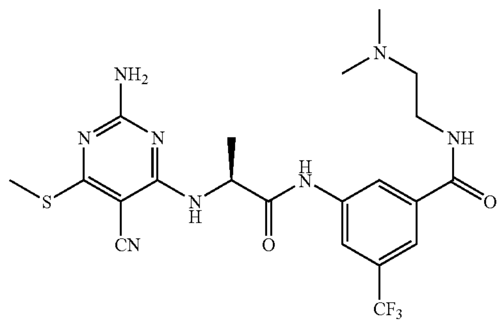 |
| 126 | 2-(methyloxy)ethyl ((4S)-4-{[2-amino-5-cyano-6-(methylthio)pyrimidin-4-yl]amino}-5-oxo-5-{[3-(trifluoromethyl)phenyl]amino}pentyl)carbamate | 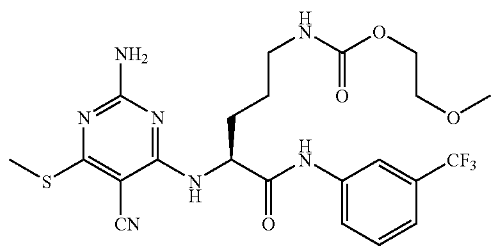 |
| 127 | 2-[2-amino-5-cyano-6-(ethyloxy)pyrimidin-4-yl]-N-[3-(trifluoromethyl)phenyl]hydrazinecarboxamide | 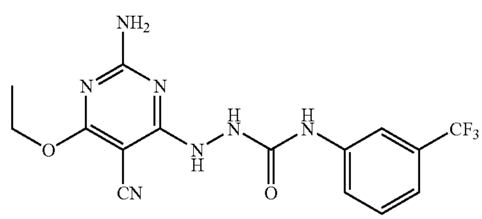 |
| 128 | 1,1-dimethylethyl ((4S)-4-{[2-amino-5-cyano-6-(ethyloxy)pyrimidin-4-yl]amino}-5-oxo-5-{[3-(trifluoromethyl)phenyl]amino}pentyl)carbamate | 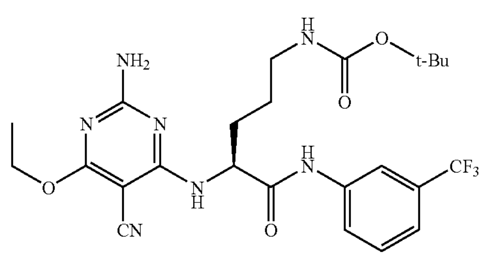 |
| 129 | N-2-[2-amino-5-cyano-6-(ethyloxy)pyrimidin-4-yl]-N-[3-(trifluoromethyl)phenyl]-L-ornithinamide | 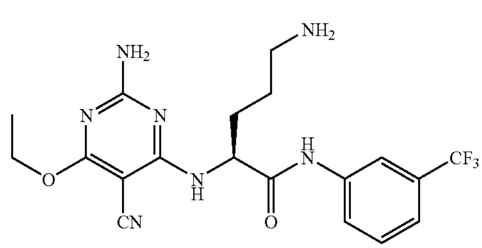 |

TABLE 1-continued

| Entry | Name | Structure |
|---|---|---|
| 130 | 3-({N-[2-amino-5-cyano-6-(methylthio)pyrimidin-4-yl]-N-methyl-L-alanyl}amino)-N-[2-(dimethylamino)ethyl]-5-(trifluoromethyl)benzamide | 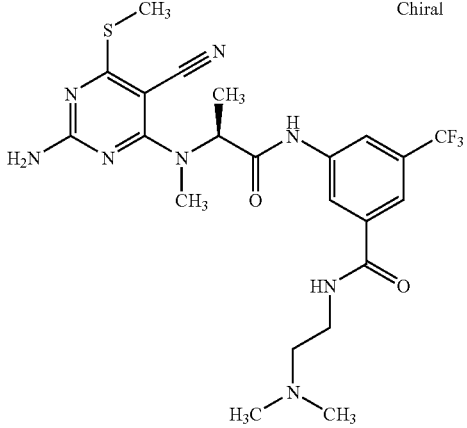 Chiral |
| 131 | 3-({N-[2-amino-5-cyano-6-(methylthio)pyrimidin-4-yl]-N-methyl-L-alanyl}amino)-N-[3-(4-methylpiperazin-1-yl)propyl]-5-(trifluoromethyl)benzamide | 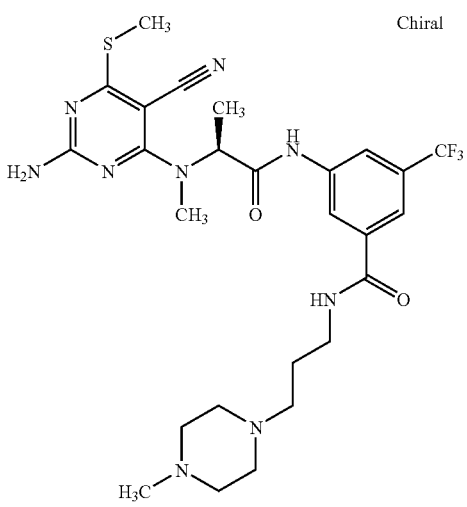 Chiral |
| 132 | $N^2$-[2-amino-5-cyano-6-(methylthio)pyrimidin-4-yl]-N~2~-methyl-N-{3-[(trifluoromethyl)oxy]phenyl}-L-alaninamide | 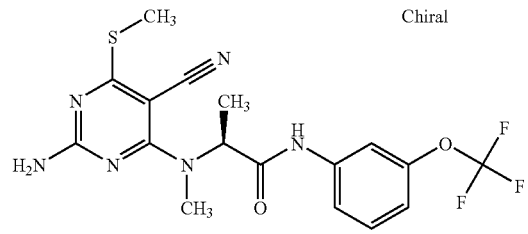 Chiral |
| 133 | $N^2$-[2-amino-5-cyano-6-(methylthio)pyrimidin-4-yl]-N-(3-bromophenyl)-N~2~-methyl-L-alaninamide | 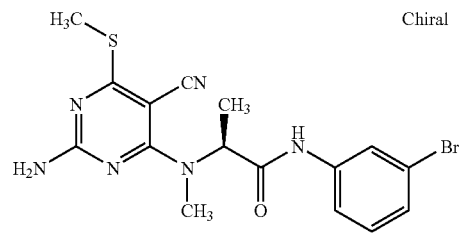 Chiral |

TABLE 1-continued

| Entry | Name | Structure |
|---|---|---|
| 134 | N²-[2-amino-5-cyano-6-(methylthio)pyrimidin-4-yl]-N-{2-{[2-(dimethylamino)ethyl]oxy}-5-[(trifluoromethyl)oxy]phenyl}-N~2~-methyl-L-alaninamide | 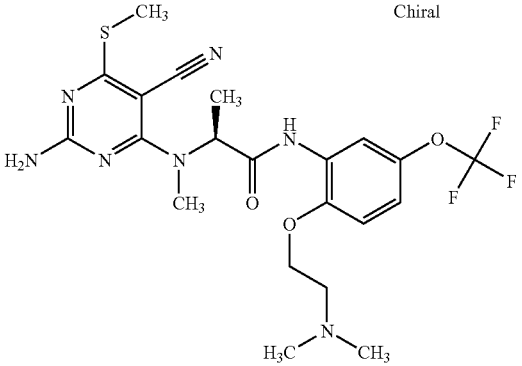 Chiral |
| 135 | 3-({N-[2-amino-5-cyano-6-(methylthio)pyrimidin-4-yl]-N-methyl-L-alanyl}amino)-N-(2-morpholin-4-ylethyl)-5-(trifluoromethyl)benzamide | 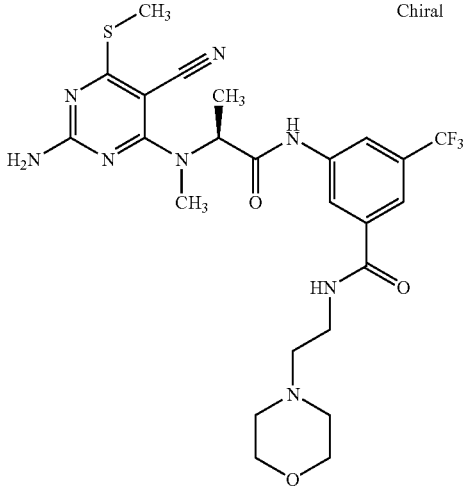 Chiral |
| 136 | N²-[2-amino-5-cyano-6-(ethyloxy)pyrimidin-4-yl]-N~2~-methyl-N-[3-(trifluoromethyl)phenyl]-L-lysinamide | 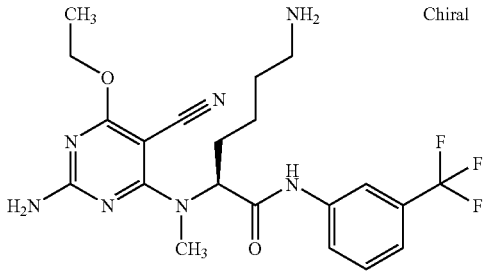 Chiral |
| 137 | N²-[2-amino-5-cyano-6-(methylthio)pyrimidin-4-yl]-N-[3-{[2-(dimethylamino)ethyl]oxy}-5-(trifluoramethyl)phenyl]-L-alaninamide | 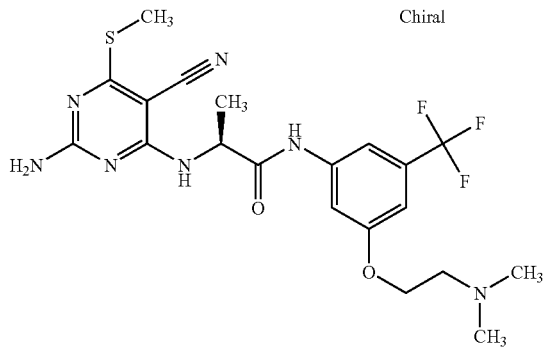 Chiral |

TABLE 1-continued

| Entry | Name | Structure |
|---|---|---|
| 138 | (2S)-2-{[2-amino-5-cyano-6-(methylthio)pyrimidin-4-yl]amino}-3-oxo-3-{[3-(trifluoromethyl)phenyl]amino}propyl acetate | Chiral |
| 139 | $N^2$-[2-amino-5-cyano-6-(methylthio)pyrimidin-4-yl]-N~1~-[3-(trifluoromethyl)phenyl]-L-glutamamide | Chiral |
| 140 | 2-[2-amino-5-cyano-6-(methyloxy)pyrimidin-4-yl]-N-[3-(trifluoromethyl)phenyl]hydrazine-carboxamide | Chiral  lp;.5p |
| 141 | 3-({N-[2-amino-5-cyano-6-(methylthio)pyrimidin-4-yl]-L-alanyl}amino)-N-hydroxy-5-(trifluoromethyl)benzamide | Chiral |
| 142 | $N^2$-[2-amino-5-cyano-6-(methylthio)pyrimidin-4-yl]-3-(dimethylamino)-N-[3-(trifluoromethyl)phenyl]-L-alaninamide | Chiral |

TABLE 1-continued

| Entry | Name | Structure |
|---|---|---|
| 143 | N²-[2-amino-5-cyano-6-(methylthio)pyrimadin-4-yl]-5-morpholin-4-yl-N-[3-(trifluoromethyl)phenyl]-L-norvalinamide | 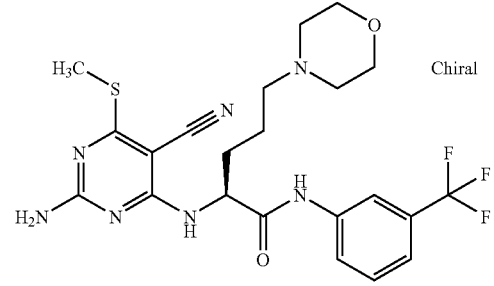 Chiral |
| 144 | N²-[2-amino-5-cyano-6-(methylthio)pyrimidin-4-yl]-N~5~-[2-(methyloxy)ethyl]-N-[3-(trifluoromethyl)phenyl]-L-ornithinamide | 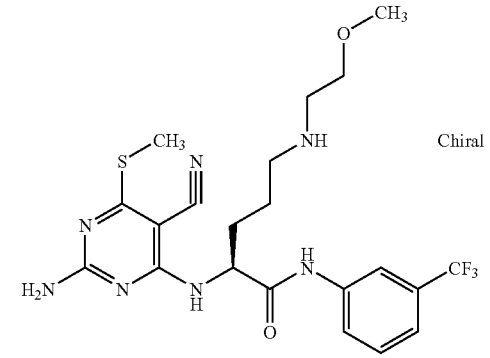 Chiral |
| 145 | 3-({N-[2-amino-5-cyano-6-(methylthio)pyrimidin-4-yl]-L-alanyl}amino)-5-(trifluoromethyl)benzoic acid | 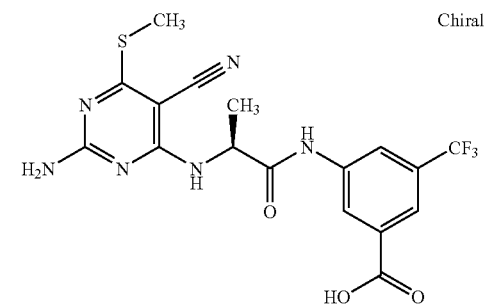 Chiral |
| 146 | methyl N²-[2-amino-5-cyano-6-(methylthio)pyrimidin-4-yl]-N-[3-(trifluoromethyl)phenyl]-L-α-glutaminate | 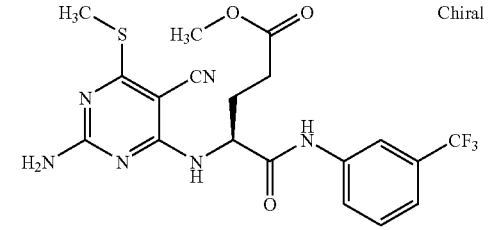 Chiral |
| 147 | N⁵-(aminocarbonyl)-N~2~-[2-amino-5-cyano-6-(methylthio)pyrimidin-4-yl]-N-[3-(trifluoromethyl)phenyl]-L-ornithinamide | 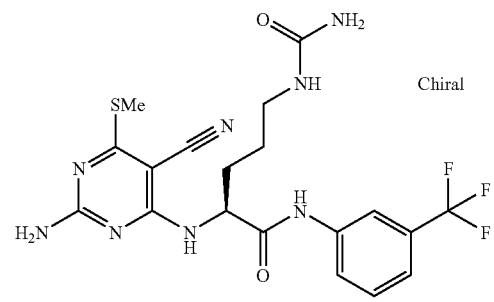 Chiral |

TABLE 1-continued

| Entry | Name | Structure |
|---|---|---|
| 148 | N²-[2-amino-5-cyano-6-(ethyloxy)pyrimidin-4-yl]-N-[3-(trifluoromethyl)phenyl]-L-ornithinamide | 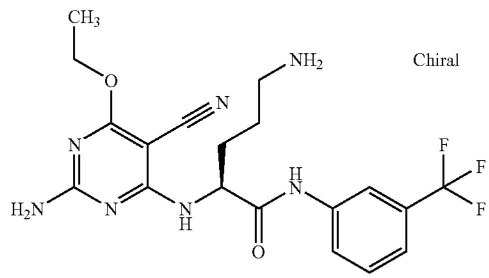 |
| 149 | N²-[2-amino-5-cyano-6-(methylthio)pyrimidin-4-yl]-N-[3-(trifluoromethyl)phenyl]-L-alpha-glutamine | 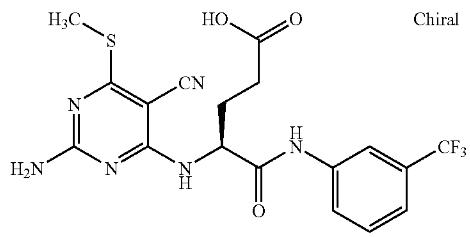 |
| 150 | N²-[2-amino-5-cyano-6-(ethyloxy)pyrimidin-4-yl]-N-[3-(trifluoromethyl)phenyl]-L-serinamide | 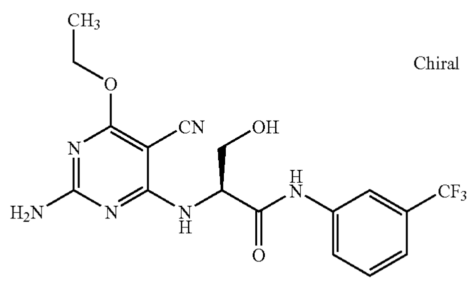 |
| 151 | N²-[2-amino-5-cyano-6-(ethyloxy)pyrimidin-4-yl]-O-(phenylmethyl)-N-[3-(trifluoromethyl)phenyl]-L-serinamide | 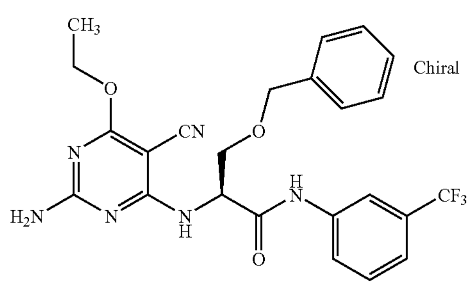 |
| 152 | N²-[2-amino-5-cyano-6-(ethyloxy)pyrimidin-4-yl]-N-[3-(trifluoromethyl)phenyl]-L-argininamide | 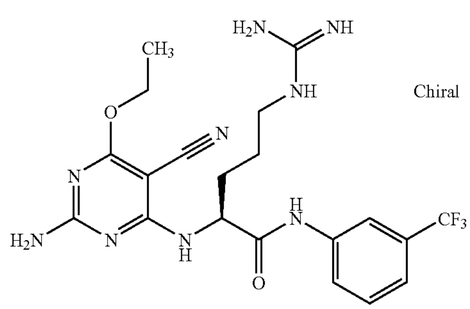 |

TABLE 1-continued

| Entry | Name | Structure |
|---|---|---|
| 153 | N²-[2-amino-5-cyano-6-(methylthio)pyrimidin-4-yl]-N~2~-methyl-N~6~-{[(phenylmethyl)oxy]carbonyl}-N-[3-(trifluoromethyl)phenyl]-L-lysinamide | 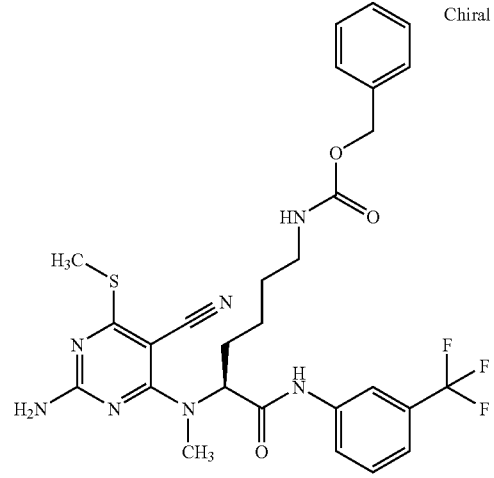 Chiral |
| 154 | Nalpha-[2-amino-5-cyano-6-(ethyloxy)pyrimidin-4-yl]-N-[3-(trifluoromethyl)phenyl]-L-tyrosinamide | 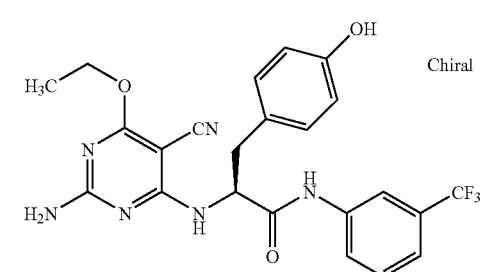 Chiral |
| 155 | N²-[2-amino-5-cyano-6-(methylthio)pyrimidin-4-yl]-N-[3-(trifluoromethyl)phenyl]-L-ornithinamide | 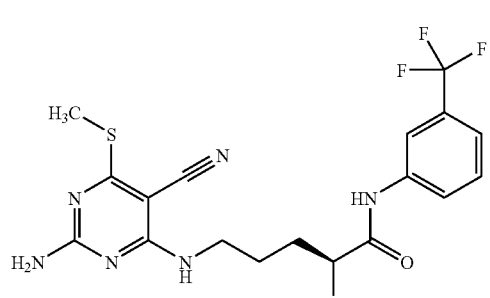 Chiral |
| 156 | N²-[2-amino-5-cyano-6-(ethyloxy)pyrimidin-4-yl]-N~6~,N~6~-dimethyl-N-[3-(trifluoromethyl)phenyl]-L-lysinamide | 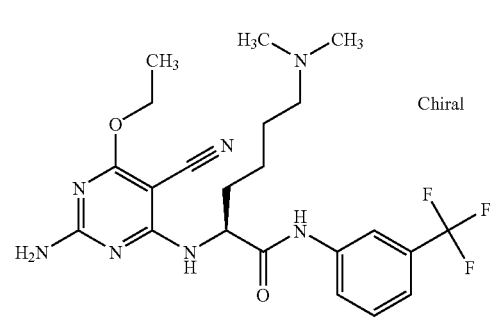 Chiral |

TABLE 1-continued

| Entry | Name | Structure | |
|---|---|---|---|
| 157 | N²-[2-amino-5-cyano-6-(ethyloxy)pyrimidin-4-yl]-N-[3-[(4-methylpiperazin-1-yl)carbonyl]-5-(trifluoromethyl)phenyl]-L-alaninamide | 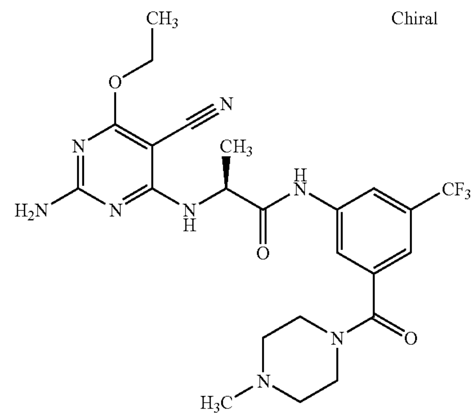 | Chiral |
| 158 | 3-({N-[2-amino-5-cyano-6-(ethyloxy)pyrimidin-4-yl]-L-alanyl}amino)-N-(3-pyrrolidin-1-ylpropyl)-5-(trifluoromethyl)benzamide | 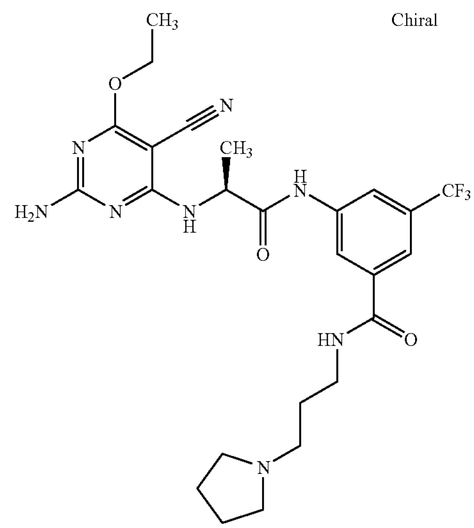 | Chiral |
| 159 | 3-({N-[2-amino-5-cyano-6-(ethyloxy)pyrimidin-4-yl]-L-alanyl}amino)-N-(2-morpholin-4-ylethyl)-5-(trifluoromethyl)benzamide | 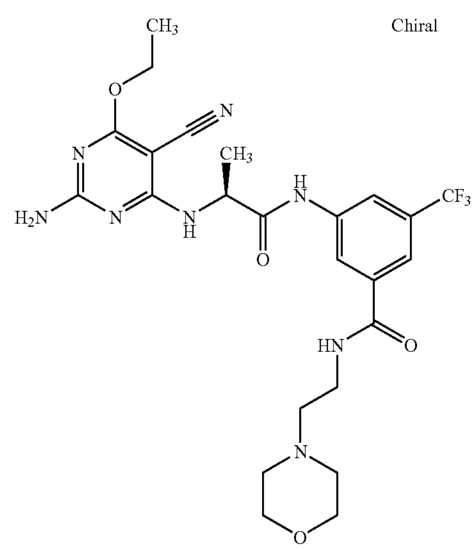 | Chiral |

TABLE 1-continued

| Entry | Name | Structure | |
|---|---|---|---|
| 160 | 3-({N-[2-amino-5-cyano-6-(ethyloxy)pyrimidin-4-yl]-L-alanyl}amino)-N-[2-(dimethylamino)ethyl]-5-(trifluoromethyl)benzamide | 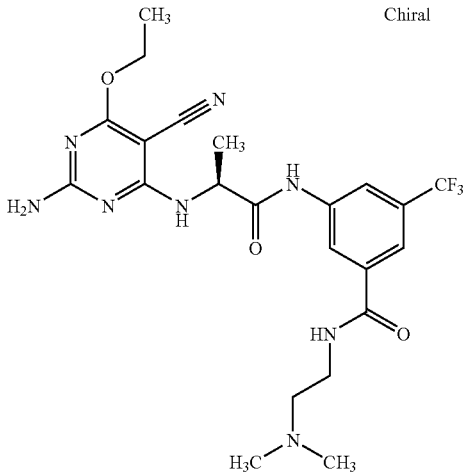 | Chiral |
| 161 | 3-({N-[2-amino-5-cyano-6-(ethyloxy)pyrimidin-4-yl]-L-alanyl}amino)-N-[3-(4-methylpiperazin-1-yl)propyl]-5-(trifluoromethyl)benzamide | 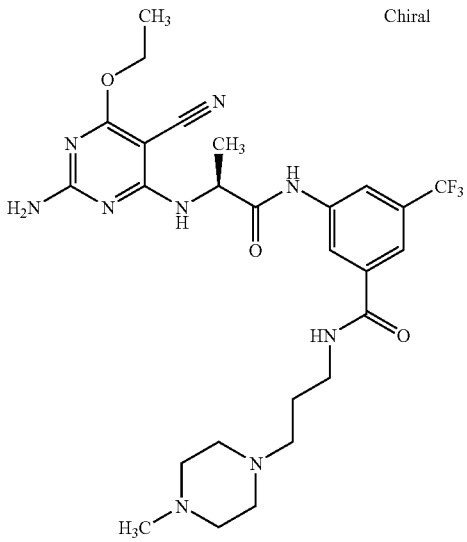 | Chiral |
| 162 | $N^2$-[2-amino-5-cyano-6-(ethyloxy)pyrimidin-4-yl]-N~2~-methyl-N~6~-{[(phenylmethyl)oxy]carbonyl}-N-[3-(trifluoromethyl)phenyl]-L-lysinamide | 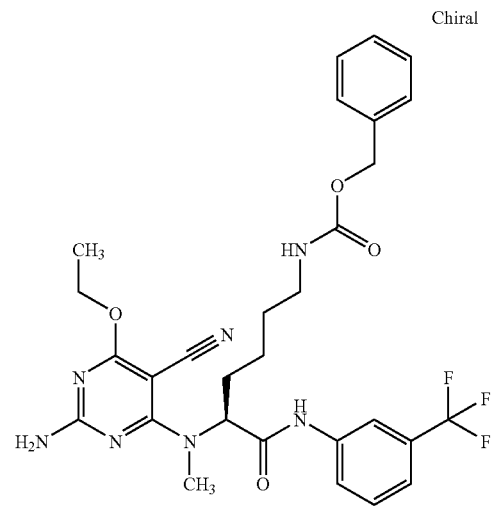 | Chiral |

TABLE 1-continued

| Entry | Name | Structure |
|---|---|---|
| 163 | 1,1-dimethylethyl ((4S)-4-{[2-amino-5-cyano-6-(ethyloxy)pyrimidin-4-yl]amino}-5-oxo-5-{[3-(trifluoromethyl)phenyl]amino}pentyl) carbamate | Chiral |
| 164 | (2S)-2-{[2-amino-5-cyano-6-(ethyloxy)pyrimidin-4-yl]amino}-3-oxo-3-{[3-(trifluoromethyl)phenyl]amino} propyl acetate | Chiral |
| 165 | phenylmethyl $N^2$-[2-amino-5-cyano-6-(ethyloxy)pyrimidin-4-yl]-N-[3-(trifluoromethyl)phenyl]-L-alpha-glutaminate | Chiral |
| 166 | $N^2,N^5$-diacetyl-N~2~-[2-(acetylamino)-5-cyano-6-(methylthio)pyrimidin-4-yl]-N-[3-(trifluoromethyl)phenyl]-L-ornithinamide | Chiral |

TABLE 1-continued

| Entry | Name | Structure | |
|---|---|---|---|
| 167 | 2-(methyloxy)ethyl ((4S)-4-{[2-amino-5-cyano-6-(methylthio)pyrimidin-4-yl]amino}-5-oxo-5-{[3-(trifluoromethyl)phenyl]amino}pentyl) carbamate | 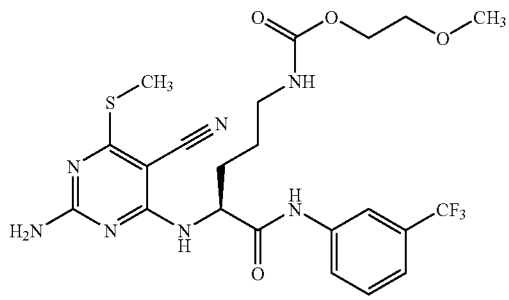 | Chiral |
| 168 | $N^2$-[2-amino-5-cyano-6-(ethyloxy)pyrimidin-4-yl]-5-morpholin-4-yl-N-[3-(trifluoromethyl)phenyl]-L-norvalinamide | 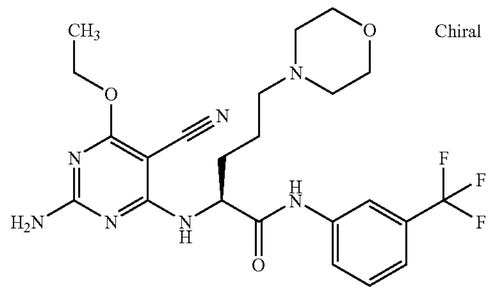 | Chiral |
| 169 | N-((4S)-4-{[2-amino-5-cyano-6-(ethyloxy)pyrimidin-4-yl]amino}-5-oxo-5-{[3-(trifluoromethyl)phenyl]amino}pentyl)-N,N-dimethylmethanaminium | 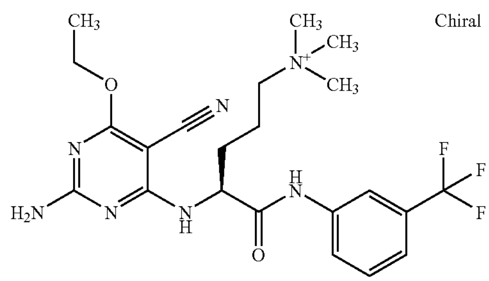 | Chiral |
| 170 | Methyl $N^2$-[2-amino-5-cyano-6-(ethyloxy)pyrimidin-4-yl]-N-[3-(trifluoromethyl)phenyl]-L-alpha-glutaminate | 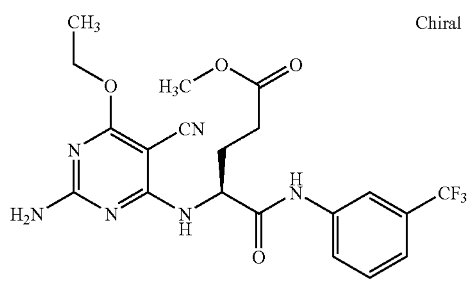 | Chiral |
| 171 | $N^2$-[2-amino-5-cyano-6-(methylthio)pyrimidin-4-yl]-N~6~,N~6~-dimethyl-N-[3-(trifluoromethyl)phenyl]-L-lysinamide | 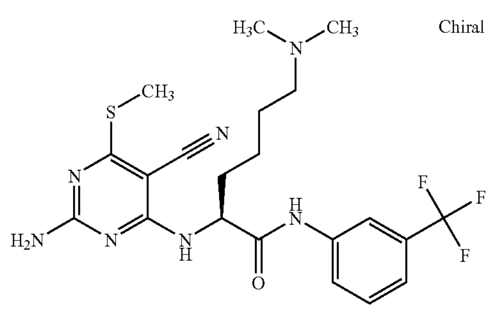 | Chiral |

TABLE 1-continued

| Entry | Name | Structure |
|---|---|---|
| 172 | N²-[2-amino-5-cyano-6-(ethyloxy)pyrimidin-4-yl]-N~2~-methyl-N-{3-[(trifluoromethyl)oxy]phenyl}-L-alaninamide | Chiral |
| 173 | N²-[2-amino-5-cyano-6-(ethyloxy)pyrimidin-4-yl]-N-[3-(trifluoromethyl)phenyl]-L-alpha-glutamine | Chiral |
| 174 | N²-[2-amino-5-cyano-6-(ethyloxy)pyrimidin-4-yl]-N-(3-bromophenyl)-N~2~-methyl-L-alaninamide | Chiral |
| 175 | N²-[2-amino-5-cyano-6-(ethyloxy)pyrimidin-4-yl]-N~1~-[3-(trifluoromethyl)phenyl]-L-glutamamide | Chiral |
| 176 | N²-[2-amino-5-cyano-6-(ethyloxy)pyrimidin-4-yl]-3-(dimethylamino)-N-[3-(trifluoromethyl)phenyl]-L-alaninamide | Chiral |

TABLE 1-continued

| Entry | Name | Structure | |
|---|---|---|---|
| 177 | '2-(2-amino-5-cyano-6-ethoxy-pyrimidin-4-ylamino)-4-hydrazinocarbonyl-N-(3-trifluoromethyl-phenyl)-butyramide | 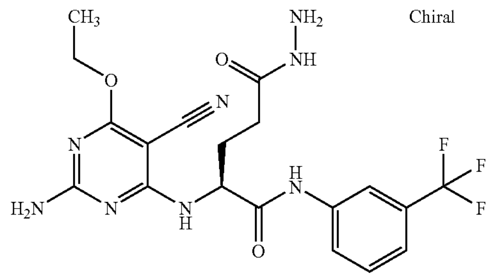 | Chiral |
| 178 | N²-[2-amino-5-cyano-6-(methyloxy)pyrimidin-4-yl]-3-(dimethylamino)-N-[3-(trifluoromethyl)phenyl]-L-alaninamide | 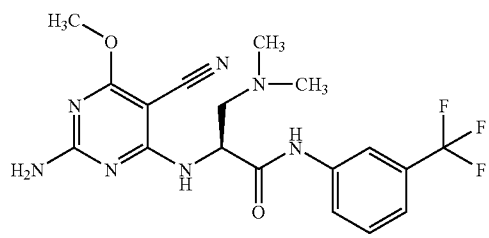 | Chiral |
| 179 | N²-[2-amino-5-cyano-6-(methyloxy)pyrimidin-4-yl]N-[3-{[2-(dimethylamino)ethyl]oxy}-5-(trifluoromethyl)phenyl]-L-alaninamide | 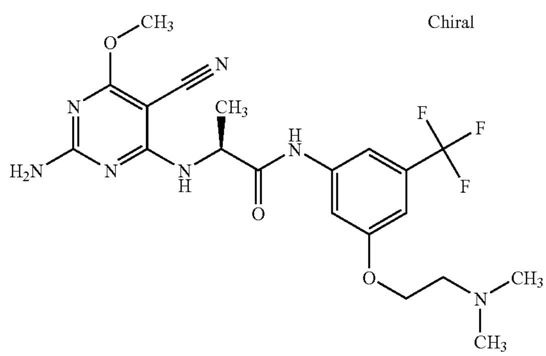 | Chiral |
| 180 | N²-[2-amino-5-cyano-6-(ethyloxy)pyrimidin-4-yl]-N-[3-{[2-(dimethylamino)ethyl]oxy}-5-(trifluoromethyl)phenyl]-L-alaninamide | 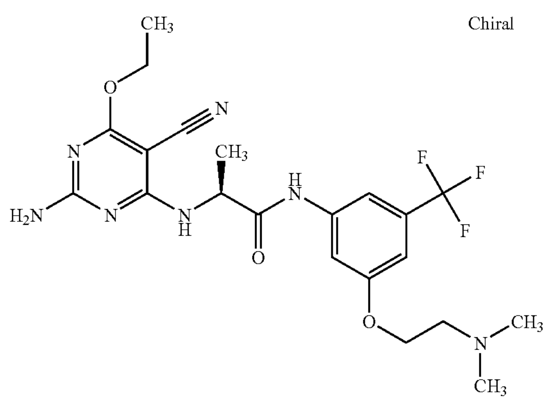 | Chiral |
| 181 | N²-[2-amino-5-cyano-6-(methyloxy)pyrimidin-4-yl]-N-(3-bromophenyl)-N~2~-methyl-L-alaninamide | 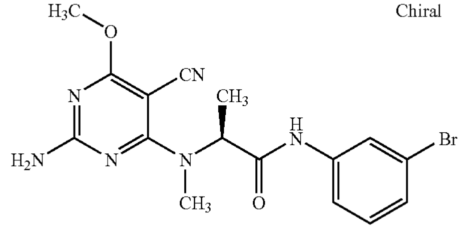 | Chiral |

TABLE 1-continued

| Entry | Name | Structure |
|---|---|---|
| 182 | phenylmethyl N²-[2-amino-5-cyano-6-(methylthio)pyrimidin-4-yl]-N-[3-(trifluoromethyl)phenyl]-L-alpha-glutaminate | 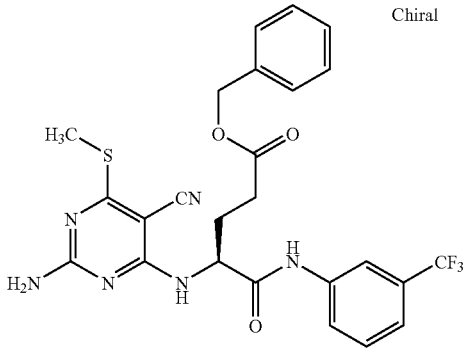 Chiral |
| 183 | N²-[2-amino-5-cyano-6-(methylthio)pyrimidin-4-yl]-O-(phenylmethyl)-N-[3-(trifluoromethyl)phenyl]-L-serinamide | 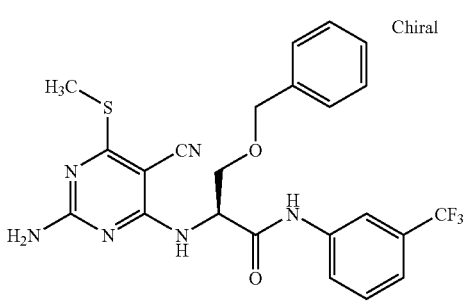 Chiral |
| 184 | N²-[2-amino-5-cyano-6-(methylthio)pyrimidin-4-yl]-N~5~,N~5~-bis[2-(methyloxy)ethyl]-N-[3-(trifluoromethyl)phenyl]-L-ornithinamide | 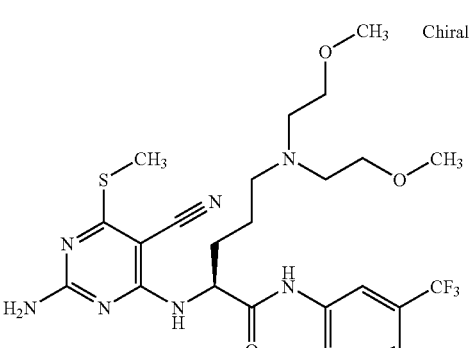 Chiral |
| 185 | 1,1-dimethylethyl ((4S)-4-{[2-amino-5-cyano-6-(methyloxy)pyrimldin-4-yl]amino}-5-oxo-5-{[3-(trifluoromethyl)phenyl]amino}pentyl)carbamate | 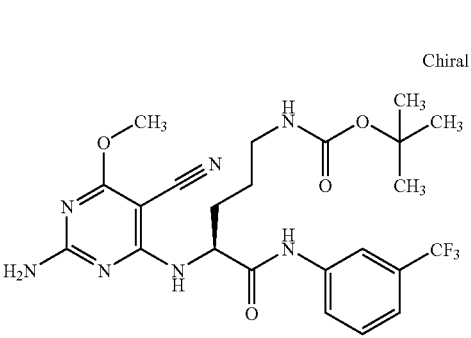 Chiral |

TABLE 1-continued

| Entry | Name | Structure |
|---|---|---|
| 186 | N[5]-acetyl-N[2]-[2-amino-5-cyano-6-(ethyloxy)pyrimidin-4-yl]-N-[3-(trifluoromethyl)phenyl]-L-ornithinamide | 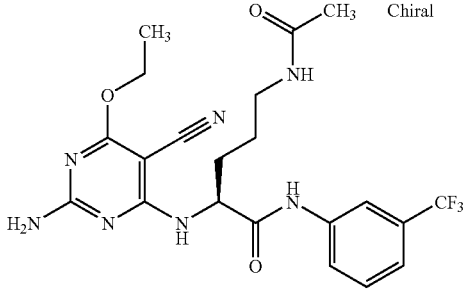 |
| 187 | N[5]-acetyl-N[2]-[2-amino-5-cyano-6-(methylthio)pyrimidin-4-yl]-N-[3-(trifluoromethyl)phenyl]-L-ornithinamide | 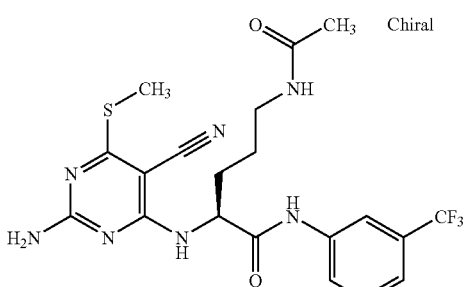 |
| 188 | N[2]-[2-amino-5-cyano-6-(methyloxy)pyrimidin-4-yl]-N~2~-methyl-N-{3-[(trifluoromethyl)oxy]phenyl}-L-alaninamide | 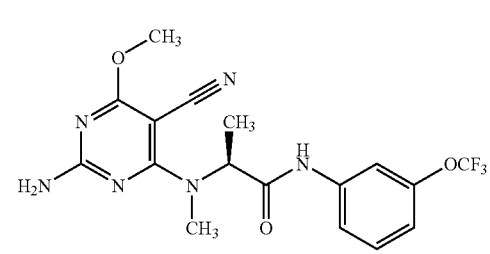 |
| 189 | methyl 3-({N-[2-amino-5-cyano-6-(methyloxy)pyrimidin-4-yl]-L-alanyl}amino)-5-(trifluoromethyl)benzoate | 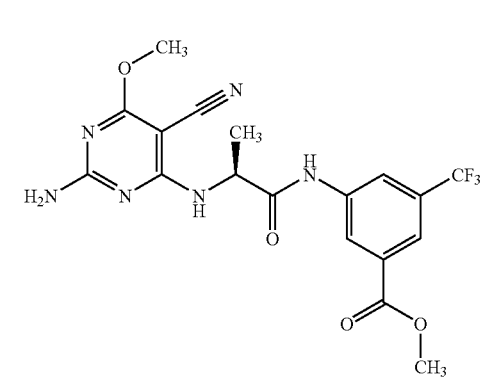 |

TABLE 1-continued

| Entry | Name | Structure | |
|---|---|---|---|
| 190 | 3-({N-[2-amino-5-cyano-6-(methyloxy)pyrimidin-4-yl]-L-alanyl}amino)-N-[2-(dimethylamino)ethyl]-5-(trifluoromethyl)benzamide | 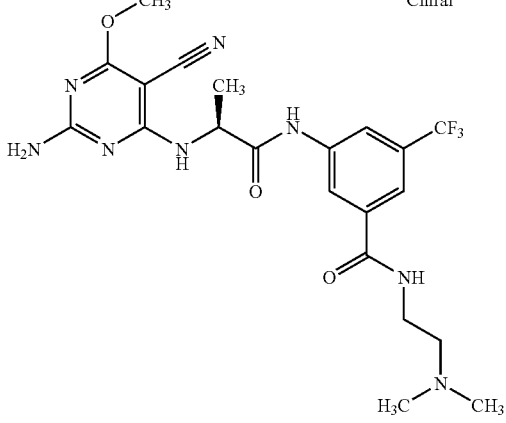 | Chiral |
| 191 | $N^2$-[2-amino-5-cyano-6-(methylthio)pyrimidin-4-yl]-3-morpholin-4-yl-N-[3-(trifluoromethyl)phenyl]-L-alaninamide | 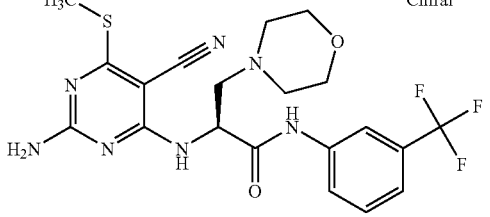 | Chiral |
| 192 | $N^2$-[2-amino-5-cyano-6-(methyloxy)pyrimidin-4-yl]-3-morpholin-4-yl-N-[3-(trifluoromethyl)phenyl]-L-alaninamide | 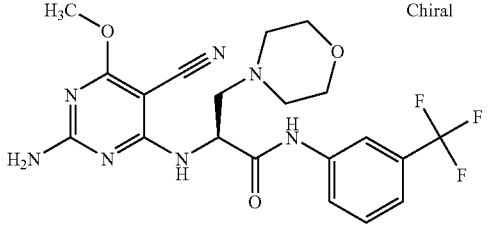 | Chiral |
| 193 | $N^2$-[2-amino-5-cyano-6-(ethyloxy)pyrimidin-4-yl]-3-morpholin-4-yl-N-[3-(trifluoromethyl)phenyl]-L-alaninamide | 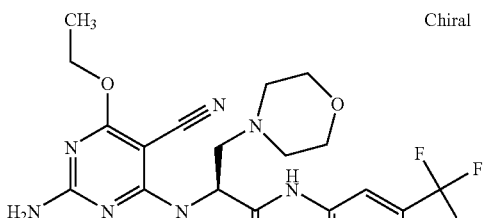 | Chiral |
| 194 | $N^5$-(aminocarbonyl)-$N^2$-[2-amino-5-cyano-6-(ethyloxy)pyrimidin-4-yl]-N-[3-(trifluoromethyl)phenyl]-L-ornithinamide | 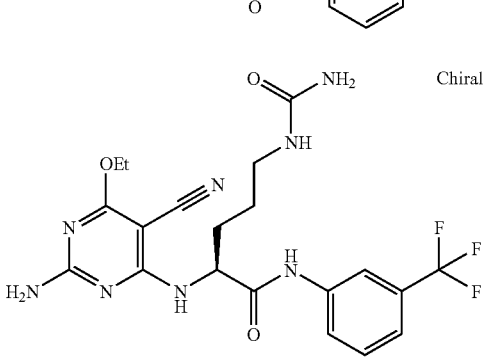 | Chiral |

TABLE 1-continued

| Entry | Name | Structure |
|---|---|---|
| 195 | N²-[2-amino-5-cyano-6-(methylthio)pyrimidin-4-yl]-N-[3-(trifluoromethyl)phenyl]-D-lysinamide | Chiral |
| 196 | N²-[2-amino-5-cyano-6-(ethyloxy)pyrimidin-4-yl]-N-[3-(trifluoromethyl)phenyl]-D-lysinamide | Chiral |
| 197 | N²-[2-amino-5-cyano-6-(ethyloxy)pyrimidin-4-yl]-O-methyl-N-[3-(trifluoromethyl)phenyl]-L-serinamide | Chiral |
| 198 | N²-[2-amino-5-cyano-6-(methylthio)pyrimidin-4-yl]-N~5~-(methylsulfonyl)-N-[3-(trifluoromethyl)phenyl]-L-ornithinamide | Chiral |

Embodiment [0055]:

Another aspect of the invention is a pharmaceutical composition comprising the compound according to any one of Embodiments [0022]-[0055] and a pharmaceutically acceptable carrier.

Embodiment [0057]:

Another aspect of the invention is a metabolite of the compound or the pharmaceutical composition according to any one of Embodiments [0022]-[0056].

Embodiment [0058]:

Another aspect of the invention is a method of modulating the in vivo activity of a kinase, the method comprising administering to a subject an effective amount of a composition comprising at least one of: the compound according to any of Embodiments [0022]-[0055], the pharmaceutical composition according to Embodiment [0056], a compound explicitly provided against in Embodiment [0022] or [0042], and a pharmaceutical composition comprising a compound, the composition of which was, explicitly provided against in Embodiment [0022] or and a pharmaceutically acceptable carrier.

Embodiment [0059]:

Another aspect of the invention is the method according to Embodiment [0058], wherein the kinase is p70S6K.

Embodiment [0060]:

Another aspect of the invention is the method according to Embodiment [0059], wherein modulating the in vivo activity of p70S6K comprises inhibition of p70S6K.

Embodiment [0061]:

Another aspect of the invention is a method of treating diseases or disorders associated with uncontrolled, abnormal, and/or unwanted cellular activities, the method comprising administering, to a mammal in need thereof, a therapeutically effective amount of a composition comprising at least one of: the compound according to any of paragraphs, the pharmaceutical composition according to Embodiment [0056], a compound, the composition of which was, explicitly provided against in Embodiment [0022] or [0042], and a pharmaceutical composition comprising a compound, the composition of which was, explicitly provided against in Embodiment [0022] or [0042] and a pharmaceutically acceptable carrier.

Embodiment [0062]:

Another aspect of the invention is a method of screening for modulator of a p70S6K kinase, the method comprising combining either a compound according to any one of Embodiments [0022]-[0055] or a compound, the composition of which was, explicitly provided against in Embodiment [0022] or [0042], and at least one candidate agent and determining the effect of the candidate agent on the activity of said kinase.

Embodiment [0063]:

Another aspect of the invention is a method of inhibiting proliferative activity in a cell, the method comprising administering an effective amount of: the compound according to any of paragraphs, the pharmaceutical composition according to Embodiment [0056], a compound, the composition of which was, explicitly provided against in Embodiment [0022] or and a pharmaceutical composition comprising a compound, the composition of which was, explicitly provided against in Embodiment [0022] or [0042] and a pharmaceutically acceptable carrier.

Embodiment [0064]:

Another aspect of the invention is a method of inhibiting abnormal metabolic activity in a cell, the method comprising administering an effective amount of: the compound according to any of Embodiments [0022]-[0055], the pharmaceutical composition according to Embodiment [0056], a compound, the composition of which was, explicitly provided against in Embodiment [0022] or [0042], and a pharmaceutical composition comprising a compound, the composition of which was, explicitly provided against in Embodiment [0022] or [0043] and a pharmaceutically acceptable carrier.

Definitions

As used in the present specification, the following words and phrases are generally intended to have the meanings as set forth below, except to the extent that the context in which they are used indicates otherwise or they are expressly defined to mean something different.

The symbol "—" means a single bond, "═" means a double bond, "≡" means a triple bond. The symbol "〜" refers to a group on a double-bond as occupying either position on the terminus of a double bond to which the symbol is attached; that is, the geometry, E- or Z-, of the double bond is ambiguous. When a group is depicted removed from its parent formula, the "~" symbol will be used at the end of the bond which was theoretically cleaved in order to separate the group from its parent structural formula.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

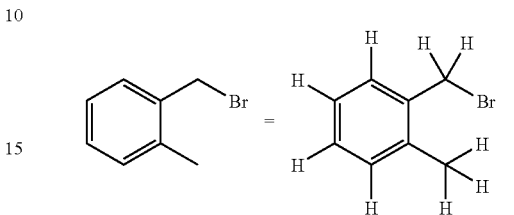

In this application, some ring structures are depicted generically and will be described textually. For example, in the schematic below, if in the structure on the left, ring A is used to describe a "spirocyclyl," then if ring A is cyclopropyl, there are at most four hydrogens on ring A (when "R" can also be —H). In another example, as depicted on the right side of the schematic below, if ring B is used to describe a "phenylene" then there can be at most four hydrogens on ring B (assuming depicted cleaved bonds are not C—H bonds).

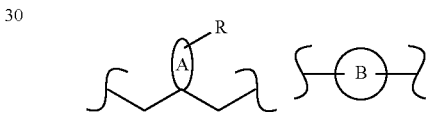

If a group "R" is depicted as "floating" on a ring system, as for example in the formula:

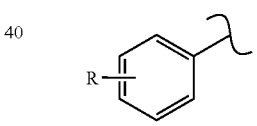

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

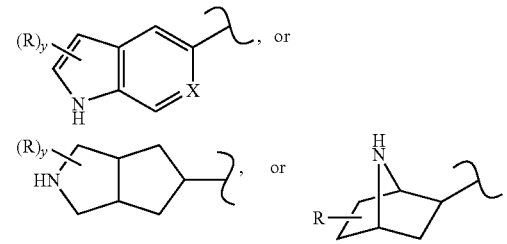

then, unless otherwise defined, a substituent "R" may reside on any atom of the fused ring system, assuming replacement of a depicted hydrogen (for example the —NH— in the formula above), implied hydrogen (for example as in the formula above, where the hydrogens are not shown but understood to be present), or expressly defined hydrogen (for example where in the formula above, "X" equals =CH—) from one of the ring atoms, so long as a stable structure is formed. In the example depicted, the "R" group may reside on either the 5-membered or the 6-membered ring of the fused ring system. In the formula depicted above, when y is 2 for example, then the two "R's" may reside on any two atoms of the ring system, again assuming each replaces a depicted, implied, or expressly defined hydrogen on the ring.

When a group "R" is depicted as existing on a ring system containing saturated carbons, as for example in the formula:

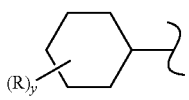

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group; there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the formula:

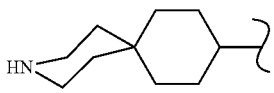

"Alkyl" is intended to include linear, branched, or cyclic hydrocarbon structures and combinations thereof, inclusively. For example, "$C_8$ alkyl" may refer to an n-octyl, iso-octyl, cyclohexylethyl, and the like. Lower alkyl refers to alkyl groups of from one to six carbon atoms. Examples of lower alkyl groups include methyl, ethyl, propyl, isopropyl, butyl, s-butyl, t-butyl, isobutyl, pentyl, hexyl and the like. Higher alkyl refers to alkyl groups containing more that eight carbon atoms. Exemplary alkyl groups are those of $C_{20}$ or below. Cycloalkyl is a subset of alkyl and includes cyclic hydrocarbon groups of from three to thirteen carbon atoms. Examples of cycloalkyl groups include c-propyl, c-butyl, c-pentyl, norbornyl, adamantyl and the like. In this application, alkyl refers to alkanyl, alkenyl, and alynyl residues (and combinations thereof); it is intended to include cyclohexylmethyl, vinyl, allyl, isoprenyl, and the like. Thus, when an alkyl residue having a specific number of carbons is named, all geometric isomers having that number of carbons are intended to be encompassed; thus, for example, either "butyl" or "$C_4$alkyl" is meant to include n-butyl, sec-butyl, isobutyl, t-butyl, isobutenyl and but-2-yne radicals; and for example, "propyl" or "$C_3$alkyl" each include n-propyl, propenyl, and isopropyl. Otherwise, if alkenyl and/or alkynyl descriptors are used in a particular definition of a group, for example "$C_4$alkyl" along "$C_4$alkenyl," then $C_4$alkenyl geometric isomers are not meant to be included in "$C_4$alkyl," but other 4-carbon isomers are, for example $C_4$alkynyl. For example, a more general description, intending to encompass the invention as a whole may describe a particular group as "$C_{1-8}$alkyl" while a preferred species may describe the same group as including, "$C_{1-8}$alkyl," "$C_{1-6}$alkenyl" and "$C_{1-5}$alkynyl."

"Alkylene" refers to straight or branched chain divalent radical consisting solely of carbon and hydrogen atoms, containing no unsaturation and having from one to ten carbon atoms, for example, methylene, ethylene, propylene, n-butylene and the like. Alkylene is a subset of alkyl, referring to the same residues as alkyl, but having two points of attachment and, specifically, fully saturated. Examples of alkylene include ethylene (—$CH_2CH_2$—), propylene (—$CH_2CH_2CH_2$—), dimethylpropylene (—$CH_2C(CH_3)_2CH_2$—), and cyclohexylpropylene (—$CH_2CH_2CH(C_6H_{13})$).

"Alkylidene" refers to a straight or branched chain unsaturated divalent radical consisting solely of carbon and hydrogen atoms, having from two to ten carbon atoms, for example, ethylidene, propylidene, n-butylidene, and the like. Alkylidene is a subset of alkyl, referring to the same residues as alkyl, but having two points of attachment and, specifically, double bond unsaturation. The unsaturation present includes at least one double bond.

"Alkylidyne" refers to a straight or branched chain unsaturated divalent radical consisting solely of carbon and hydrogen atoms having from two to ten carbon atoms, for example, propylid-2-ynyl, n-butylid-1-ynyl, and the like. Alkylidyne is a subset of alkyl, referring to the same residues as alkyl, but having two points of attachment and, specifically, triple bond unsaturation. The unsaturation present includes at least one triple bond.

Any of the above radicals, "alkylene," "alkylidene" and "alkylidyne," when optionally substituted, may contain alkyl substitution which itself contains unsaturation. For example, 2-(2-phenylethynyl-but-3-enyl)-naphthalene (IUPAC name) contains an n-butylid-3-ynyl radical with a vinyl substitutent at the 2-position of said radical.

"Alkoxy" or "alkoxyl" refers to the group —O-alkyl, for example including from one to eight carbon atoms of a straight, branched, cyclic configuration, unsaturated chains, and combinations thereof attached to the parent structure through an oxygen atom. Examples include methoxy, ethoxy, propoxy, isopropoxy, cyclopropyloxy, cyclohexyloxy and the like. Lower-alkoxy refers to groups containing one to six carbons.

"Substituted alkoxy" refers to the group —O-(substituted alkyl), the substitution on the alkyl group generally containing more than only carbon (as defined by alkoxy). One exemplary substituted alkoxy group is "polyalkoxy" or —O-optionally substituted alkylene-optionally substituted alkoxy, and includes groups such as —$OCH_2CH_2OCH_3$, and glycol ethers such as polyethyleneglycol and —$O(CH_2CH_2O)_xCH_3$, where x is an integer of between about two and about twenty, in another example, between about two and about ten, and in a further example between about two and about five. Another exemplary substituted alkoxy group is hydroxyalkoxy or —$OCH_2(CH_2)_yOH$, where y is for example an integer of between about one and about ten, in another example y is an integer of between about one and about four.

"Acyl" refers to groups of from one to ten carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to six carbons.

"α-Amino Acids" refer to naturally occurring and commercially available amino acids and optical isomers thereof. Typical natural and commercially available α-amino acids are glycine, alanine, serine, homoserine, threonine, valine, norvaline, leucine, isoleucine, norleucine, aspartic acid, glutamic acid, lysine, ornithine, histidine, arginine, cysteine, homocysteine, methionine, phenylalanine, homophenylalanine, phenylglycine, ortho-tyrosine, meta-tyrosine, para-tyrosine, tryptophan, glutamine, asparagine, proline and hydroxyproline. A "side chain of an α-amino acid" refers to the radical found on the α-carbon of an α-amino acid as defined above, for example, hydrogen (for glycine), methyl (for alanine), benzyl (for phenylalanine), and the like.

"Amino" refers to the group —$NH_2$. "Substituted amino," refers to the group —N(H)R or —N(R)R where each R is independently selected from the group: optionally substituted alkyl, optionally substituted alkoxy, optionally substituted aryl, optionally substituted heterocyclyl, acyl, carboxy, alkoxycarbonyl, sulfanyl, sulfinyl and sulfonyl, for example, diethylamino, methylsulfonylamino, and furanyl-oxy-sulfonamino.

"Aryl" refers to aromatic six- to fourteen-membered carbocyclic ring, for example, benzene, naphthalene, indane, tetralin, fluorene and the like, univalent radicals. As univalent radicals, the aforementioned ring examples are named, phenyl, naphthyl, indanyl, tetralinyl, and fluorenyl.

"Arylene" generically refers to any aryl that has at least two groups attached thereto. For a more specific example, "phenylene" refers to a divalent phenyl ring radical. A phenylene, thus may have more than two groups attached, but is defined by a minimum of two non-hydrogen groups attached thereto.

"Arylalkyl" refers to a residue in which an aryl moiety is attached to a parent structure via one of an alkylene, alkylidene, or alkylidyne radical. Examples include benzyl, phenethyl, phenylvinyl, phenylallyl and the like. Both the aryl, and the corresponding alkylene, alkylidene, or alkylidyne radical portion of an arylalkyl group may be optionally substituted. "Lower arylalkyl" refers to an arylalkyl where the "alkyl" portion of the group has one to six carbons; this can also be referred to as $C_{1-6}$ arylalkyl.

"Exo-alkenyl" refers to a double bond that emanates from an annular carbon, and is not within the ring system, for example the double bond depicted in the formula below.

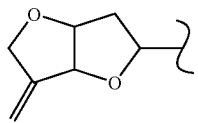

In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) can contain two substitution groups.

"Fused-polycyclic" or "fused ring system" refers to a polycyclic ring system that contains bridged or fused rings; that is, where two rings have more than one shared atom in their ring structures. In this application, fused-polycyclics and fused ring systems are not necessarily all aromatic ring systems. Typically, but not necessarily, fused-polycyclics share a vicinal set of atoms, for example naphthalene or 1,2,3,4-tetrahydro-naphthalene. A spiro ring system is not a fused-polycyclic by this definition, but fused polycyclic ring systems of the invention may themselves have spiro rings attached thereto via a single ring atom of the fused-polycyclic.

"Halogen" or "halo" refers to fluorine, chlorine, bromine or iodine. "Haloalkyl" and "haloaryl" refer generically to alkyl and aryl radicals that are substituted with one or more halogens, respectively. Thus, "dihaloaryl," "dihaloalkyl," "trihaloaryl" etc. refer to aryl and alkyl substituted with a plurality of halogens, but not necessarily a plurality of the same halogen; thus 4-chloro-3-fluorophenyl is within the scope of dihaloaryl.

"Heteroarylene" generically refers to any heteroaryl that has at least two groups attached thereto. For a more specific example, "pyridylene" refers to a divalent pyridyl ring radical. A pyridylene, thus may have more than two groups attached, but is defined by a minimum of two non-hydrogen groups attached thereto.

"Heteroatom" refers to O, S, N, or P.

"Heterocyclyl" refers to a stable three- to fifteen-membered ring radical that consists of carbon atoms and from one to five heteroatoms selected from the group consisting of nitrogen, phosphorus, oxygen and sulfur. For purposes of this invention, the heterocyclyl radical may be a monocyclic, bicyclic or tricyclic ring system, which may include fused or bridged ring systems as well as spirocyclic systems; and the nitrogen, phosphorus, carbon or sulfur atoms in the heterocyclyl radical may be optionally oxidized to various oxidation states. In a specific example, the group —$S(O)_{0-2}$—, refers to —S— (sulfide), —S(O)— (sulfoxide), and —$SO_2$— (sulfone). For convenience, nitrogens, particularly but not exclusively, those defined as annular aromatic nitrogens, are meant to include their corresponding N-oxide form, although not explicitly defined as such in a particular example. Thus, for a compound of the invention having, for example, a pyridyl ring; the corresponding pyridyl-N-oxide is meant to be included as another compound of the invention. In addition, annular nitrogen atoms may be optionally quaternized; and the ring radical may be partially or fully saturated or aromatic. Examples of heterocyclyl radicals include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Heteroalicyclic" refers specifically to a non-aromatic heterocyclyl radical. A heteroalicyclic may contain unsaturation, but is not aromatic.

"Heteroaryl" refers specifically to an aromatic heterocyclyl radical.

"Heterocyclylalkyl" refers to a residue in which a heterocyclyl is attached to a parent structure via one of an alkylene, alkylidene, or alkylidyne radical. Examples include (4-methylpiperazin-1-yl)methyl, (morpholin-4-yl)methyl, (pyridine-4-yl)methyl, 2-(oxazolin-2-yl)ethyl, 4-(4-methylpiperazin-1-yl)-2-butenyl, and the like. Both the heterocyclyl, and the corresponding alkylene, alkylidene, or alkylidyne radical portion of a heterocyclylalkyl group may be optionally substituted. "Lower heterocyclylalkyl" refers to a heterocyclylalkyl where the "alkyl" portion of the group has one to six carbons. "Heteroalicyclylalkyl" refers specifically to a heterocyclylalkyl where the heterocyclyl portion of the group is non-aromatic; and "heteroarylalkyl" refers specifically to a heterocyclylalkyl where the heterocyclyl portion of the group is aromatic Such terms may be described in more than one way, for example, "lower heterocyclylalkyl" and "heterocyclyl $C_{1-6}$alkyl" are equivalent terms.

"Optional" or "optionally" means that the subsequently described event or circumstance may or may not occur, and that the description includes instances where said event or circumstance occurs and instances in which it does not. One of ordinary skill in the art would understand that, with respect to any molecule described as containing one or more optional substitutents, that only sterically practical and/or synthetically feasible compounds are meant to be included. "Optionally substituted" refers to all subsequent modifiers in a term, for example in the term "optionally substituted aryl$C_{1-8}$alkyl," optional substitution may occur on both the "$C_{1-8}$alkyl" portion and the "aryl" portion of the molecule; and for example, optionally substituted alkyl includes optionally substituted cycloalkyl groups, which in turn are defined as including optionally substituted alkyl groups, potentially ad infinitum. A list of exemplary optional substitutions is included below in the definition of "substituted."

"Saturated bridged ring system" refers to a bicyclic or polycyclic ring system that is not aromatic. Such a system may contain isolated or conjugated unsaturation, but not aromatic or heteroaromatic rings in its core structure (but may have aromatic substitution thereon). For example, hexahydro-furo[3,2-b]furan, 2,3,3a,4,7,7a-hexahydro-1H-indene, 7-aza-bicyclo[2.2.1]heptane, and 1,2,3,4,4a,5,8,8a-octahydro-naphthalene are all included in the class "saturated bridged ring system.

"Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic.

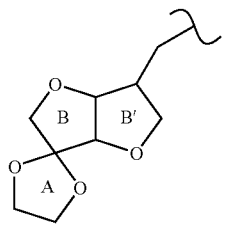

"Substituted" alkyl, aryl, and heterocyclyl, refer respectively to alkyl, aryl, and heterocyclyl, wherein one or more (for example up to about five, in another example, up to about three) hydrogen atoms are replaced by a substitutent independently selected from: optionally substituted alkyl (for example, fluoromethyl, hydroxypropyl, nitromethyl, aminoethyl and the like), optionally substituted aryl (for example, 4-hydroxyphenyl, 2,3-difluorophenyl, and the like), optionally substituted arylalkyl (for example, 1-phenyl-ethyl, para-methoxyphenylethyl and the like), optionally substituted heterocyclylalkyl (for example, 1-pyridin-3-yl-ethyl, N-ethylmorphonlino and the like), optionally substituted heterocyclyl (for example, 5-chloro-pyridin-3-yl, 1-methyl-piperidin-4-yl and the like), optionally substituted alkoxy (for example methoxyethoxy, hydroxypropyloxy, methylenedioxy and the like), optionally substituted amino (for example, methylamino, diethylamino, trifluoroacetylamino and the like), optionally substituted amidino, optionally substituted aryloxy (for example, phenoxy, para-chlorophenoxy, meta-aminophenoxy, para-phenoxyphenoxy and the like), optionally substituted arylalkyloxy (for example, benzyloxy, 3-chlorobenzyloxy, meta-phenoxybenzyloxy and the like), carboxy (—$CO_2H$), optionally substituted carboalkoxy (that is, acyloxy or —OC(=O)R), optionally substituted carboxyalkyl (that is, esters or —$CO_2R$), optionally substituted carboxamido, optionally substituted benzyloxycarbonylamino (CBZ-amino), cyano, optionally substituted acyl, halogen, hydroxy, nitro, optionally substituted alkylsulfanyl, optionally substituted alkylsulfinyl, optionally substituted alkylsulfonyl, thiol, halogen, hydroxy, oxo, carbamyl, optionally substituted acylamino, optionally substituted hydrazino, optionally substituted hydroxylamino, and optionally substituted sulfonamido.

"Sulfanyl" refers to the groups: —S-(optionally substituted alkyl), —S-(optionally substituted aryl), and —S-(optionally substituted heterocyclyl).

"Sulfinyl" refers to the groups: —S(O)—H, —S(O)-(optionally substituted alkyl), —S(O)-optionally substituted aryl), and —S(O)-(optionally substituted heterocyclyl).

"Sulfonyl" refers to the groups: —$S(O_2)$—H, —$S(O_2)$-(optionally substituted alkyl), —$S(O_2)$-optionally substituted aryl), —$S(O_2)$-(optionally substituted heterocyclyl), —$S(O_2)$-(optionally substituted alkoxy), —$S(O_2)$-optionally substituted aryloxy), and —$S(O_2)$-(optionally substituted heterocyclyloxy).

"Yield" for each of the reactions described herein is expressed as a percentage of the theoretical yield.

Some of the compounds of the invention may have imino, amino, oxo or hydroxy substitutents off aromatic heterocyclyl systems. For purposes of this disclosure, it is understood that such imino, amino, oxo or hydroxy substitutents may exist in their corresponding tautomeric form, i.e., amino, imino, hydroxy or oxo, respectively.

Compounds of the invention are named according to systematic application of the nomenclature rules agreed upon by the International Union of Pure and Applied Chemistry (IUPAC), International Union of Biochemistry and Molecular Biology (IUBMB), and the Chemical Abstracts Service (CAS).

The compounds of the invention, or their pharmaceutically acceptable salts, may have asymmetric carbon atoms, oxidized sulfur atoms or quaternized nitrogen atoms in their structure.

The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention.

It is assumed that when considering generic descriptions of compounds of the invention for the purpose of constructing a compound, such construction results in the creation of a stable structure. That is, one of ordinary skill in the art would recognize that there can theoretically be some constructs which would not normally be considered as stable compounds (that is, sterically practical and/or synthetically feasible, supra).

When a particular group with its bonding structure is denoted as being bonded to two partners; that is, a divalent radical, for example, —OCH₂—, then it is understood that either of the two partners may be bound to the particular group at one end, and the other partner is necessarily bound to the other end of the particular group, unless stated explicitly otherwise. Stated another way, divalent radicals are not to be construed as limited to the depicted orientation, for example "—OCH₂—" is meant to mean not only "—OCH₂—" as drawn, but also "—CH₂O—."

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting on enantiomer to the other by asymmetric transformation. For a mixture of enantiomers, enriched in a particular enantiomer, the major component enantiomer may be further enriched (with concomitant loss in yield) by recrystallization.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

"Kinase-dependent diseases or conditions" refer to pathologic conditions that depend on the activity of one or more protein kinases. Kinases either directly or indirectly participate in the signal transduction pathways of a variety of cellular activities including proliferation, adhesion, migration, differentiation and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

While not wishing to be bound to theory, phosphatases can also play a role in "kinase-dependent diseases or conditions" as cognates of kinases; that is, kinases phosphorylate and phosphatases dephosphorylate, for example protein substrates. Therefore compounds of the invention, while modulating kinase activity as described herein, may also modulate, either directly or indirectly, phosphatase activity. This additional modulation, if present, may be synergistic (or not) to activity of compounds of the invention toward a related or otherwise interdependent kinase or kinase family. In any case, as stated previously, the compounds of the invention are useful for treating diseases characterized in part by abnormal levels of cell metabolism, proliferation (i.e. tumor growth), programmed cell death (apoptosis), cell migration and invasion and angiogenesis associated with tumor growth.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinorna, glucagonoma, gastrinoma, carcinoid tumors, vipoma), small bowel (adenocarcinorna, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [neplrroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis defornians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma), granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal lands: neuroblastoma. Thus, the term "cancerous cell" as provided herein, includes a cell afflicted by any one of the above-identified conditions.

"Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference).

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) wherein the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gillan et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

In addition, it is intended that the present invention cover compounds made either using standard organic synthetic techniques, including combinatorial chemistry or by biological methods, such as bacterial digestion, metabolism, enzymatic conversion, and the like.

"Treating" or "treatment" as used herein covers the treatment of a disease-state in a human, which disease-state is characterized by abnormal cellular proliferation and/or invasion, or metabolism and includes at least one of: (i) preventing the disease-state from occurring in a human, in particular, when such human is predisposed to the disease-state but has not yet been diagnosed as having it; (ii) inhibiting the disease-state, i.e., arresting its development; and (iii) relieving the disease-state, i.e., causing regression of the disease-state. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

One of ordinary skill in the art would understand that certain crystallized, protein-ligand complexes, in particular p70S6K-ligand complexes, and their corresponding x-ray structure coordinates can be used to reveal new structural information useful for understanding the biological activity of kinases as described herein. As well, the key structural features of the aforementioned proteins, particularly, the shape of the ligand binding site, are useful in methods for designing or identifying selective modulators of kinases and in solving the structures of other proteins with similar features. Such protein-ligand complexes, having compounds of the invention as their ligand component, are an aspect of the invention.

As well, one of ordinary skill in the art would appreciate that such suitable x-ray quality crystals can be used as part of a method of identifying a candidate agent capable of binding to and modulating the activity of kinases. Such methods may be characterized by the following aspects: a) introducing into a suitable computer program, information defining a ligand binding domain of a kinase in a conformation (e.g. as defined by x-ray structure coordinates obtained from suitable x-ray quality crystals as described above) wherein the computer program creates a model of the three dimensional structures of the ligand binding domain, b) introducing a model of the three dimensional structure of a candidate agent in the computer program, c) superimposing the model of the candidate agent on the model of the ligand binding domain, and d)

assessing whether the candidate agent model fits spatially into the ligand binding domain. Aspects a-d are not necessarily carried out in the aforementioned order. Such methods may further entail: performing rational drug design with the model of the three-dimensional structure, and selecting a potential candidate agent in conjunction with computer modeling.

Additionally, one skilled in the art would appreciate that such methods may further entail: employing a candidate agent, so-determined to fit spatially into the ligand binding domain, in a biological activity assay for kinase modulation, and determining whether said candidate agent modulates kinase activity in the assay. Such methods may also include administering the candidate agent, determined to modulate kinase activity, to a mammal suffering from a condition treatable by kinase modulation, such as those described above.

Also, one skilled in the art would appreciate that compounds of the invention can be used in a method of evaluating the ability of a test agent to associate with a molecule or molecular complex comprising a ligand binding domain of a kinase. Such a method may be characterized by the following aspects: a) creating a computer model of a kinase binding pocket using structure coordinates obtained from suitable x-ray quality crystals of the kinase, b) employing computational algorithms to perform a fitting operation between the test agent and the computer model of the binding pocket, and c) analyzing the results of the fitting operation to quantify the association between the test agent and the computer model of the binding pocket.

General Administration

Administration of the compounds of the invention or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions will include a conventional pharmaceutical carrier or excipient and a compound of the invention as the/an active agent, and, in addition, may include other medicinal agents, pharmaceutical agents, carriers, adjuvants, etc. Compositions of the invention may be used in combination with anticancer or other agents that are generally administered to a patient being treated for cancer. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

Utility of Compounds of the Invention as Screening Agents

To employ the compounds of the invention in a method of screening for candidate agents that bind to, for example p70S6K receptor kinase, the protein is bound to a support, and a compound of the invention is added to the assay. Alternatively, the compound of the invention is bound to the support and the protein is added. Classes of candidate agents among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate agent to, for example, p70S6K protein may be done in a number of ways. In one example, the candidate agent (the compound of the invention) is labeled, for example, with a fluorescent or radioactive moiety and binding determined directly. For example, thus may be done by attaching all or a portion of the p70S6K protein to a solid support, adding a labeled agent (for example a compound of the invention in which at least one atom has been replaced by a detectable isotope), washing off excess reagent, and determining whether the amount of the label is that present on the solid support. Various blocking and washing steps may be utilized as is known in the art.

By "labeled" herein is meant that the compound is either directly or indirectly labeled with a label which provides a detectable signal, for example, radioisotope, fluorescent tag, enzyme, antibodies, particles such as magnetic particles, chemiluminescent tag, or specific binding molecules, and the like. Specific binding molecules include pairs, such as biotin and streptavidin, digoxin and antidigoxin, and the like. For the specific binding members, the complementary member would normally be labeled with a molecule which provides for detection, in accordance with known procedures, as outlined above. The label can directly or indirectly provide a detectable signal.

In some embodiments, only one of the components is labeled. For example, p70S6K protein may be labeled at tyrosine positions using $^{125}$I, or with fluorophores. Alternatively, more than one component may be labeled with different labels; using $^{125}$I for the proteins, for example, and a fluorophor for the candidate agents.

The compounds of the invention may also be used as competitors to screen for additional drug candidates. "candidate bioactive agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation or metabolic phenotype or the expression of a cellular proliferation or metabolic sequence, including both nucleic acid sequences and protein sequences. In other cases, alteration of cellular proliferation or metabolic protein binding and/or activity is screened. In the case where protein binding or activity is screened, some embodiments exclude molecules already known to bind to that particular protein. Exemplary embodiments of assays described herein include candidate agents, which do not bind the target protein in its endogenous native state, termed herein as "exogenous" agents. In one example, exogenous agents further exclude antibodies to p70S6K.

Candidate agents can encompass numerous chemical classes, though typically they are organic molecules having a molecular weight of more than about 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, for example at least two of the functional chemical groups. The candidate agents often comprise cyclical carbon or heterocyclyl structures and/or aromatic or polyaromatic structures substituted with one or more of the above functional groups. Candidate agents are also found among biomolecules including peptides, saccharides, fatty acids, steroids, purines, pyrimidines, derivatives, structural analogs, or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In one example, the binding of the candidate agent is determined through the use of competitive binding assays. In this example, the competitor is a binding moiety known to bind to p70S6K, such as an antibody, peptide, binding partner, ligand, etc. Under certain circumstances, there may be competitive binding as between the candidate agent and the binding moiety, with the binding moiety displacing the candidate agent.

In some embodiments, the candidate agent is labeled. Either the candidate agent, or the competitor, or both, is added first to p70S6K protein for a time sufficient to allow binding, if present. Incubations may be performed at any temperature that facilitates optimal activity, typically between 4° C. and 40° C.

Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In one example, the competitor is added first, followed by the candidate agent. Displacement of the competitor is an indication the candidate agent is binding to p70S6K and thus is capable of binding to, and potentially modulating, the activity of the p70S6K. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to p70S6K with a higher affinity. Thus, if the candidate agent is labeled, the presence of the label on the support, coupled with a lack of competitor binding, may indicate the candidate agent is capable of binding to p70S6K.

It may be of value to identify the binding site of p70S6K. This can be done in a variety of ways. In one embodiment, once p70S6K has been identified as binding to the candidate agent, the p70S6K is fragmented or modified and the assays repeated to identify the necessary components for binding.

Modulation is tested by screening for candidate agents capable of modulating the activity of p70S6K comprising the steps of combining a candidate agent with p70S6K, as above, and determining an alteration in the biological activity of the p70S6K. Thus, in this embodiment, the candidate agent should both bind to (although this may not be necessary), and alter its biological or biochemical activity as defined herein. The methods include both in vitro screening methods and in vivo screening of cells for alterations in cell viability, morphology, and the like.

Alternatively, differential screening may be used to identify drug candidates that bind to native p70S6K, but cannot bind to modified p70S6K.

Positive controls and negative controls can be used in the assays. For example, all control and test samples are performed in at least triplicate to obtain statistically significant results. Incubation of samples is for a time sufficient for the binding of the agent to the protein. Following incubation, samples are washed free of non-specifically bound material and the amount of bound, generally labeled agent determined. For example, where a radiolabel is employed, the samples can be counted in a scintillation counter to determine the amount of bound compound.

A variety of other reagents can be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components can be added in any order that provides for the requisite binding.

One of ordinary skill in the art would understand that certain crystallized, protein-ligand complexes, in particular p70S6K-ligand complexes, and their corresponding x-ray structure coordinates can be used to reveal new structural information useful for understanding the biological activity of p70S6 kinase's as described herein. As well, the key structural features of the aforementioned proteins, particularly, the shape of the ligand binding site, are useful in methods for designing or identifying selective modulators of p70S6 kinase's and in solving the structures of other proteins with similar features. Ligands of such complexes may include compounds of the invention as described herein.

As well, one of ordinary skill in the art would appreciate that such suitable x-ray quality crystals can be used as part of a method of identifying a candidate agent capable of binding to and modulating the activity of p70S6 kinases. Such methods may be characterized by the following aspects: a) introducing into a suitable computer program, information defining a ligand binding domain of a p70S6 kinase in a conformation (e.g. as defined by x-ray structure coordinates obtained from suitable x-ray quality crystals as described above) wherein the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods may further entail: performing rational drug design with the model of the three-dimensional structure, and selecting a potential candidate agent in conjunction with computer modeling.

Additionally, one skilled in the art would appreciate that such methods may further entail: employing a candidate agent, so-determined to fit spatially into the ligand binding domain, in a biological activity assay for p70S6 kinase modulation, and determining whether said candidate agent modulates p70S6 kinase activity in the assay. Such methods may also include administering the candidate agent, determined to modulate p70S6 kinase activity, to a mammal suffering from a condition treatable by p70S6 kinase modulation, such as those described above.

Also, one skilled in the art would appreciate that compounds of the invention can be used in a method of evaluating the ability of a test agent to associate with a molecule or molecular complex comprising a ligand binding domain of a p70S6 kinase. Such a method may be characterized by the following aspects: a) creating a computer model of a p70S6 kinase binding pocket using structure coordinates obtained from suitable x-ray quality crystals of the p70S6 kinase, b) employing computational algorithms to perform a fitting operation between the test agent and the computer model of the binding pocket, and c) analyzing the results of the fitting operation to quantify the association between the test agent and the computer model of the binding pocket.

Abbreviations and their Definitions

The following abbreviations and terms have the indicated meanings throughout:

| Abbreviation | Meaning |
|---|---|
| Ac | acetyl |
| ACN | acetonitrile |
| ATP | adenosine triphosphate |
| BNB | 4-bromomethyl-3-nitrobenzoic acid |
| Boc | t-butyloxy carbonyl |
| br | broad |
| Bu | butyl |
| °C. | degrees Celsius |
| c- | cyclo |
| CBZ | CarboBenZoxy=benzyloxycarbonyl |
| d | doublet |
| dd | doublet of doublet |
| dt | doublet of triplet |
| DBU | Diazabicyclo[5.4.0]undec-7-ene |
| DCM | dichloromethane=methylene chloride =$CH_2Cl_2$ |
| DCE | dichloroethylene |
| DEAD | diethyl azodicarboxylate |
| DIC | diisopropylcarbodiimide |
| DIEA | N,N-diisopropylethyl amine |
| DMAP | 4-N,N-dimethylaminopyridine |
| DMF | N,N-dimethylfonnamide |
| DMSO | dimethyl sulfoxide |
| DVB | 1,4-divinylbenzene |
| EEDQ | 2-ethoxy-1-ethoxycarbonyl-1,2-dihydroquinoline |
| EI | Electron Impact ionization |
| Et | ethyl |
| Fmoc | 9-fluorenylmethoxycarbonyl |
| g | gram(s) |
| GC | gas chromatography |
| h or hr | hour(s) |
| HATU | 0-(7-Azabenzotriazol-1-yl)-1,1,3,3-tetramethyluronium hexafluorophosphate |
| HMDS | hexamethyldisilazane |
| HOAc | acetic acid |
| HOBt | hydroxybenzotriazole |
| HPLC | high pressure liquid chromatography |
| L | liter(s) |
| M | molar or molarity |
| m | multiplet |
| Me | methyl |
| mesyl | methanesulfonyl |
| mg | milligram(s) |
| MHz | megahertz (frequency) |
| Min | minute(s) |
| mL | milliliter(s) |
| mM | millimolar |
| mmol | millimole(s) |
| mol | mole(s) |
| MS | mass spectral analysis |
| MTBE | methyl t-butyl ether |
| N | normal or normality |
| NBS | N-bromosuccinimide |

-continued

| Abbreviation | Meaning |
|---|---|
| NCS | N-chlorosuccinimide |
| nM | nanomolar |
| NMO | N-methylmorpholine oxide |
| NMR | nuclear magnetic resonance spectroscopy |
| PEG | polyethylene glycol |
| pEY | poly-glutamine, tyrosine |
| Ph | phenyl |
| PhOH | phenol |
| PfP | pentafluorophenol |
| PfPy | pentafluoropyridine |
| PPTS | Pyridinium p-toluenesulfonate |
| Py | pyridine |
| PyBroP | bromo-tris-pyrrolidino-phosphonium hexafluorophosphate |
| q | quartet |
| RT | Room temperature |
| Sat'd | saturated |
| s | singlet |
| s- | secondary |
| t- | tertiary |
| t or tr | triplet |
| TBDMS | t-butyldimethylsilyl |
| TES | triethylsilane |
| TFA | trifluoroacetic acid |
| THF | tetrahydrofuran |
| TMOF | trimethyl orthoformate |
| TMS | trimethylsilyl |
| tosyl | p-toluenesulfonyl |
| Trt | triphenylmethyl |
| µL | microliter(s) |
| µM | Micromole(s) or micromolar |

Synthesis of Compounds

Schemes 1 and 2 depict general synthetic routes for exemplary compounds of the invention according to Formula I, and are not intended to be limiting. Specific examples are described subsequently to this general synthetic description. With the descriptions of the general routes and the specific examples thereafter, one of ordinary skill in the art would be able to make compounds of the invention as described in the detailed description and claims.

Scheme 1 shows that in general, compounds according to Formula I can be made, for example, via a linear route, including synthesis of a 2-substituted pyrimidine ring system. For example, compound 1 and compound 2 are combined in an alcohol, and allowed to react at room temperature to give 2-aminopyrimidine 3, wherein $R^3$ is as described in accordance with Formula I. The sulfhydryl of pyrimidine 3 serves as a nucleophile, for example, with alkylating agents such as α-chloroamide 4. Thus 3 and 4 are combined to make 5, which represents compounds according to Formula I. One of ordinary skill in the art would appreciate that although compounds 3 and 4 contain a free sulfhydryl and activated alkyl halide moities, respectively, used for forming a sulfur-carbon bond in 5; other nucleophile-electrophile combinations can be used to form compounds according to Formula I. For example, other electrophilic reagents can be used to alkylate 3. Alternatively, 3, after appropriate conversion, or compounds similar to 3 can be used as an electrophilic component of an electrophile-nucleophile combination (as outlined in Scheme 2 below).

Scheme 1

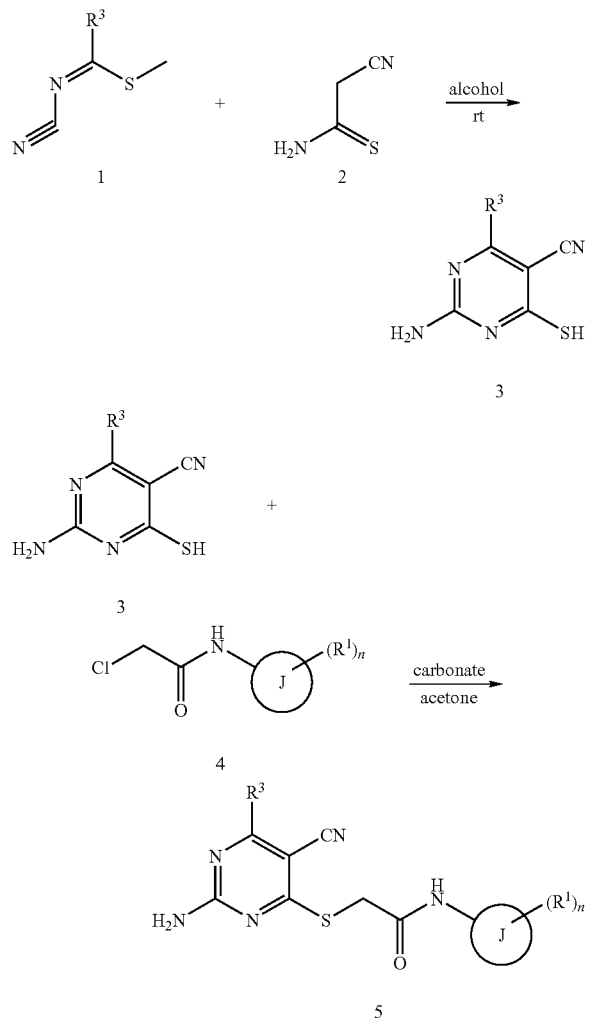

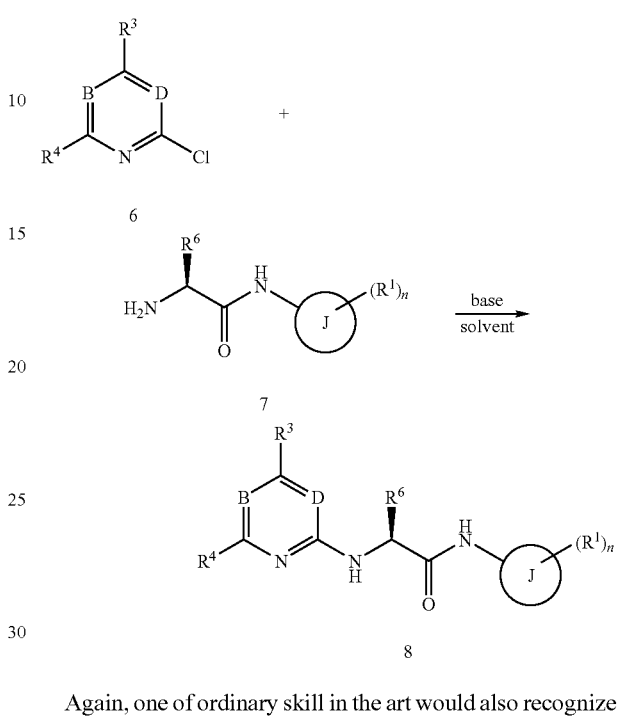

Scheme 2 depicts combination of, for example a commercially available, pyridine (where B and D are =C(R$^2$)—), pyrimidine (where one of B and D is =N—, and the other of B and D is =C(R$^2$)—), or 1,3,5-triazine (where B and D are =N—) 6 with an amino acid derivative 7. In this example, the chlorine of 6 serves as a leaving group to allow nucleophilic aromatic substitution via participation of the nucleophilic α-nitrogen of 7 to form 8. Alternatively, for example, the sulfhydryl group of compounds such as 3 (see Scheme 1) can be oxidized to form a leaving group and thus make an example of an electrophilic partner similar to 6 (see also specific examples below).

One of ordinary skill in the art would appreciate that many combinations of electrophile-nucleophile type for example, are possible for the formation of compounds of the invention, in particular when forming the linkage (—X—Y-Z-A- as described in Formula I) between for example a pyridine, pyrimidine, or triazine ring system as just described and ring J. Additionally, for example, the linkage —X—Y-Z-A- may be formed via aldol or Wittig-type reactions using aldehyde and ketone partners. One skilled in the art would understand and appreciate that many alternatives are available for synthesizing compounds of the invention, and that the various substitutions, R$^1$, R$^2$, R$^3$, R$^4$, R$^5$, and R$^6$ for example, can be introduced and/or manipulated at virtually any point in synthetic routes to make compounds of the invention according to Formula I.

Again, one of ordinary skill in the art would also recognize that the descriptions associated with Schemes 1 and 2 are generalizations, and that there are other combinations of steps and approaches that can be used to make compounds of the invention. The examples that follow provide much more detailed descriptions of making exemplary compounds of the invention.

EXAMPLES

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety. Generally, but not necessarily, each example set out below describes a multi-step synthesis as outlined above.

Example 1

Synthesis of 2-Amino-4-mercapto-6-methylsulfanyl-pyrimidine-5-carbonitrile

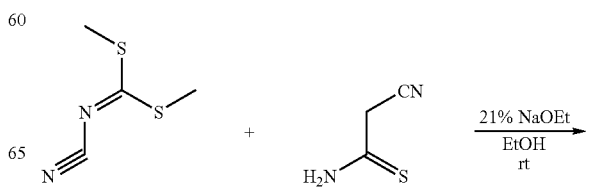

-continued

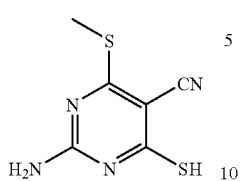

To a 50 mL round-bottom flask were added dimethylcyanodithioiminocarbonate (803 mg, 5.5 mmol), cyanothioacetamide (549 mg, 5.5 mmol) and ethanol (8 mL). The sodium ethoxide (21% ethanol solution, 1.8 mL) was added to the reaction mixture at room temperature. After the reaction mixture was stirred for 2 hrs at room temperature, the precipitate was filtered and gave to white solid (641 mg, 60%). No further purification was necessary. LC-MS: (ES+) m/z 199.0 (M+1).

Example 2

Synthesis of 2-(2-Amino-5-cyano-6-methylsulfanyl-pyrimidin-4-ylsulfanyl)-N-(3-trifluoromethyl-phenyl)-acetamide

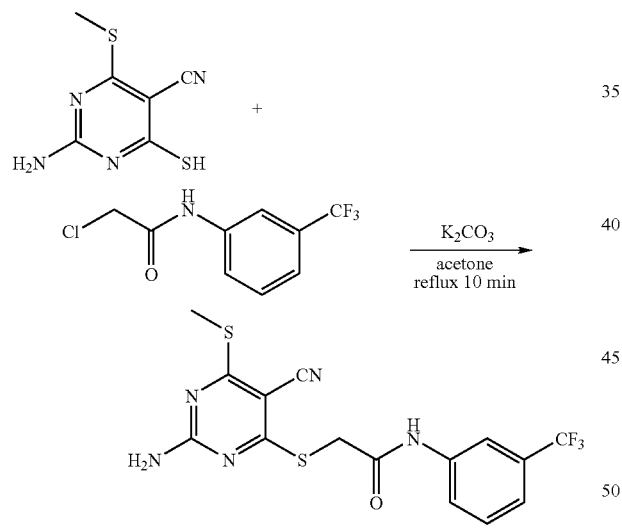

To a 50 mL round-bottomed flask were added 2-Amino-4-mercapto-6-methylsulfanyl-pyrimidine-5-carbonitrile (3, 153 mg, 0.77 mmol, 1.0 eq.), 2-Chloro-N-(3-trifluoromethyl-phenyl)-acetamide (4, 184 mg, 0.77 mmol), potassium carbonate (106 mg, 0.77 mmol) and acetone (10 mL). The reaction mixture was heated to reflux for 10 min. After removal of potassium carbonate by filtration, the reaction mixture was concentrated to solid. Recrystallization with ether-ethyl acetate gave white solid (240 mg, 80%). LC-MS: (ES+) m/z 400.0 (M+1). $^1$H-NMR, Varian 400 MHz (DMSO-$d_6$) δ 10.50 (s, 1H), 8.04(s, 1H), 7.73 (d, 1H), 7.54 (t, 1H), 7.39 (d, 1H), 4.07 (s, 2H), 2.44 (s, 3H) ppm.

Example 3

Synthesis of 2-(2-Amino-5-cyano-6-methylamino-pyrimidin-4-ylsulfanyl)-N-(3-trifluoromethyl-phenyl)-acetamide

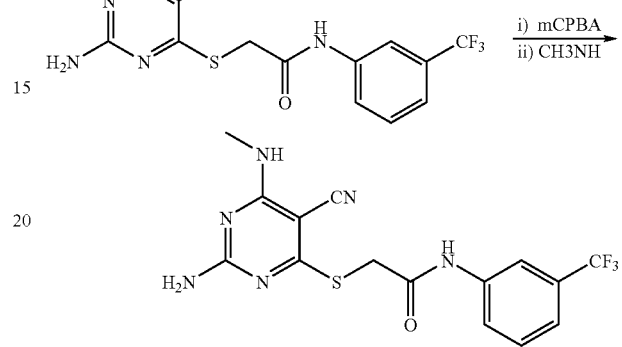

To a 50 mL round-bottomed flask were added 2-(2-Amino-5-cyano-6-methylsulfanyl-pyrimidin-4-ylsulfanyl)-N-(3-trifluoromethyl-phenyl)-acetamide (5:100 mg, 0.25 mmol, 1.0 eq.), m-Chloroperbenzoic acid (65 mg, 0.37 mmol), and dichloromethane (4 mL). The reaction mixture was stirred at room temperature for 10 min. The precipitate was filtered and gave to white solid. No further purification was necessary (91 mg, 88%). LC-MS: (ES+) m/z 416.1 (M+1)

To a 50 mL round-bottomed flask were added 2-(2-Amino-5-cyano-6-methanesulfinyl-pyrimidin-4-ylsulfanyl)-N-(3-trifluoromethyl-phenyl)-acetamide (0.2 mmol, 1.0 eq.), methyl amine (2M in THF, 0.3 mmol), and acetonitrile (1 mL). The reaction mixture was stirred at room temperature for overnight. The crude material was purified by column chromatography (18 mg). LC-MS: (ES+) m/z 383 (M+1). $^1$H-NMR, Varian 400 MHz (DMSO-$d_6$) δ 10.47 (s, 1H), 8.07 (s, 1H), 7.75 (d, 1H), 7.55 (t, 1H), 7.40 (d, 1H), 7.36 (d, 1H), 7.25 (s, 1H), 3.95 (s, 2H), 2.73 (d, 3H) ppm.

Example 4

Synthesis of 2-(2-Amino-5-cyano-6-methylamino-pyrimidin-4-ylhydrazino)-N-(3-trifluoromethyl-phenyl)-amide

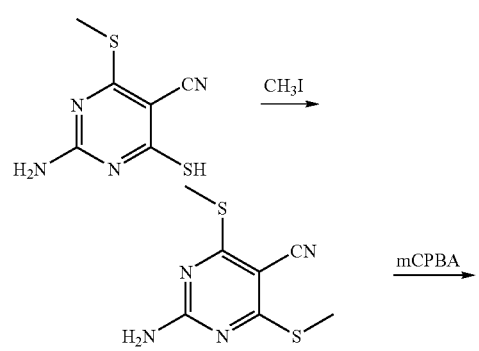

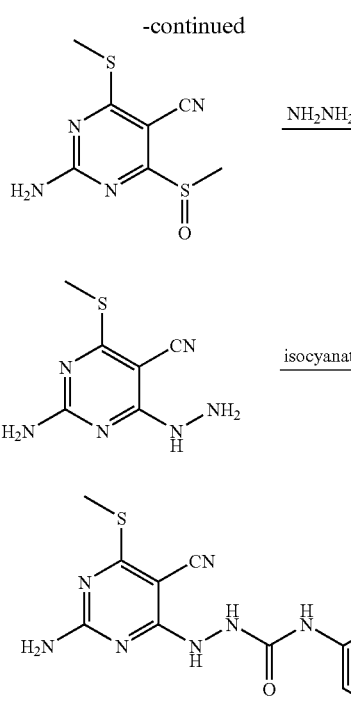

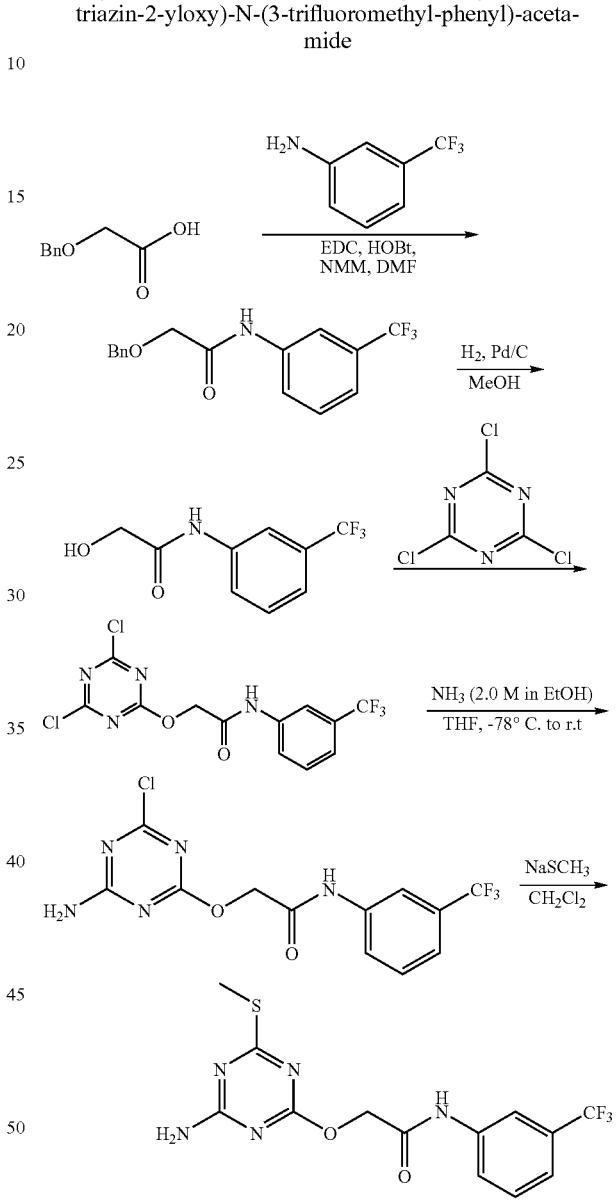

2-Amino-4,6-bis-methylsulfanyl-pyrimidine-5-carbonitrile: To a 50 mL round-bottomed flask were added 2-Amino-4-mercapto-6-methylsulfanyl-pyrimidine-5-carbonitrile (3:50 mg, 2.5 mmol, 1.0 eq.), methyl iodide (8.2 mmol), and acetone (10 mL). The reaction mixture was heated at 80° C. for 5 min. The precipitate was filtered and gave to white solid. No further purification was necessary (312 mg, 58%). LC-MS: (ES+) m/z 213 (M+1). $^1$H-NMR, Varian 400 MHz (DMSO-$d_6$) δ 2.52 (s, 3H), 2.46 (s, 3H) ppm 2-Amino-4-methanesulfinyl-6-methylsulfanyl-pyrimidine-5-carbonitrile: To a 50 mL round-bottomed flask were added 2-Amino-4,6-bis-methylsulfanyl-pyrimidine-5-carbonitrile (7:212 mg, 1 mmol, 1.0 eq.), m-chloroperbenzoic acid (2 mmol), and dichloromethane (6 mL). The reaction mixture was stirred at room temperature for 1 hr. The precipitate was filtered and gave to white solid. No further purification was necessary (282 mg). LC-MS: (ES+) m/z 229 (M+1). $^1$H-NMR, Varian 400 MHz (DMSO-$d_6$) δ 2.85 (s, 3H), 2.47 (s, 3H) ppm.

2-Amino-4-hydrazino-6-methylsulfanyl-pyrimidine-5-carbonitrile: To a 50 mL round-bottomed flask were added 2-Amino-4-methanesulfinyl-6-methylsulfanyl-pyrimidine-5-carbonitrile (8:100 mg, 0.4 mmol.), hydrazine hydrate (0.8 mmol), and acetonitrile (2 mL). The reaction mixture was stirred at room temperature for 4 hr. The precipitate was filtered and gave to white solid. No further purification was necessary (76 mg). LC-MS: (ES+) m/z 197 (M+1).

Synthesis of 2-(2-Amino-5-cyano-6-methylamino-pyrimidin-4-ylhydrazino)-N-(3-trifluoromethyl-phenyl)-amide: To a 50 mL round-bottomed flask were added 2-Amino-4-hydrazino-6-methylsulfanyl-pyrimidine-5-carbonitrile (9:76 mg, 0.38 mmol.), trifluoro-methyl-m-tolyl isocyanate (0.8 mmol), triethylamine (0.8 mmol) and acetonitrile (2 mL). The reaction mixture was stirred at 0° C. to room temperature for overnight. The precipitate was filtered and further purification was done by HPLC (10 mg). LC-MS: (ES+) m/z 384 (M+1).

Example 5

Synthesis of 2-(4-Amino-6-methylsulfanyl-[1,3,5] triazin-2-yloxy)-N-(3-trifluoromethyl-phenyl)-acetamide 2-Benzyloxy-N-(3-trifluoromethyl-phenyl)-acetamide: To a 500 mL round-bottomed flask was added benzyloxyacetic acid (4.80 g, 28.9 mmol, 1.0 eq.), EDC (8.30 g, 43.3 mmol, 1.5 eq.), HOBt (5.85 g, 43.3 mmol, 1.5 eq.), and DMF (200 mL). N-methylmorpholine (6.5 mL, 57.7 mmol, 2.0 eq.) was added and the mixture was stirred at room temperature for 30 min. 3-Trifluoromethylaniline (6.12 mL, 49.1 mmol, 1.7 eq.) was added and the reaction mixture was stirred overnight at room temperature. The reaction mixture was diluted with EtOAc (500 mL) and then washed with $H_2O$ (1×100 mL), 10% aqueous LiCl (3×100 mL), $H_2O$ (1×100 mL), and brine (1×50 mL). The combined aqueous phases were extracted with EtOAc (3×75 mL). The organic phases were combined, dried over anhydrous sodium sulfate, filtered, and concentrated to give an oil which was used in the next step without further purification. LC/MSD (HP Series 1100 MSD) Expected MW: 309.10, Observed M+H, 310.1, Retention time: 1.67. ¹H-NMR, DMSO-d6, Varian 400 MHz δ 10.15 (s, 1H), 8.13 (s, 1H), 7.86 (d, 1H), 7.54 (t, 1H), 7.39-6.72 (m, 5H) 5.55 (s, 1H), 4.62 (s, 2H), 4.12 (s, 2H) ppm.

2-Hydroxy-N-(3-trifluoromethyl-phenyl)-acetamide: To a 1 L pressure vessel was added crude 2-Benzyloxy-N-(3-trifluoromethyl-phenyl)-acetamide (~10 g) and methanol (400 mL). The solution was purged with N₂. 10% Pd/C (1.1 g) was added. The vessel was placed under H₂ atmosphere at 50 psi for 2.5 h. LC/MS analysis shows only partial hydrogenolysis of the benzyl ether, so Pd(OH)₂H₂O (2 g) was added and the vessel is placed again under H₂ atmosphere at 50 psi for 2.5 h. The reaction mixture was filtered through a pad of Celite and concentrated to give a brown oil. The crude material was purified via flash chromatography (1:1 EtOAc/Hexanes) to give 2-hydroxy-N-(3-trifluoromethyl-phenyl)-acetamide as a white solid (5.27 g, 84% yield, two steps). LC/MSD (HP Series 1100 MSD) Expected MW: 219.05, Observed M+H, 220.0, Retention time: 1.22. ¹H-NMR, DMSO-d6, Varian 400 MHz δ 10.07 (s, 1H), 8.22 (s, 1H), 7.97 (dd, 1H), 7.55 (t, 1H), 7.41 (m, 1H), 5.76 (t, 1H), 4.03 (d, 2H) ppm.

2-(4,6-Dichloro-[1,3,5]triazin-2-yloxy)-N-(3-trifluoromethyl-phenyl)-acetamide: To a 200 mL recovery flask was added cyanuric chloride (504 mg, 2.73 mmol, 1.0 eq.) and CH₂Cl₂ (50 mL). The solution was cooled to 0° C. In a separate flask, a solution of 2-hydroxy-N-(3-trifluoromethyl-phenyl)-acetamide (599 mg, 2.73 mmol, 1.0 eq.) and i-Pr₂NEt (524 µL, 2.00 mmol, 1.1 eq.) in 10 mL was prepared and then slowly added to the reaction flask. The reaction was stirred for 2 h while warming to room temperature. The reaction was quenched with H₂O (50 mL). The organic phase washed with brine (1×50 mL). The combined aqueous phases were extracted with CH₂Cl₂ (2×25 mL). The combined organic phases were dried over anhydrous sodium sulfate, filtered, and concentrated to give an off-white solid. The crude material was purified via flash chromatography (1:4 EtOAc/Hexanes) to give 2-(4,6-dichloro-[1,3,5]triazin-2-yloxy)-N-(3-trifluoromethyl-phenyl)-acetamide as a white solid (600 mg, 60%). LC/MSD (HP Series 1100 MSD) Expected MW: 365.99, Observed M+H: 367.0, Retention time: 1.59. ¹H-NMR, DMSO-d6, Varian 400 MHz δ 11.19 (s, 1H), 10.63 (s, 1H), 8.08 (s, 1H), 7.75 (d, 1H), 7.59 (t, 1H), 7.44 (d, 1H), 4.99 (s, 2H) ppm.

2-(4-Amino-6-chloro-[1,3,5]triazin-2-yloxy)-N-(3-trifluoromethyl-phenyl)-acetamide: To a 25 mL recovery flask was added 2-(4,6-dichloro-[1,3,5]triazin-2-yloxy)-N-(3-trifluoromethyl-phenyl)-acetamide (293 mg, 0.798 mmol, 1.0 eq.) and a stirbar. THF (7 mL) was added and the resulting solution was cooled to −78° C. Ammonia (NH₃, 2.0 M in EtOH, 2.00 mL, 6 mmol, 5 eq.) was added in 400 µl aliquots until the reaction was complete by LC/MS analysis. The reaction mixture was diluted with EtOAc (50 mL) and washed with H₂O (1×50 mL) and brine (1×50 mL). The combined aqueous phases were extracted with EtOAc (2×25 mL). The combined organic phases were dried over anhydrous sodium sulfate, filtered, and concentrated to give an off-white solid. The solid washed with EtOAc to give 2-(4-Amino-6-chloro-[1,3,5]triazin-2-yloxy)-N-(3-trifluoromethyl-phenyl)-acetamide as a white solid (70 mg, 25%). LC/MSD (HP Series 1100 MSD) Expected MW: 357.04, Observed M−H, 358.1, Retention time: 1.37. ¹H-NMR, DMSO-d6, Varian 400 MHz δ 10.54 (s, 1H), 8.10-8.07 (m, 2H), 8.02 (s, 1H), 7.78 (d, 1H), 7.57 (t, 1H), 7.43 (d, 1H), 4.96 (s, 2H) ppm.

2-(4-Amino-6-methylsulfanyl-[1,3,5]triazin-2-yloxy)-N-(3-trifluoromethyl-phenyl)-acetamide: To a 25 mL recovery flask was added 2-(4-Amino-6-chloro-[1,3,5]triazin-2-yloxy)-N-(3-trifluoromethyl-phenyl)-acetamide (33 mg, 0.0950 mmol, 1.0 eq.) and CH₂Cl₂ (7 mL). Sodium thiomethoxide (20 mg, 0.285 mmol, 3.0 eq.) was added and the resulting solution was stirred at room temperature for 1 h. The reaction was diluted with CH₂Cl₂ (50 mL) and washed with H₂O (1×50 mL) and brine (1×50 mL). The combined aqueous phases were extracted with CH₂Cl₂ (2×25 mL). The combined organic phases were dried over anhydrous sodium sulfate, filtered, and concentrated to give a brown solid. The crude material was purified via preparative HPLC to give 2-(4-Amino-6-methylsulfanyl-[1,3,5]triazin-2-yloxy)-N-(3-trifluoromethyl-phenyl)-acetamide as a white solid (6.2 mg, 24% yield). LC/MSD (HP Series 1100 MSD) Expected MW: 359.07, Observed M+H, 360.1, Retention time: 1.40. Analytical LC: 98%, Retention time: 4.87 (11 minute run). ¹H-NMR, CH₃OH-d4, Varian 400 MHz δ 8.01 (s, 1H), 7.81 (d, 1H), 7.51 (t, 1H), 7.40 (d, 1H), 4.94 (s, 2H), 2.46 (3H) ppm.

Example 6

Synthesis of 2S-(2-Amino-5-cyano-6-methylsulfanyl-pyrimidin-4-yloxy)-N-(3-trifluoromethyl-phenyl)-propionamide

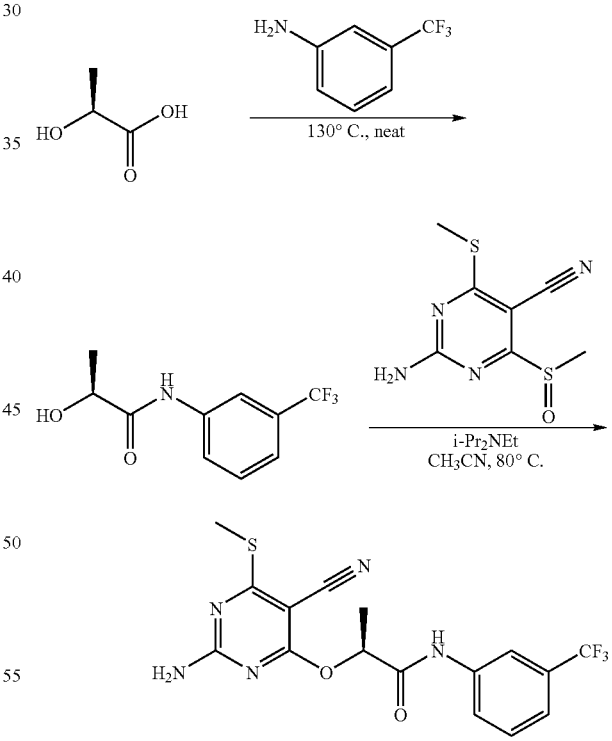

2S-Hydroxy-N-(3-trifluoromethyl-phenyl)-propionamide: To a 100 mL recovery flask was added L-lactic acid (85% in H₂O, 8.09 g, 76.3 mmol, 0.95 eq.) and 3-trifluoromethylaniline (10 mL, 80.4 mmol, 1.0 eq.). The mixture was heated at 130° C. for 2 h. After cooling, 10% aqueous HCl (100 mL) was added and the resulting solution was extracted with EtOAc (3×100 mL). The combined organic phases were dried over anhydrous sodium sulfate, filtered, and concentrated to give a pale oil. The crude material was treated with 30% EtOAc/Hexanes upon which a white solid precipitated. The solid was filtered to give 2S-hydroxy-N-(3-trifluoromethyl-phenyl)-propionamide (5.6 g, 27%). LC/MSD (HP Series 1100 MSD) Expected MW: 233.07, Observed M+H, 234.0, Retention time: 1.28.

2S-(2-Amino-5-cyano-6-methylsulfanyl-pyrimidin-4-yloxy)-N-(3-trifluoromethyl-phenyl)-propionamide: To a 48 mL pressure vessel was added 2-amino-4-methanesulfinyl-6-methylsulfanyl-pyrimidine-5-carbonitrile (150 mg, 0.657 mmol, 1.0 eq.), 2S-hydroxy-N-(3-trifluoromethyl-phenyl)-propionamide (460 mg, 1.97 mmol, 3.0 eq.), i-Pr₂NEt (459 µL, 2.63 mmol, 4.0 eq.), and CH₃CN (10 mL). The mixture was stirred at 80° C. overnight. The reaction was concentrated and then suspended in EtOAc (100 mL). The organic phase was washed with H₂O (1×50 mL) and brine (1×50 mL). The combined aqueous phases were extracted with EtOAc (2×50 mL). The combined organic phases were dried over anhydrous sodium sulfate, filtered, and concentrated to give a brown oil. The crude material was purified via preparative HPLC to give 2S-(2-amino-5-cyano-6-methylsulfanyl-pyrimidin-4-yloxy)-N-(3-trifluoromethyl-phenyl)-propionamide as a white solid (40 mg, 15%). LC/MSD (HP Series 1100 MSD) Expected MW: 397.08, Observed M+H, 398.1, Retention time: 1.47. Analytical LC: 98%, Retention time: 5.58 (11 minute run). ¹H-NMR, DMSO-d6, Varian 400 MHz δ 10.55 (s, 1H), 8.07 (s, 1H), 7.79 (d, 1H), 7.56 (t, 1H), 7.42 (d, 1H), 5.25 (q, 1H), 2.41 (s, 3H), 1.54 (d, 3H) ppm.

Example 7

Synthesis of 2-Amino-4-methylsulfanyl-6-(6-trifluoromethyl-1H-benzoimidazol-2-ylmethylsulfanyl)-pyrimidine-5-carbonitrile

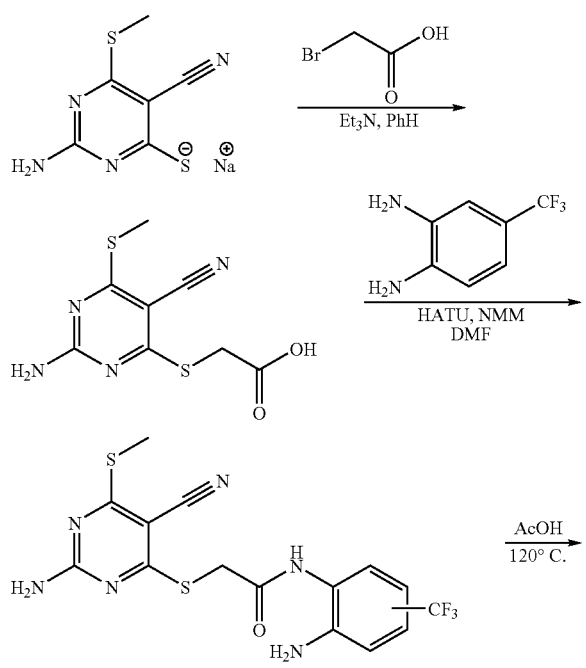

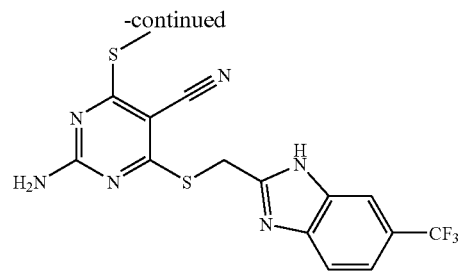

-continued mixture of regioisomeric amides (2-Amino-5-cyano-6-methylsulfanyl-pyrimidin-4-ylsulfanyl)-acetic acid: To a 100 mL recovery flask was added sodium 2-amino-5-cyano-6-methylsulfanyl-pyrimidine-4-thiolate (1.00 g, 4.54 mmol, 1.0 eq.), bromoacetic acid (0.631 g, 4.54 mmol, 1.0 eq.), and benzene (30 mL). Triethylamine (Et₃N, 696 µL, 4.99 mmol, 1.1 eq.) was added and the resulting suspension was stirred at room temperature for 4 h. The suspension was filtered and the solid was diluted with H₂O (100 mL) and EtOAc (100 mL). The organic phase was extracted with saturated aqueous sodium bicarbonate (50 mL). The aqueous phase was washed with EtOAc (2×50 mL). The aqueous phase was collected and then acidified with 1N HCl upon which a white precipitate formed. The aqueous suspension was extracted with EtOAc (2×100 mL). The combined aqueous phases were dried over anhydrous sodium sulfate, filtered. The filtrate was concentrated to ~50 mL upon which a white precipitate was evident. The suspension was filtered to give a white powder (705 mg). The filtrate was concentrated to give a second crop of material as a tan powder (200 mg). Total yield of (2-amino-5-cyano-6-methylsulfanyl-pyrimidin-4-ylsulfanyl)-acetic acid: 905 mg (78%). LC/MSD (BP Series 1100 MSD) Expected MW: 256.01, Observed M−H, 255.0, Retention time: 0.35. ¹H-NMR, DMSO-d6, Varian 400 MHz δ 12.79 (bs, 1H), 7.78 (bs, 2H), 3.93 (s, 2H), 2.52 (s, 3H) ppm.

2-(2-Amino-5-cyano-6-methylsulfanyl-pyrimidin-4-ylsulfanyl)-N-(2-amino-5-trifluoromethyl-phenyl)-acetamide (and regioisomer): To a 25 mL recovery flask was added (2-amino-5-cyano-6-methylsulfanyl-pyrimidin-4-ylsulfanyl)-acetic acid (150 mg, 0.585 mmol, 1.0 eq.), HATU (334 mg, 0.878 mmol, 1.5 eq.), and DMF (5 mL). N-methylmorpholine (129 µL, 1.17 mmol, 2.0 eq.) was added and the resulting solution was stirred for 30 min at room temperature. 3,4-Diaminobenzotrifluoride (206 mg, 1.17 mmol, 2.0 eq.) was added and the reaction mixture was stirred at room temperature overnight. The reaction mixture was diluted with EtOAc (50 mL) and washed with a succession of 10% aqueous LiCl (2×25 mL), H₂O (1×25 mL), and brine (1×25 mL). The combined aqueous phases were extracted with EtOAc (2×25 mL). The combined organic phases were dried over anhydrous sodium sulfate, filtered, and concentrated to give a brown oil. The crude material was purified via flash chromatography (1:1 EtOAc/Hexanes) to give 2-(2-amino-5-cyano-6-methylsulfanyl-pyrimidin-4-ylsulfanyl)-N-(2-amino-5-trifluoromethyl-phenyl)-acetamide (and regioisomer). LC/MSD (HP Series 1100 MSD) Expected MW: 414.05, Observed M+H, 415.0, Retention time: 1.45. Analytical LC: 98%, Retention time: 5.30 (11 minute run). ¹H-NMR, DMSO-d6, Varian 400 MHz δ 9.51-9.43 (m, 1H), 7.49-7.41 (m, 1H), 7.23-7.03 (m, 1H), 6.85-6.80 (m, 1H), 5.63-5.37 (m, 1H), 4.10 (m, 2H) ppm.

2-Amino-4-methylsulfanyl-6-(6-trifluoromethyl-1H-benzoimidazol-2-ylmethylsulfanyl)-pyrimidine-5-carbonitrile:

To a 10 mL recovery flask was added 2-(2-amino-5-cyano-6-methylsulfanyl-pyrimidin-4-ylsulfanyl)-N-(2-amino-5-trifluoromethyl-phenyl)-acetamide (and regioisomer) (10 mg, 0.0241 mmol) and AcOH (2 mL). The solution was stirred at 120° C. for 1 h. The reaction mixture was concentrated. The resulting film was resuspended in 1:1 $CH_3CN/H_2O$ and lyophilized to give 2-amino-4-methylsulfanyl-6-(6-trifluoromethyl-1H-benzoimidazol-2-ylmethylsulfanyl)-pyrimidine-5-carbonitrile as a tan powder (9 mg, 94%). LC/MSD (HP Series 1100 MSD) Expected MW: 396.04, Observed M+H, 397.0, Retention time: 1.49. Analytical LC: 98%, Retention time: 4.46 (11 minute run). $^1$H-NMR, DMSO-d6, Varian 400 MHz δ 12.69 (m, 1H), 8.10 (bs, 1H), 7.91-7.79 (d, 1H), 7.76-7.64 (dd, 1H), 7.51-7.46 (dd, 1H), 4.68 (s, 2H) ppm.

Example 8

Synthesis of 2-[(2-Amino-5-cyano-6-methylsulfanyl-pyrmidin-4-yl)-methyl-amino]-N-(3-trifluoromethyl-phenyl)-acetamide

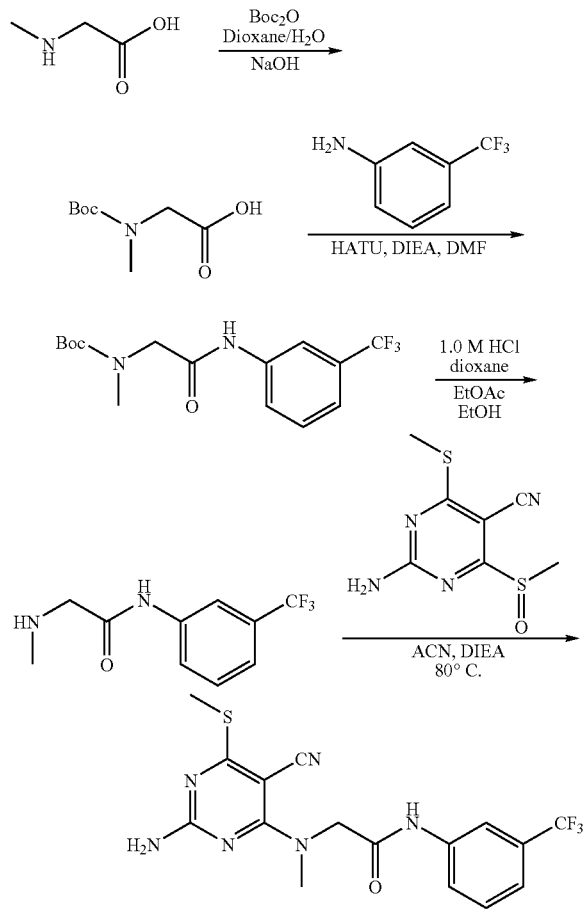

Boc-sarcosine: To a 250 mL round bottom flask containing sarcosine (1.78 g, 20 mmol, 1.0 eq.), $H_2O$ (20 mL), and dioxane (40 mL) was added a solution of sodium hydroxide (3.6 g in 6 mL of $H_2O$, 4.5 eq.). The reaction flask was then cooled to 0° C. before Boc-anhydride (5.2 g, 24.0 mmol, 1.2 eq.) was added in one portion. The reaction was then stirred overnight at RT before concentrating via rotary evaporation to remove dioxane. The remaining aqueous solution was then extracted with EtOAc (40 mL). The EtOAc layer was discarded, and the aqueous layer was acidified with 1N HCl until pH=3. The aqueous layer was then extracted three times with EtOAc. The combined organic layers were then washed with brine, dried with $Na_2SO_4$, and concentrated to yield Boc-sarcosine as a clear oil (3.5 g, 92%). $^1$H-NMR (d6-DMSO): 3.83 (d, 2H), 2.80 (d, 3H), 1.39 (d, 9H) ppm.

Methyl-[(3-trifluoromethyl-phenylcarbamoyl)-methyl]-carbamic acid tert-butyl ester: To a 25 mL round bottomed flask was added Boc-sarcosine (378 mg, 2.0 mmol, 1.0 eq.), DMF (10.0 mL), DIEA (0.35 mL, 2.0 mmol, 2.0 eq.), HATU (836 mg, 2.2 mmol, 2.2 eq.) and 3-trifluoromethylaniline (0.4 mL, 3.0 mmol, 1.5 eq.). The reaction was allowed to stir at RT overnight before quenching with $H_2O$ (20 mL) and EtOAc (100 mL). The organic layer was then washed 2× with 10% LiCl, washed with brine, dried with $Na_2SO_4$, and concentrated to give an oil. Further drying on high vacuum then gave a solid. Column chromatography on silica gel with 60:40 EtOAc:Hex gave methyl-[(3-trifluoromethyl-phenylcarbamoyl)-methyl]-carbamic acid tert-butyl ester (431 mg, 64%). LC/MSD (HP Series 1100 MSD): Expected MW: 332, Observed M−H: 331, Retention time: 1.6 min. $^1$H-NMR (d6-DMSO): 10.35 (d, 1H), 8.10 (d, 1H), 7.75 (dd, 1H), 7.55 (t, 1H), 7.40 (d, 1H), 4.00 (d, 2H), 2.88 (d, 3H), 1.40 (d, 9H) ppm.

2-Methylamino-N-(3-trifluoromethyl-phenyl)-acetamide: In a 25 mL round bottom flask, methyl-[(3-trifluoromethyl-phenylcarbamoyl)-methyl]-carbamic acid tert-butyl ester (400 mg, 1.2 mmol, 1.0 eq.) was dissolved in EtOAc (4.0 mL) and EtOH (1.0 mL) before adding 4 N HCl in dioxane (1.5 mL) dropwise. The reaction was allowed to stir at RT for 2 hr or until reaction is complete as monitored by LC/MS. The white precipitate was filtered and rinsed with EtOAc to give 2-methylamino-N-(3-trifluoromethyl-phenyl)-acetamide as the HCl salt (248 mg, 77%). LC/MSD (HP Series 1100 MSD): Expected MW: 232, Observed M+H, 233.1, Retention time: 0.8 min. $^1$H-NMR (d6-DMSO): 11.2 (s, 1H), 9.00(br s, 2H), 8.10 (s, 1H), 7.80 (d, 1H), 7.61 (t, 1H), 7.49 (d, 1H), 4.00 (s, 2H), 2.65 (s, 3H) ppm.

2-[(2-Amino-5-cyano-6-methylsulfanyl-pyrimidin yl)-methyl-amino]-N-(3-trifluoromethyl-phenyl)-acetamide: In a disposable sealed tube is added 2-amino-4-methanesulfinyl-6-methylsulfanyl-pyrimidine-5-carbonitrile (228 mg, 1.0 mmol, 1.0 eq.), acetonitrile (5.0 mL), DIEA (0.363 mL, 2.25 mmol, 2.25 eq.), and 2-methylamino-N-(3-trifluoromethyl-phenyl)-acetamide (240 mg, 1.0 mmol, 1.0 eq.). The reaction mixture was then heated to 80° C. for 5 hr before cooling to RT. (Note: The reaction was initially heterogeneous, but after heating, became homogeneous within 30 min.) The reaction was then quenched with $H_2O$ (20 mL) and EtOAc (50 mL). The EtOAc layer washed with brine, dried with $Na_2SO_4$, and concentrated to give crude 2-[(2-amino-5-cyano-6-methylsulfanyl-pyrimidin-4-yl)-methyl-amino]-N-(3-trifluoromethyl-phenyl)-acetamide as a solid. The solid was then taken up in 5 mL of 1:1 EtOAc:Hex, sonicated for several minutes, and then filtered and rinsed with 1 mL 1:1 EtOAc:Hex to give pure product acetamide as a white solid (230 mg, 58%). LC/MSD (HP Series 1100 MSD): Expected MW: 396, Observed M+H, 397.1, Retention time: 1.58 min. ANALYTICAL HPLC: >95%, Retention time: 5.37 min (8 minute run). $^1$H-NMR (d6-DMSO): 10.4 (d, 1H), 8.08 (br d, 1H), 7.75 (m, 1H), 7.55 (t, 1H), 7.40 (d, 1H), 7.30-7.10 (br d, 2H), 4.40 (s, 2H), 3.20 (d, 3H), 2.52-2.31 (rotamer doublet, 3H) ppm.

Example 9

Synthesis of 2-(2-Amino-6-chloro-5-formyl-pyrimidin-4-ylamino)-N-(3-trifluoromethyl-phenyl)-acetamide

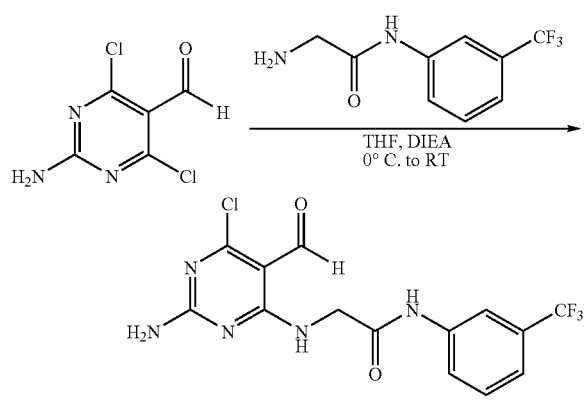

To a 25 mL round bottomed flask cooled to 0° C. was added 2-amino-4,6-di-chloro-5-formyl-pyrimidine (192 mg, 1.0 mmol, 1.0 eq.), THF (10 mL), DIEA (0.34 mL, 2.0 mmol, 2.0 eq.), and 2-amino-N-(3-trifluoromethyl-phenyl)-acetamide (245 mg, 1.0 mmol, 1.0 eq.). The reaction mixture was warmed to RT and allowed to stir overnight before quenching with H₂O (10 mL) and EtOAc (50 mL). The EtOAc layer washed with brine, dried with Na₂SO₄, and concentrated to give crude product as a solid. The solid was then rinsed with 5:95 EtOAc:Hexanes to give pure 2-(2-Amino-6-chloro-5-formyl-pyrimidin-4-ylamino)-N-(3-trifluoromethyl-phenyl)-acetamide as a yellow solid (159 mg, 43%). LC/MSD (HP Series 1100 MSD): Expected MW: 373, Observed M+H, 374.0, Retention time: 1.45 min. ANALYTICAL HPLC: >95%, Retention time: 4.15 min (8 minute run). ¹H-NMR (d6-DMSO): 10.5 (s, 1H), 9.9 (s, 1H), 9.42 (t, 1H), 8.08 (s, 1H), 7.80 (d, 1H), 7.59 (t, 1H), 7.42 (d, 1H), 4.40 (d, 2H) ppm.

Example 10

Synthesis of 2-(6-Amino-1H-pyrazolo[3,4-d]pyrimidin-4-ylamino)-N-(3-trifluoromethyl-phenyl)-acetamide

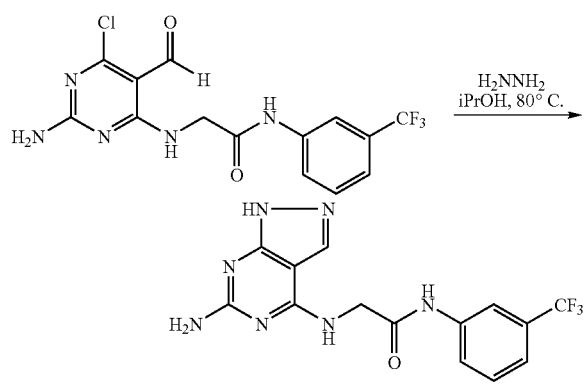

In a disposable sealed tube was added 2-(2-Amino-6-chloro-5-formyl-pyrimidin-4-ylamino)-N-(3-trifluoromethyl-phenyl)-acetamide (96.0 mg, 0.25 mmol, 1.0 eq.), iso-propanol (2.0 mL), and hydrazine monohydrate (0.02 mL, 0.35 mmol, 1.4 eq.). The reaction was sealed and heated to 80° C. After 2 hrs, the reaction was spiked with 0.01 mL of hydrazine monohydrate, resealed, and allowed to continue stirring at 80° C. overnight. The reaction was then cooled to RT and the resulting yellow precipitate was filtered and rinsed with cold EtOH to give crude 2-(6-amino-1H-pyrazolo[3,4-d]pyrimidin-4-ylamino)-N-(3-trifluoromethyl-phenyl)-acetamide. The crude precipitate was then sonicated in 1.0 mL H₂O, filtered, rinsed with an additional 1 mL H₂O, and lyophilized overnight to give pure 2-(6-amino-1H-pyrazolo[3,4-d]pyrimidin-4-ylamino)-N-(3-trifluoromethyl-phenyl)-acetamide as a pale yellow solid (30 mg, 34%). LC/MSD (HP Series 1100 MSD): Expected MW: 351, Observed M+H, 352.1, Retention time: 1.19 min. ANALYTICAL HPLC: >90%, Retention time: 3.58 min (8 minute run). ¹H-NMR (d6-DMSO): 12.5 (br s, 1H), 10.42 (s, 1H), 8.15 (s, 1H), 7.80 (m, 2H), 7.59 (t, 1H), 7.41 (d, 1H), 6.01 (br s, 2H), 4.40 (rotamer d, 2H) ppm.

Example 11

Synthesis of 2-(2-Amino-5-formyl-6-methylsulfanyl-pyrimidin-4-ylamino)-N-(3-trifluoromethyl-phenyl)-acetamide

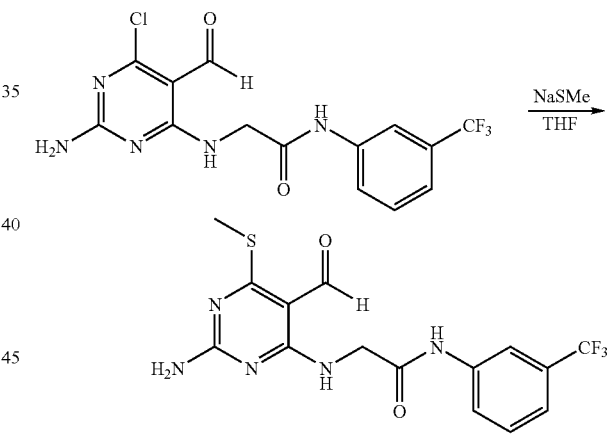

To a round bottom flask is added 2-(2-amino-6-chloro-5-formyl-pyrimidin-4-ylamino)-N-(3-trifluoromethyl-phenyl)-acetamide (80.0 mg, 0.21 mmol, 1.0 eq.), THF (5.0 mL), and DIEA (0.036 mL, 0.21 mmol, 1.0 eq.). The flask was then cooled to 0° C. before adding sodium thiomethoxide (16.0 mg, 0.23 mmol, 1.1 eq.). The reaction was warmed to RT and stirred for 3 hrs before quenching with H₂O (10 mL) and EtOAc (50 mL). The EtOAc layer washed with brine, dried with Na₂SO₄, and concentrated to give pure 2-(2-amino-5-formyl-6-methylsulfanyl-pyrimidin-4-ylamino)-N-(3-trifluoromethyl-phenyl)-acetamide as a yellow solid (75.0 mg, 92%). LC/MSD (HP Series 1100 MSD): Expected MW: 385, Observed M+H, 386.1, Retention time: 1.58 min. ANALYTICAL HPLC: >95%, Retention time: 4.30 min (8 minute run). ¹H-NMR (d6-DMSO): 10.48 (s, 1H), 9.98 (s, 1H), 9.35 (t, 1H), 8.10 (s, 1H), 7.80 (d, 1H), 7.59 (t, 1H), 7.41 (m, 2H), 7.25 (br s, 1H), 4.25 (d, 2H), (3 thiomethyl protons are buried

Example 12

Synthesis of 2-(2-Amino-5-hydroxymethyl-6-methylsulfanyl-pyrimidin-4-ylamino)-N-(3-trifluoromethyl-phenyl)-acetamide

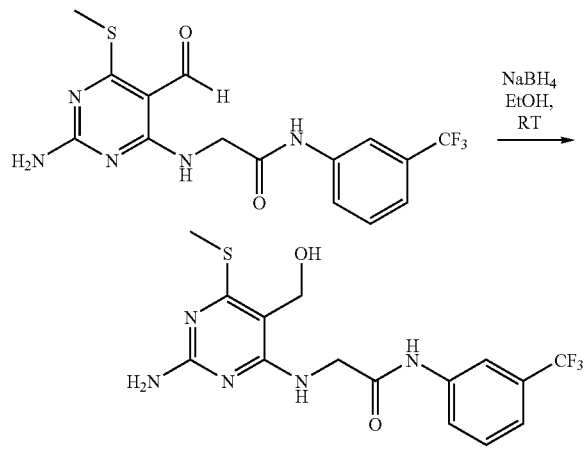

To a 25 mL round bottom flask is added 2-(2-amino-5-formyl-6-methylsulfanyl-pyrmidin-4-ylamino)-N-(3-trifluoromethyl-phenyl)-acetamide (40.0 mg, 0.10 mmol, 1.0 eq.), EtOH (2.0 mL), and sodium borohydride (5.0 mg, 0.13 mmol, 1.3 eq.). The reaction was stirred at RT for 1 hr, concentrated to remove EtOH, and partitioned between $H_2O$ and EtOAc. The aqueous layer was extracted once more with EtOAc. The combined EtOAc layers were then washed with brine, dried with $Na_2SO_4$, and concentrated to give pure 2-(2-amino-5-hydroxymethyl-6-methylsulfanyl-pyrimidin-4-ylamino)-N-(3-trifluoromethyl-phenyl)-acetamide as a white solid (37.0 mg, 95%). LC/MSD (BP Series 1100 MSD): Expected MW: 387, Observed M+H, 388.1, Retention time: 1.35 min. ANALYTICAL HPLC: >94%, Retention time: 2.82 min (8 minute run). $^1$H-NMR (d-MeOH): 8.00 (s, 1H), 7.78 (d, 1H), 7.50 (t, 1H), 7.39 (d, 1H), 4.62 (s, 2H), 4.38 (s, 2H), 2.42 (s, 3H) ppm.

Example 13

Synthesis of 2-[2-Amino-5-(hydroxyimino-methyl)-6-methylsulfanyl-pyrimidin-4-ylamino]-N-(3-trifluoromethyl-phenyl)-acetamide

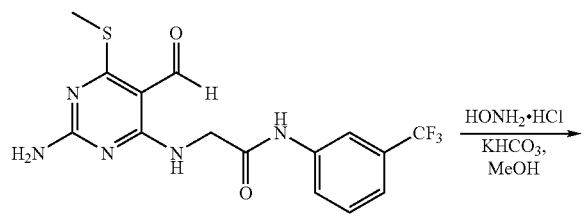

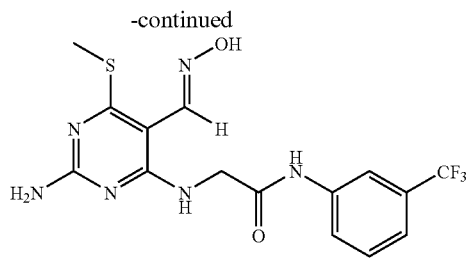

To a round bottom flask was added 2-(2-amino-5-formyl-6-methylsulfanyl-pyrimidin-4-ylamino)-N-(3-trifluoromethyl-phenyl)-acetamide (50.0 mg, 0.13 mmol, 1.0 mmol), MeOH (2.0 mL), potassium bicarbonate (51.0 mg, 0.51 mmol, 4.0 eq.), and hydroxylamine HCl (35.6 mg, 0.51 mmol, 4.0 eq.). The reaction was heated to 60° C. for 72 hrs before quenching with $H_2O$ (10 mL) and EtOAc (50 mL). The EtOAc layer washed with brine, dried with $Na_2SO_4$, and concentrated to give crude 2-[2-amino-5-(hydroxyimino-methyl)-6-methylsulfanyl-pyrimidin-4-ylamino]-N-(3-trifluoromethyl-phenyl)-acetamide as an oil. The product was then precipitated out with 3 mL water and 0.5 mL of ACN, filtered and rinsed with 2 mL of (1:2 ACN: $H_2O$) to give pure 2-[2-amino-5-(hydroxyimino-methyl)-6-methylsulfanyl-pyrimidin-4-ylamino]-N-(3-trifluoromethyl-phenyl)-acetamide as a solid (15.0 mg, 29%). LC/MSD (HP Series 1100 MSD): Expected MW: 400, Observed M+H, 401.1, Retention time: 1.48 min. ANALYTICAL HPLC: >80%, Retention time: 2.89 min (8 minute run). $^1$H-NMR (d6-DMSO): 10.98 (s, 1H), 10.50 (s, 1H), 8.40 (t, 1H), 8.15 (s, 1H), 8.09 (s, 1H), 7.77 (d, 1H), 7.58 (t, 1H), 7.40 (d, 1H), 5.90 (br s, 2H), 4.36 (d, 2H), 2.40 (s, 3H) ppm.

Example 14

Synthesis of 2-(2-Amino-5-hydrazonomethyl-6-methylsulfanyl-pyrimidin-4-ylamino)-N-(3-trifluoromethyl-phenyl)-acetamide

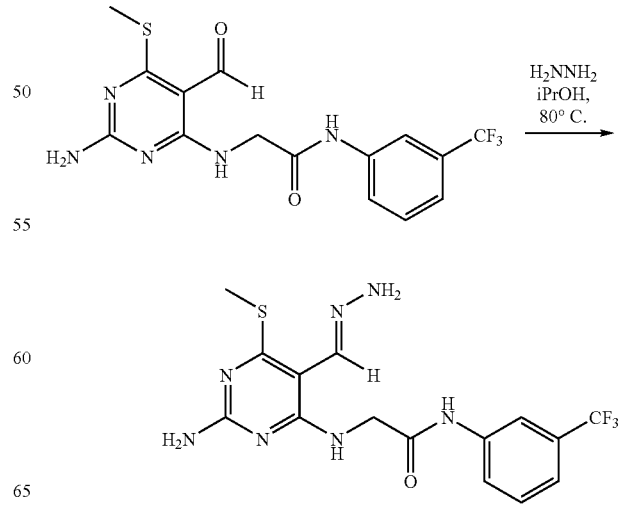

To a disposable sealed tube was added 2-(2-amino-5-formyl-6-methylsulfanyl-pyrimidin-4-ylamino)-N-(3-trifluoromethyl-phenyl)-acetamide (100 mg, 0.25 mmol, 1.0 eq.), isopropanol (4.0 mL), and hydrazine monohydrate (0.048 mL, 0.96 mmol, 3.8 eq.). The tube was sealed and heated to 80° C. overnight. The reaction was then quenched with H₂O (10 mL) and EtOAc (50 mL). The EtOAc layer washed with brine, dried with Na₂SO₄, and concentrated to give crude 2-(2-amino-5-hydrazonomethyl-6-methylsulfanyl-pyrimidin-4-ylamino)-N-(3-trifluoromethyl-phenyl)-acetamide as an oil. The crude product was then precipitated out with 3 mL water and 0.5 mL of ACN, filtered and rinsed with 2 mL of H₂O to give pure 2-(2-amino-5-hydrazonomethyl-6-methylsulfanyl-pyrimidin-4-ylamino)-N-(3-trifluoromethyl-phenyl)-acetamide as a yellow solid (45.0 mg, 45%). LC/MSD (HP Series 1100 MSD): Expected MW: 399, Observed M+H, 400.1, Retention time: 1.43 min. ANALYTICAL HPLC: >90%, Retention time: 3.89 min (8 minute run). ¹H-NMR (d6-DMSO): 10.42 (s, 1H), 9.15 (t, 1H), 8.15 (s, 1H), 8.05 (s, 1H), 7.80 (d, 1H), 7.58 (t, 1H), 7.42 (d, 1H), 6.45 (s, 2H), 5.25 (br s, 2H), 4.30 (d, 2H), 2.40 (s, 3H) ppm.

Example 15

Synthesis of 2S-(2-Amino-5-cyano-6methylsulfanyl-pyrimidin-4-ylamino)-N-(3-trifluoromethyl-phenyl)-propionamide

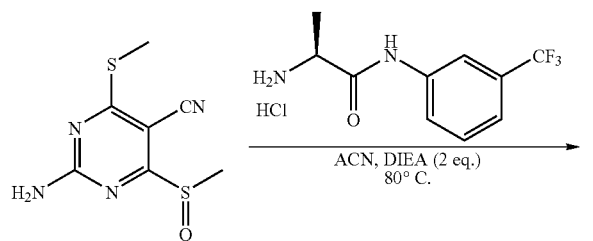

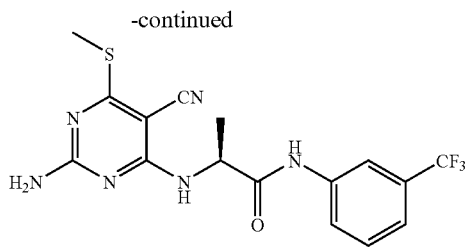
-continued

To a sealed tube was added 2-amino-4-methanesulfinyl-6-methylsulfanyl-pyrimidine-5-carbonitrile (600 mg, 2.6 mmol, 1.0 eq.), acetonitrile (10.0 mL), S-2-amino-N-(3-trifluoromethyl-phenyl)-propionamide (705 mg, 2.6 mmol, 1.0 eq.), and DIEA (0.91 mL, 5.2 mmol, 2.0 eq.). The tube was sealed and heated to 80° C. for 3 hrs, cooled to RT and quenched with EtOAc (150 mL) and H₂O (20 mL). The EtOAc layer washed with brine, dried with Na₂SO₄, and concentrated to give the crude product as an oil. Column chromatography on silica gel with 1:1 EtOAc:Hexanes gave pure 2S-(2-amino-5-cyano-6methylsulfanyl-pyrimidin-4-ylamino)-N-(3-trifluoromethyl-phenyl)-propionamide as an oil that solidified over time (596 mg, 58%). LC/MSD (HP Series 1100 MSD): Expected MW: 396, Observed M+H, 397.1, Retention time: 1.50 min. ANALYTICAL HPLC: >97%, Retention time: 4.01 min (8 minute run). ¹H-NMR (d6-DMSO): 10.42-10.20 (rotamer d, 1H), 8.10 (s, 1H), 7.80 (m, 1H), 7.58 (t, 1H), 7.40 (d, 1H), 7.15 (br s, 2H), 4.49 (m, 1H), 2.36 (s, 3H), 1.42 (d, 3H) ppm.

Example 16

Synthesis of 2S-(2-Amino-5-cyano-6methylsulfinyl-pyrimidin-4-ylamino)-N-(3-trifluoromethyl-phenyl)-propionamide and 2S-(2-Amino-5-cyano-6methylsulfonyl-pyrimidin-4-ylamino)-N-(3-trifluoromethyl-phenyl)-propionamide

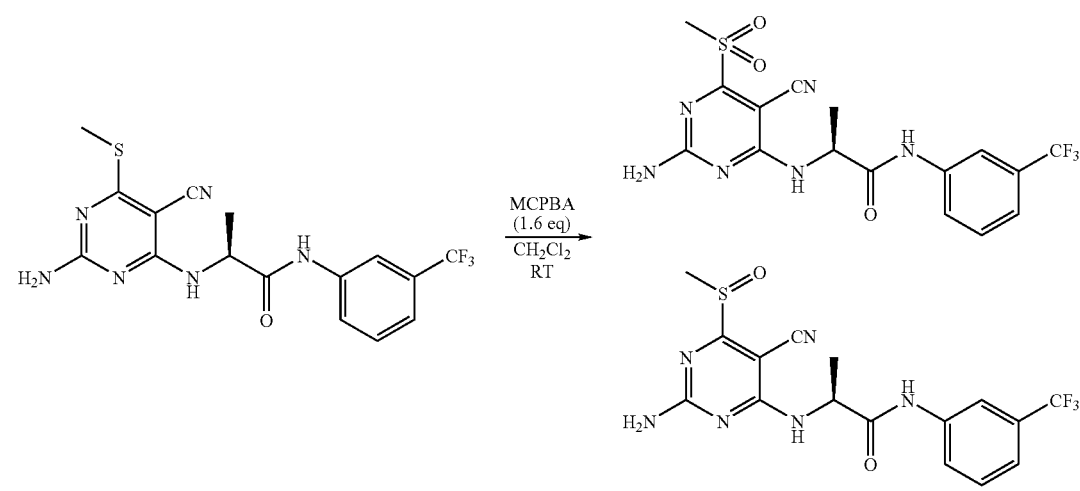

To a round bottom flask was added 2S-(2-amino-5-cyano-6methylsulfanyl-pyrimidin-4-ylamino)-N-(3-trifluoromethyl-phenyl)-propionamide (100 mg, 0.25 mmol, 1.0 eq.), CH$_2$Cl$_2$ (5.0 mL), and MCPBA (68.0 mg, 0.4 mmol, 1.6 eq.). Note, addition of more MCPBA will give a greater ratio of sulfone to sulfoxide. The reaction was stirred at RT for 1 hr before removing CH$_2$Cl$_2$ via rotary evaporation. The solid was then partitioned between EtOAc and sat. NaHCO$_3$. The EtOAc layer washed with brine, dried with Na$_2$SO$_4$, and concentrated to give a mixture of sulfone and sulfoxide as a white solid. Column chromatography on silica gel with 60:40 EtOAc:Hexanes gave pure 2S-(2-Amino-5-cyano-6methyl-sulfinyl-pyrimidin-4-ylamino)-N-(3-trifluoromethyl-phenyl)-propionamide and 2S-(2-Amino-5-cyano-6methylsulfonyl-pyrimidin-4-ylamino)-N-(3-trifluoromethyl-phenyl)-propionamide as white solids with the sulfone eluting before the sulfoxide (sulfone=3 mg, 2.8%, sulfoxide=72 mg, 70%). Sulfone: LC/MSD (BP Series 1100 MSD): Expected MW: 428, Observed M+H, 429.1, Retention time: 1.40 min. ANALYTICAL HPLC: >95%, Retention time: 4.44 min (8 minute run). $^1$H-NMR (d6-DMSO): 10.40-10.24 (rotamer d, 1H), 8.40 (dd, 1H), 8.05 (d, 1H), 7.80 (dd, 1H), 7.55 (m, 1H), 7.40 (d, 1H), 4.49 (m, 1H), (sulfone 3 protons are buried in DMSO peak), 1.42 (d, 3H) ppm. Sulfoxide: LC/MSD (HP Series 1100 MSD): Expected MW: 412, Observed M+H, 413.1, Retention time: 1.30 min. ANALYTICAL HPLC: >95%, Retention time: 3.84 min (8 minute run). $^1$HNMR (d6-DMSO): 10.40-10.24 (rotamer m, 1H), 8.30 (t, 1 H), 8.05 (d, 1H), 7.80 (m, 1H), 7.55 (m, 1H), 7.40 (d, 1H), 4.49 (m, 1H), 2.85-2.65 (rotamer m, 3H), 1.42 (d, 3H) ppm.

Example 17

Synthesis of 2S-(2-Amino-5-cyano-6methoxy-pyrimidin-4-ylamino)-N-(3-trifluoromethyl-phenyl)-propionamide

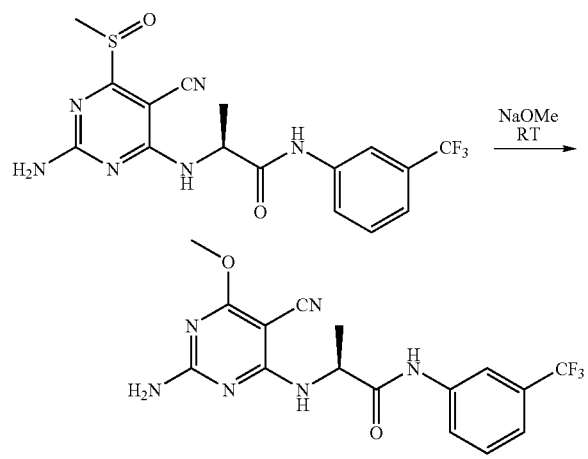

In a round-bottomed flask was added 2S-(2-amino-5-cyano-6methylsulfinyl-pyrimidin-4-ylamino)-N-(3-trifluoromethyl-phenyl)-propionamide (26.0 mg, 0.06 mmol, 1.0 eq.), acetonitrile (3 mL), and 0.5 M sodium methoxide (0.132 mL, 0.066 mmol, 1.1 eq.). The reaction was complete in 15 min, and thus quenched with H$_2$O (5 mL) and EtOAc (25 mL). The EtOAc layer washed with brine, dried with Na$_2$SO$_4$, and concentrated to give crude hydroxymethyl adduct. Column chromatography on silica gel with 1:1 EtOAc:Hexanes gave pure 2S-(2-amino-5-cyano-6methoxy-pyrimidin-4-ylamino)-N-(3-trifluoromethyl-phenyl)-propionamide as a white solid (14 mg, 61%). LC/MSD (HP Series 1100 MSD): Expected MW: 380, Observed M+H: 381, Retention time: 1.43 min. ANALYTICAL HPLC: >94%, Retention time: 3.67 min (8 minute run). $^1$H-NMR (d6-DMSO): 10.42-10.20 (rotamer d, 1H), 8.10 (s, 1H), 7.80 (dd, 1H), 7.69 (m, 1H), 7.58 (t, 1H), 7.40 (d, 1H), 7.15 (br d, 2H), 4.42 (dt, 1H), 3.8 (rotamer d, 3H), 1.42 (d, 3H) ppm.

Example 18

Synthesis of 2-Amino-4-methylsulfanyl-6-[2-oxo-1-(3-trifluoromethyl-phenyl)-pyrrolidin-3-ylsulfanyl]-pyrimidine-5-carbonitrile

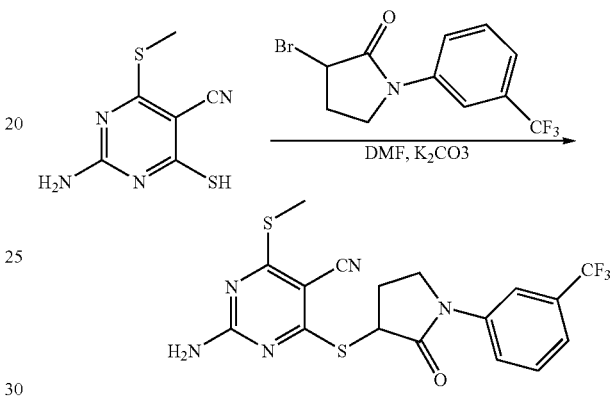

To a round-bottomed flask was added 3-bromo-1-[3-(trifluoromethyl)-phenyl]-pyrrolidin-2-one (21) (308 mg, 1.0 mmol, 1.0 eq.), DMF (3.0 mL), 2-amino-4-mercapto-6-methylsulfanyl-pyrimidine-5-carbonitrile (198 mg, 1.0 mmol, 1.0 eq.), and potassium carbonate (207 mg, 1.5 mmol, 1.5 eq.). The reaction was stirred at RT overnight before quenching with H$_2$O (10 mL) and EtOAc (50 mL). The EtOAc layer washed with 10% LiCl (20 mL, 2×), washed with brine, dried with Na$_2$SO$_4$, and concentrated to give crude product. Pure 2-amino-4-methylsulfanyl-6-[2-oxo-1-(3-trifluoromethyl-phenyl)-pyrrolidin-3-ylsulfanyl]-pyrimidine-5-carbonitrile was precipitated out with 20:80 EtOAc:Hexanes, filtered, and dried under high vacuum (193 mg, 45%). LC/MSD (HP Series 1100 MSD): Expected MW: 425, Observed M+H, 426.1, Retention time: 1.60 min. ANALYTICAL HPLC: >98%, Retention time: 5.56 min (8 minute run). $^1$H-NMR (d6-DMSO): 8.20 (s, 1 H), 7.85 (d, 1H), 7.69 (t, 1H), 7.50 (d, 1H), 4.75 (t, 1H), 4.00 (dt, 2H), 2.72 (m, 1H), 2.40 (s, 3H), 2.39 (m, 1H) ppm.

Example 19

Synthesis of 2-{[2-amino-5-cyano-6-(methylthio)pyrimidin-4-yl]thio}-N-[3-(trifluoromethyl)phenyl]acetamide 5

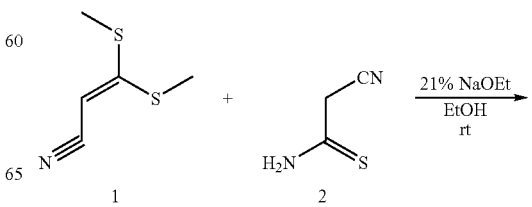

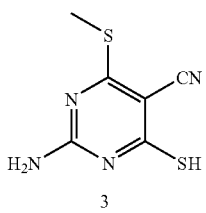

To a 50 mL round-bottom flask were added dimethylcyanodithioiminocarbonate (803 mg, 5.5 mmol), cyanothioacetamide (549 mg, 5.5 mmol) and ethanol (8 mL). Then, sodium ethoxide (21% ethanol solution, 1.8 mL) was added to the reaction mixture at room temperature. After the reaction mixture was stirred for 2 h at room temperature, the precipitate was filtered to give 641 mg (60%) of 2-amino-4-mercapto-6-(methylthio)pyrimidine-5-carbonitrile as a white solid.

LC-MS (ES+) m/z 199.0 (M+1).

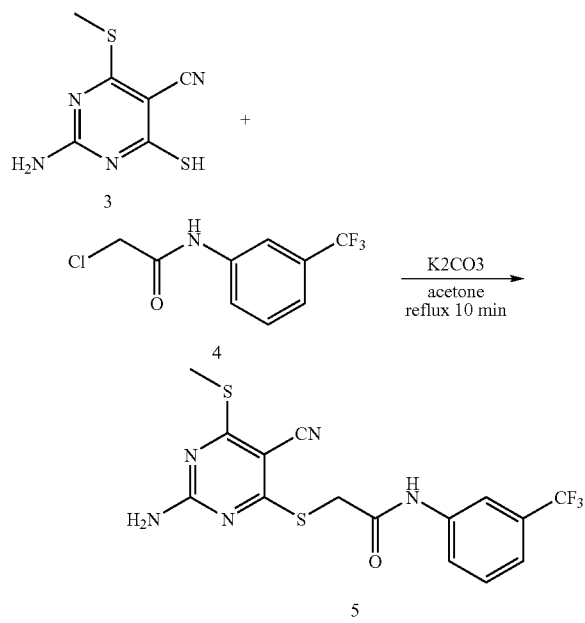

To a 50 mL round-bottomed flask were added 2-amino-4-mercapto-6-(methylthio)-pyrimidine-5-carbonitrile (153 mg, 0.77 mmol, 1.0 eq.), 2-chloro-N-(3-trifluoromethyl-phenyl)acetamide (184 mg, 0.77 mmol), potassium carbonate (106 mg, 0.77 mmol) and acetone (10 mL). The reaction mixture was refluxed for 10 min. After removal of potassium carbonate by filtration, the reaction mixture was concentrated. Recrystallization from ether-ethyl acetate gave 240 mg (80%) of the title compound as a white solid.

$^1$H-NMR (400 MHz, DMSO-$d_6$) δ 10.50 (s, 1H), 8.04(s, 1H), 7.73 (d, 1H), 7.54 (t, 1H), 7.39 (d, 1H), 4.07 (s, 2H), 2.44 (s, 3H); LC-MS (ES+) m/z 400.0 (MH$^+$).

Biochemical Assays

Kinase assays were performed by measurement of incorporation of γ-$^{33}$P ATP into immobilized myelin basic protein (MBP). High binding white 384 well plates (Greiner) were coated with MBP (Sigma #M-1891) by incubation of 60 μl/well of 20 μg/ml MBP in Tris-buffered saline (TBS; 50 mM Tris pH 8.0, 138 mM NaCl, 2.7 mM KCl) for 24 hours at 4° C. Plates were washed 3× with 100 μl TBS. Kinase reactions were carried out in a total volume of 34 μl in kinase buffer (5 mM Hepes pH 7.6, 15 mM NaCl, 0.01% bovine gamma globulin (Sigma #I-5506), 10 mM MgCl$_2$, 1 mM DTT, 0.02% TritonX-100). Compound dilutions were performed in DMSO and added to assay wells to a final DMSO concentration of 1%. Each data point was measured in duplicate, and at least two duplicate assays were performed for each individual compound determination. Enzyme was added to final concentrations of 10 nM or 20 nM, for example. A mixture of unlabeled ATP and γ-$^{33}$P ATP was added to start the reaction (2×10$^6$ cpm of γ-$^{33}$P ATP per well (3000 Ci/mmole) and either 10 μM or 30 μM unlabeled ATP, typically. The reactions were carried out for 1 hour at room temperature with shaking. Plates were washed 7× with TBS, followed by the addition of 50 μl/well scintillation fluid (Wallac). Radioactivity was measured using a Wallac Trilux counter. This is only one format of such assays, various other formats are possible, as known to one of ordinary skill in the art.

The above assay procedure can be used to determine the IC$_{50}$ for inhibition and/or the inhibition constant, K$_i$. The IC$_{50}$ is defined as the concentration of compound required to reduce the enzyme activity by 50% under the conditions of the assay. Exemplary compositions have IC$_{50}$'s of, for example, less than about 100 μM, less than about 10 μM, less than about 1 μM, and further for example having IC$_{50}$'s of less than about 100 nM, and still further, for example, less than about 10 nM. The K$_i$ for a compound may be determined from the IC$_{50}$ based on three assumptions. First, only one compound molecule binds to the enzyme and there is no cooperativity. Second, the concentrations of active enzyme and the compound tested are known (i.e., there are no significant amounts of impurities or inactive forms in the preparations). Third, the enzymatic rate of the enzyme-inhibitor complex is zero. The rate (i.e., compound concentration) data are fitted to equation (1) below; where V is the observed rate, V$_{max}$, is the rate of the free enzyme, I$_0$ is the inhibitor concentration, E$_0$ is the enzyme concentration, and K$_d$ is the dissociation constant of the enzyme-inhibitor complex.

$$V = V_{max}E_0\left[I - \frac{(E_0 + I_0 + K_d) - \sqrt{(E_0 + I_0 + K_d)^2 - 4E_0 I_0}}{2E_0}\right] \quad \text{Equation (1)}$$

Kinase Specific Assays:

Kinase activity and compound inhibition are investigated using one or more of the three assay formats described below. The ATP concentrations for each assay are selected to be close to the Michaelis-Menten constant (K$_M$) for each individual kinase. Dose-response experiments are performed at 10 different inhibitor concentrations in a 384-well plate format. The data are fitted to four-parameter equation (2) below; where Y is the observed signal, X is the inhibitor concentration, Min is the background signal in the absence of enzyme (0% enzyme activity), Max is the signal in the absence of inhibitor (100% enzyme activity), IC$_{50}$ is the inhibitor concentration at 50% enzyme inhibition and H represents the empirical Hill's slope to measure the cooperativity. Typically H is close to unity.

$$Y = \text{Min} + (\text{Max} - \text{Min})/(1 + (X/IC_{50})^H) \quad \text{Equation (2)}$$

p70S6 Kinase Assay

Biochemical activity of p70S6 kinase was assessed using a Luciferase-Coupled Chemiluminescent Kinase assay (LCCA) format. Kinase activity was measured as the percent ATP remaining following the kinase reaction. Remaining ATP was detected by luciferase-luciferin-coupled chemiluminescence. Specifically, the reaction was initiated by mixing test compounds, 5 µM ATP, 5 µM RRRLSSLRA peptide and 12 nM p70S6K (baculovirus expressed human p70S6 kinase domain residues 1-421, containing a T412E mutation) in a 20 uL assay buffer (20 mM Tris-HCL pH 7.5, 10 mM $MgCl_2$, 0.02% Triton X-100, 100 mM DTT, 2 mM $MnCl_2$). The mixture is incubated at ambient temperature for 2 hours after which 20 µL luciferase-luciferin mix is added and the chemiluminescent signal read using a Wallac Victor[2] reader. The luciferase-luciferin mix consists of 50 mM HEPES, pH 7.8, 8.5 µg/mL oxalic acid (pH 7.8), 5 (or 50) mM DTT, 0.4% Triton X-100, 0.25 mg/mL coenzyme A, 63 uM AMP, 28 µg/mL luciferin and 40,000 units/mL luciferase.

Akt1 Kinase Assay

Biochemical activity of Akt1 kinase was assessed using a Luciferase-Coupled Chemiluminescent Kinase assay (LCCA) format. Kinase activity was measured as the percent ATP remaining following the kinase reaction. Remaining ATP was detected by luciferase-luciferin-coupled chemiluminescence. Specifically, the reaction was initiated by mixing test compounds, 1 µM ATP, 5 µM crosstide peptide and 1.3 nM Akt1 (baculovirus expressed human Akt1 kinase domain residues R144-A480, activated with PDK1) in a 20 uL assay buffer (20 mM Tris-HCL pH 7.5, 10 mM MgCl2, 0.01% Triton X-100, 1 mM DTT, 3 mM MnCl2). The mixture is incubated at ambient temperature for 3 hours after which 20 µL luciferase-luciferin mix is added and the chemiluminescent signal read using a Wallac Victor2 reader. The luciferase-luciferin mix consists of 50 mM HEPES, pH 7.8, 8.5 µg/mL oxalic acid (pH 7.8), 5 (or 50) mM DTT, 0.4% Triton X-100, 0.25 mg/mL coenzyme A, 63 uM AMP, 28 µg/mL luciferin and 40,000 units/mL luciferase.

Akt2 Kinase Assay

Biochemical activity of Akt2 kinase was assessed using a Luciferase-Coupled Chemiluminescent Kinase assay (LCCA) format. Kinase activity was measured as the percent ATP remaining following the kinase reaction. Remaining ATP was detected by luciferase-luciferin-coupled chemiluminescence. Specifically, the reaction was initiated by mixing test compounds, 2 µM ATP, 5 µM crosstide peptide and 10 nM Akt2 (baculovirus expressed human Akt2 kinase domain residues K146-R480) in a 20 uL assay buffer (20 mM Tris-HCL pH 7.5, 10 mM MgCl2, 0.03% Triton X-100, 1 mM DTT, 3 mM MnCl2). The mixture is incubated at ambient temperature for 2 hours after which 20 µL luciferase-luciferin mix is added and the chemiluminescent signal read using a Wallac Victor2 reader. The luciferase-luciferin mix consists of 50 mM HEPES, pH 7.8, 8.5 µg/mL oxalic acid (pH 7.8), 5 (or 50) mM DTT, 0.4% Triton X-100, 0.25 mg/mL coenzyme A, 63 uM AMP, 28 µg/mL luciferin and 40,000 units/mL luciferase.

PDK1 Kinase Assay

Biochemical activity of PDK1 kinase was assessed using a Luciferase-Coupled Chemiluminescent Kinase assay (LCCA) format. Kinase activity was measured as the percent ATP remaining following the kinase reaction. Remaining ATP was detected by luciferase-luciferin-coupled chemiluminescence. Specifically, the reaction was initiated by mixing test compounds, 0.5 µM ATP, 0.6 µM PDKtide peptide and 6 nM PDK1 (baculovirus expressed human PDK1 kinase domain residues M51-T359) in a 20 uL assay buffer (20 mM Hepes pH 7.5, 1 mM CaCl2, 0.03% CHAPS, 2 mM DTT). The mixture is incubated at ambient temperature for 3 hours after which 20 µL luciferase-luciferin mix is added and the chemiluminescent signal read using a Wallac Victor2 reader. The luciferase-luciferin mix consists of 50 mM HEPES, pH 7.8, 8.5 µg/mL oxalic acid (pH 7.8), 5 (or 50) mM DTT, 0.4% Triton X-100, 0.25 mg/mL coenzyme A, 63 uM AMP, 28 µg/mL luciferin and 40,000 units/mL luciferase.

Structure Activity Relationships

Table 2 shows structure activity relationship data for selected compounds of the invention. Inhibition is indicated as $IC_{50}$ with the following key: $A=IC_{50}$ less than 50 nM, $B=IC_{50}$ greater than 50 nM, but less than 500 nM, $C=IC_{50}$ greater than 500 nM, but less than 2000 nM, and $D=IC_{50}$ equal to, or greater than 2,000 nM.

TABLE 2

| Entry | Name | p70S6K | Akt-1 | PDK-1 |
|---|---|---|---|---|
| 1 | 2-[(3-cyano-4,6-dimethyl-5-nitropyridin-2-yl)oxy]-N-[3-(trifluoromethyl)phenyl]acetamide | A | D | D |
| 2 | $N^2$-(2-amino-6-chloropyrimidin-4-yl)-N-[3-(trifluoromethyl)phenyl]glycinamide | A | D | D |
| 3 | [2-amino-6-(methylthio)pyrimidin-4-yl]methyl ]3-(trifluoromethyl)phenyl]carbamate | A | D | |
| 4 | 2-{[2-amino-5-cyano-6-(methylthio)pyrimidin-4-yl]thio}-N-[5-(trifluoromethyl)pyridin-2-yl]acetamide | A | D | D |
| 5 | $N^2$-[2-amino-6-(methylthio)pyrimidin-4-yl]-N-[3-(trifluoromethyl)phenyl]glycinamide | A | D | D |
| 6 | 2-{[2-amino-6-(methylthio)pyrimidin-4-yl]oxy}-N-[3-(trifluoromethyl)phenyl]acetamide | A | D | D |
| 7 | 2-{[2-amino-5-cyano-6-(methylthio)pyrimidin-4-yl]thio}-N-[3-(methyloxy)phenyl]acetamide | A | D | D |
| 8 | $N^2$-(2-amino-6-morpholin-4-ylpyrimidin-4-yl)-N-[3-(trifluoromethyl)phenyl]glycinamide | A | | D |
| 9 | 2-{]2-amino-5-cyano-6-(methylthio)pyrimidin-4yl]thio}-N-(4-chlorophenyl)acetamide | A | D | D |
| 10 | 2-{[2-amino-6-(1H-1,2,3-benzotriazol-1-yloxy)pyrimidin-4-yl]thio}-N-[3-(trifluoromethyl)phenyl]acetamide | A | D | D |
| 11 | 2-{[2-amino-5-cyano-6-(methylthio)pyrimidin-4-yl]thio}-N-(3-chlorophenyl)acetamide | A | D | |
| 12 | $N^2$-(2-amino-6-chloro-5-formylpyrimidin-4-yl)-N-[3-(trifluoromethyl)phenyl]glycinamide | A | D | D |
| 13 | $N^2$-[2-amino-5-formyl-6-(methylthio)pyrimidin-4-yl]-N-[3-(trifluoromethyl)phenyl]glycinamide | B | D | D |

TABLE 2-continued

| Entry | Name | p70S6K | Akt-1 | PDK-1 |
|---|---|---|---|---|
| 14 | 2-{[2-amino-5-cyano-6-(methylthio)pyrimidin-4-yl]oxy}-N-[3-(trifluoromethyl)phenyl]acetamide | B | D | D |
| 15 | 2-[(2-amino-6-chloropyrimidin-4-yl)thio]-N-[3-(trifluoromethyl)phenyl]acetamide | B | D | |
| 16 | 2-{[-amino-5-cyano-6-(methylthio)pyrimidin-4-yl]thio}-N-methyl-N-[3-(trifluoromethyl)phenyl]acetamide | B | D | D |
| 17 | N²-[4-amino-6-(methylthio)-1,3,5-triazin-2-yl]-N-[3-(trifluoromethyl)phenyl]glycinamide | B | D | D |
| 18 | N²-[4-(dimethylamino)-6-(methylthio)-1,3,5-triazin-2-yl]-N-[3-(trifluoromethyl)phenyl]glycinamide | B | D | |
| 19 | N²-[4-(methylamino)-6-(methylthio)-1,3,5-triazin-2-yl]-N-[3-(trifluoromethyl)phenyl]glycinamide | B | D | |
| 20 | N²-[2-amino-5-cyano-6-(methylthio)pyrimidin-4-yl]-N-[3-(trifluoromethyl)phenyl]glycinamide | B | D | D |
| 21 | 2-{[2-amino-5-cyano-6-(methylthio)pyrimidin-4-yl]thio}-N-[3-(trifluoromethyl)phenyl]acetamide | A | D | D |
| 22 | 2-{[2-amino-5-cyano-6-(methylthio)pyrimidin-4-yl]thio}-N-[3-(butyloxy)phenyl]acetamide | A | D | D |
| 23 | 2-{[2-amino-5-cyano-6-(methylthio)pyrimidin-4-yl]thio}-N-1,3-benzothiazol-2-ylacetamide | A | D | |
| 24 | 2-{[2-amino-5-cyano-6-(methylthio)pyrimidin-4-yl]thio}-N-(5-ethyl-1,3,4-thiadiazol-2-yl)acetamide | A | D | D |
| 25 | 2-{[2-amino-5-cyano-6-(methylthio)pyrimidin-4-yl]thio}-N-(4-methyl-1,3-thiazol-2-yl)acetamide | A | D | D |
| 26 | 2-amino-4-{[2-(3,5-dimethyl-1H-pyrazol-1-yl)-2-oxoethyl]thio}-6-(methylthio)pyrimidine-5-carbonitrile | A | D | D |
| 27 | 2-{[2-amino-5-cyano-6-(methylthio)pyrimidin-4-yl]thio}-N-1,3-thiazol-2-ylacetamide | A | D | D |
| 28 | ethyl 5-[({[2-amino-5-cyano-6-(methylthio)pyrimidin-4-yl]thio}acetyl)amino]-4-cyano-3-methylthiophene-2-carboxylate | A | D | D |
| 29 | 2-{[2-amino-5-cyano-6-(methylthio)pyrimidin-4-yl]thio}-N-pyridin-2-ylacetamide | A | D | D |
| 30 | 2-amino-4-({2-[2,5-bis(methyloxy)phenyl]-2-oxoethyl}thio)-6-(methylthio)pyrimidine-5-carbonitrile | A | D | D |
| 31 | 2-{[2-amino-5-cyano-6-(methylthio)pyrimidin-4-yl]thio}-N-[4-fluoro-3-(triuoromethyl)phenyl]acetamide | A | D | D |
| 32 | 2-[(2,6-diaminopyrimidin-4-yl)thio]-N-[4-fluoro-3-(trifluoromethyl)phenyl]acetamide | A | D | D |
| 33 | 2-[(2,6-diaminopyrimidin-4-yl)thio]-N-[3-(trifluoromethyl)phenyl]acetamide | A | D | D |
| 34 | 2-{[2-amino-5-cyano-6-(methylthio)pyrimidin-4-yl]thio}-N-[4-chloro-3-(trifluoromethyl)phenyl]acetamide | A | D | D |
| 35 | 2-amino-4-(methylthio)-6-({2-oxo-1-[3-(trifluoromethyl)phenyl]pyrrolidin-3-yl}thio)pyrimidine-5-carbonitrile | A | D | D |
| 36 | 2-{[2-amino-5-cyano-6-(methylthio)pyrimidin-4-yl]thio}-N-[6-(trifluoromethyl)pyridin-2-yl]acetamide | A | D | D |
| 37 | 2-{[2-amino-5-cyano-6-(methylthio)pyrimidin-4-yl]thio}-N-[4-(trifluoromethyl)pyridin-2-yl]acetamide | A | D | D |
| 38 | {6-(methylthio)-2-[(phenylmethyl)amino]pyrimidin-4-yl}methyl [3-(trifluoromethyl)phenyl]carbamate | A | D | D |
| 39 | [6-(methylamino)-2-(methylthio)pyrimidin-4-yl]methyl [3-(trifluoromethyl)phenyl]carbamate | A | D | D |
| 40 | {2-(methylthio)-6-[(phenylmethyl)amino]pyrimidin-4-yl}methyl [3-(trifluoromethyl)phenyl]carbamate | A | D | D |
| 41 | 2-{[2-(acetylamino)-5-cyano-6-(methylthio)pyrimidin-4-yl]thio}-N-[3-(trifluoromethyl)phenyl]acetamide | B | | |
| 42 | (2S)-2-{[2-amino-5-cyano-6-(methylthio)pyrimidin-4-yl]oxy}-N-[3-(trifluoromethyl)phenyl]propanamide | B | | |
| 43 | 2-[(2-amino-6-chloro-5-formylpyrimidin-4-yl)thio]-N-[3-(trifluoromethyl)phenyl]acetamide | B | D | |
| 45 | 2-{[2-amino-5-formyl-6-(methylamino)pyrimidin-4-yl]thio}-N-[3-(trifluoromethyl)phenyl]acetamide | B | | |
| 46 | 2-{[2-amino-5-formyl-6-(methylthio)pyrimidin-4-yl]oxy}-N-[3-(trifluoromethyl)phenyl]acetamide | B | | |
| 47 | 2-{[4-amino-6-(methylthio)-1,3,5-triazin-2-yl]oxy}-N-[3-(trifluoromethyl)phenyl]acetamide | B | | |
| 48 | 2-{[2-amino-6-(methylthio)pyrimidin-4-yl]thio}-N-[3-(trifluoromethyl)phenyl]acetamide | B | | |
| 49 | 2-amino-4-(methylthio)-6-{[2-oxo-2-(3-oxo-3,4-dihydro-2H-1,4-benzoxazin-6-yl)ethyl]thio}pyrimidine-5-carbonitrile | B | D | D |
| 50 | 2-[(2-amino-6-chloro-5-formylpyrimidin-4-yl)oxy]-N-[3-(trifluoromethyl)phenyl]acetamide | B | | |
| 51 | 2-{[2-amino-5-formyl-6-(phenylthio)pyrimidin-4-yl]thio}-N-[3-(trifluoromethyl)phenyl]acetamide | B | | |
| 52 | 2-{[µ-amino-5-(hydroxymethyl)-6-(phenylthio)pyrimidin-4-yl]thio}-N-[3-(trifluoromethyl)phenyl]acetamide | B | | |

TABLE 2-continued

| Entry | Name | p70S6K | Akt-1 | PDK-1 |
|---|---|---|---|---|
| 53 | 2-{[2-amino-5-cyano-6-(methylthio)pyrimidin-4-yl]thio}-N-[2-methyl-3-(trifluoromethyl)phenyl]acetamide | C | | |
| 54 | 2-{[2-mino-5-cyano-6-(methylthio)pyrimidin-4-yl]thio}-N-[2-(methyloxy)-5-(trifluoromethyl)phenyl]acetamide | C | | |
| 55 | 2-{[2-amino-5-cyano-6-(methylthio)pyrimidin-4-yl]thio}-N-[2-chloro-5-(trifluoromethyl)phenyl]acetamide | C | | |
| 56 | 2-{[2-amino-5-(hydroxymethyl)-6-(methylthio)pyrimidin-4-yl]oxy}-N-[3-(trifluoromethyl)phenyl]acetamide | C | | |
| 57 | $N^2$-(6-amino-1H-pyrazolo[3,4-d]pyrimidin-4-yl)-N-[3-(trifluoromethyl)phenyl]glycinamide | C | | |
| 58 | $N^2$-[2-amino-5-[(E)-hydrazonomethyl]-6-(methylthio)pyrimidin-4-yl]-N-[3-(trifluoromethyl)phenyl]glycinamide | C | | |
| 59 | $N^2$-[2-amino-5-[(E)-(hydroxymino)methyl]-6-(methylthio)pyrimidin-4-yl]-N-[3-(trifluoromethyl)phenyl]glycinamide | C | | |
| 60 | $N^2$-[2-amino-5-cyano-6-(methylthio)pyrimidin-4-yl]-N-[3-(trifluoromethyl)phenyl]-L-alaninamide | C | | |
| 61 | 2-{[2-amino-5-cyano-6-(methylamino)pyrimidin-4-yl]thio}-N-[3-(trifluoromethyl)phenyl]acetamide | C | | |
| 62 | 2-{[2-amino-5-cyano-6-(methylthio)pyramidin-4-yl[thio}-N-[2-amino-5-(trifluoromethyl)phenyl]acetamide | C | | |
| 63 | 2-amino-4-(methylthio)-6-({[6-(trifluoromethyl)-1H-benzimidazol-2-yl]methyl}thio)pyrimidine-5-carbonitrile | C | | |
| 64 | 2-[2-amino-5-cyano-6-(methylthio)pyrimidin-4-yl]-N-[3-(trifluoromethyl)phenyl]hydrazinecarboxamide | C | | |
| 65 | $N^2$-[5-cyano-2-(methylamino)-6-(methylthio)pyrimidin-4-yl]-N-[3-(trifluoromethyl)phenyl]glycinamide | C | | |
| 66 | 2-{[2-amino-5-cyano-6-(dimethylamino)pyrimidin-4-yl]thio}-N-[3-(trifluoromethyl)phenyl]acetamide | C | | |
| 67 | (S)-1-[2-amino-5-cyano-6-(methythio)pyrimidin-4-yl]-N-[3-(trifluoromethyl)phenyl]prolinamide | C | | |
| 68 | (2R)-2-{[2-amino-5-cyano-6-(methylthio)pyrimidin-4-yl]oxy}-N-[3-(trifluoromethyl)phenyl]propanamide | C | | |
| 69 | 1-{[2-amino-5-cyano-6-(methylthio)pyrimidin-4-yl]oxy}-N-[3-(trifluoromethyl)phenyl]cyclopropanecarboxamide | C | | |
| 70 | (2S)-2-{[2-amino-5-cyano-6-(methylthio)pyrimidin-4-yl]oxy}-3-methyl-N-[3-(trifluoromethyl)phenyl]butanamide | D | | |
| 71 | $N^2$-[5-cyano-2-(dimethylamino)-6-(methylthio)pyrimidin-4-yl]-N-[3-(trifluoromethyl)phenyl]glycinamide | D | | |
| 72 | $N^2$-[2-amino-5-cyano-6-(methylthio)pyrimidin-4-yl]-$N^2$-methyl-N-[3-(trifluoromethyl)phenyl]glycinamide | D | | |
| 73 | 1-{[2-amino-5-cyno-6-(methylthio)pyrimidin-4-yl]amino}-N-[3-(trifluoromethyl)phenyl]cyclopropanecarboxamide | D | | |
| 74 | $N^2$-[2-amino-5-cyano-6-(methylsulfinyl)pyrimidin-4-yl]-N-[3-(trifluoromethyl)phenyl]-L-alaninamide | D | | |
| 75 | $N^2$-[2-amino-5-cyano-6-(methylsulfonyl)pyrimidin-4-yl]-N-[3-(trifluoromethyl)phenyl]-L-alaninamide | D | | |
| 76 | $N^2$-(5-cyano-2-morpholin-4-ylpyrimidin-4-yl)-N-]3-(trifluoromethyl)phenyl]glycinamide | D | | |
| 77 | 2-{[2-amino-5-cyano-6-(methylthio)pyrimidin-4-yl]thio}-N-[3,5-bis(trifluoromethyl)phenyl]acetamide | D | | |
| 78 | $N^2$-[2-amino-5-cyano-6-(methyloxy)pyrimidin-4-yl]-N-[3-(trifluoromethyl)phenyl]-L-alaninamide | D | | |
| 79 | $N^2$-[2-amino-5-cyano-6-(methylthio)pyrimidin-4-yl]-N-[2-(methyloxy)-5-(trifluoromethyl)phenyl]-L-alaninmide | D | | |
| 80 | $N^2$-[2-amino-5-cyano-6-(methylthio)pyrimidin-4-yl]-N-[2-5-(trifluoromethyl)phenyl]-L-alaninamide | D | | |
| 81 | $N^2$-[2-amino-5-cyano-6-(methylthio)pyrimidin-4-yl]-2-methyl-N-[3-(trifluoromethyl)phenyl]alaninamide | D | | |
| 82 | $N^2$-[2-amino-5-cyano-6-(methylthio)pyrimidin-4-yl]-N-{3-[(4-methylpiperazin-1-yl)carbonyl]phenyl}-L-alaninamide | D | | |
| 83 | $N^2$-[2-amino-5-cyano-6-(methylthio)pyrimidin-4-yl]-N-[3-(trifluoromethyl)phenyl]-D-alaninamide | D | | |
| 84 | 2-[(2-amino-5-cyano-6-morpholin-4-ylpyrimidin-4-yl)thio]-N-[3-(trifluoromethyl)phenyl]acetamide | D | | |
| 85 | (R)-1-[2-amino-5-cyano-6-(methylthio)pyrimidin-4-yl]-N-[3-(trifluoromethyl)phenyl]prolinamide | D | | |
| 86 | $N^2$-[2-amino-5-cyano-6-(methylthio)pyrimidin-4-yl]-N-[3-(trifluoromethyl)phenyl]-L-ornithinamide | D | | |
| 87 | $N^2$-[2-amino-5-cyano-6-(methylthio)pyrimidin-4-yl]-$N^2$-[2-(dimethylamino)ethyl]-N-[3-(trifluoromethyl)phenyl]glycinamide | D | | |
| 88 | $N^2$-[2-amino-5-cyano-6-(ethyloxy)pyrimidin-4-yl]-N-[3-(trifluoromethyl)phenyl]-L-alaninamide | D | | |
| 89 | $N^2$-(2,6-diamino-5-cyanopyrimidin-4-yl)-N-[3-(trifluoromethyl)phenyl]-L-alaninamide | D | | |
| 90 | $N^2$-(2-amino-5-cyanopyrimidin-4-yl)-N-[3-(trifluoromethyl)phenyl]-L-alaninamide | D | | |

TABLE 2-continued

| Entry | Name | p70S6K | Akt-1 | PDK-1 |
|---|---|---|---|---|
| 91 | $N^2$-[2-amino-5-cyano-6-(methylthio)pyrimidin-4-yl]-$N^2$-methyl-N-[3-(trifluoromethyl)phenyl]-L-alaninamide | D | | |
| 92 | $N^2$-[2-amino-5-cyano-6-(methylthio)pyrimidin-4-yl]-N-(3-{[2-(diethylamino)ethyl]oxy}phenyl)-L-alaninamide | D | | |
| 93 | 2-[2-amino-5-cyano-6-(methylthio)pyrimidin-4-yl]-1,2-dimethyl-N-[3-(trifluoromethyl)phenyl]hydrazinecarboxamide | D | | |
| 94 | $N^2$-[2-amino-5-cyano-6-(methylthio)pyrimidin-4-yl]-N-[3-amino-5-(trifluoromethyl)phenyl]-L-alaninamide | D | | |
| 95 | ethyl[1-[2-amino-5-cyano-6-(methylthio)pyrimidin-4-yl]-2-({[3-(trifluoromethyl)phenyl]amino}carbonyl)hydrazino]acetate | D | | |
| 96 | 2-[2-amino-5-cyano-6-(methylthio)pyrimidin-4-yl]-2-methyl-N-[3-(trifluoromethyl)phenyl]hydrazinecaboxamide | D | | |
| 97 | 3,5-diamino-4,6-dimethyl-N-[3-(trifluoromethyl)phenyl]furo[2,3-b]pyridine-2-carboxamide | D | | |
| 98 | 3-amino-4,6-dimethyl-5-nitro-N-[3-(trifluoromethyl)phenyl]furo[2,3-b]pyridine-2-carboxamide | D | | |
| 99 | $N^2$-(2-amino-5-cyano-6-hydroxypyrimidin-4-yl)-N-[3-(trifluoromethyl)phenyl]-L-alaninamide | D | | |
| 100 | $N^2$-[5-cyano-2-(methylthio)pyrimidin-4-yl]-N-[3-(trifluoromethyl)phenyl]glycinamide | D | D | |
| 101 | $N^2$-[2-amino-5-cyano-6-(methylthio)pyrimidin-4-yl]-$N^2$-(tetrahydro-2H-pyran-4-ylmethyl)-N-[3-(trifluoromethyl)phenyl]glycinamide | D | D | |
| 102 | $N^2$-(2-amino-5-cyano-6-{[2-(dimethylamino)ethyl]oxy}pyrimidin-4-yl)-N-[3-(trifluoromethyl)phenyl]-L-alaninamide | D | | |
| 103 | $N^2$-[2-amino-5-cyano-6-(methylthio)pyrimidin-4-yl]-N-6-{[(1,1-dimethylethyl)oxy]carbonyl}-N-[3-(trifluoromethyl)phenyl]-L-lysinamide | D | | |
| 104 | 2-amino-4-(methylthio)-6-(methyl{(1S)-1-[6-(trifluoromethyl)-1H-benzimidazol-2-yl]ethyl}amino)pyrimidine-5-carbonitrile | D | | |
| 105 | $N^2$-[2-amino-5-cyano-6-(methylthio)pyrimidin-4-yl]-$N^2$-[2-(tetrahydro-2H-pyran-4yl)ethyl]-N-[3-(trifluoromethyl)phenyl]glycinamide | D | | |
| 106 | $N^2$-[2-amino-5-cyano-6-(methylthio)pyrimidin-4-yl]-N-[3-{[2-(diethylamino)ethyl]amino}-5-(trifluoromethyl)phenyl]-L-alaninamide | D | | |
| 107 | 2-amino-4-(methylthio)-6-({(1S)-1-[6-(trifluoromethyl)-1H-benzimidazol-2-yl]ethyl}amino)pyrimidine-5-carbonitrile | D | | |
| 108 | 2-{2-amino-5-cyano-6[1-(3-trifluoromethyl-phenylcarbamoyl)-1S-ethylamino]-pyrimidin-4-ylamino}N-(3-trifluoromethyl-phenyl)-2S-propionamide | D | | |
| 109 | $N^2$-[2-amino-5-cyano-6-(methylthio)pyrimidin-4-yl]-$N^2$-methyl-N-(3-methylphenyl)glycinamide | D | | |
| 110 | $N^2$-[2-amino-5-cyano-6-(methylthio)pyrimidin-4-yl]-$N^2$-methyl-N-[3-(1-methylethyl)phenyl]glycinamide | D | | |
| 111 | $N^2$-[2-amino-5-cyano-6-(methylthio)pyrimidin-4-yl]-$N^5$-[imino(nitroamino)methyl]-N-[3-(trifluoromethyl)phenyl]-L-ornithinamide | D | | |
| 112 | methyl 3-({N-[2-amino-5-cyano-6-(methylthio)pyrimidin-4-yl]-L-alanyl}amino)-5-(trifluoromethyl)benzoate | D | D | |
| 113 | $N^2$-[2-amino-5-cyano-6-(methylthio)pyrimidin-4-yl]-N-(3-nitrophenyl)-L-alaninamide | D | | |
| 114 | $N^2$-[2-amino-5-cyano-6-(methylthio)pyrimidin-4-yl]-N-[3-(trifluoromethyl)phenyl]-L-lysinamide | D | | |
| 115 | $N^2$-[2-amino-5-cyano-6-(propyloxy)pyrimidin-4-yl]-N-[3-(trifluoromethyl)phenyl]-L-alaninamide | B | | |
| 116 | $N^2$-[5-cyano-2-{[2-(methyloxy)ethyl]amino{-6-(methylthio)pyrimidin-4-yl]-N-[3-(trifluoromethyl)phenyl]-L-alaninamide | D | | |
| 117 | $N^2$-[2-amino-5-cyano-6-(methylthio)pyrimidin-4-yl]-N-[3-(trifluoromethyl)phenyl]-L-argininamide | D | | |
| 118 | $N^2$-[2-amino-5-cyano-6(methylsulfinyl)pyrimidin-4-yl]-$N^2$-methyl-N-[3-(trifluoromethyl)phenyl]-L-alaninamide | D | | |
| 119 | $N^2$-[2-amino-5-cyano-6-(methyloxy)pyrimidin-4-yl]-$N^2$-methyl-N-[3-(trifluoromethyl)phenyl]-L-alaninamide | D | | |
| 120 | $N^2$-[2-amino-5-cyano-6-(propyloxy)pyrimidin-4-yl]-$N^2$-methyl-N-[3-(trifluoromethyl)phenyl]-L-alaninamide | D | | |
| 121 | $N^2$-[2-amino-5-cyano-6-(ethyloxy)pyrimidin-4-yl]-$N^2$-methyl-N-[3-(trifluoromethyl)phenyl]-L-alaninamide | D | | |
| 122 | $N^2$-{2-amino-5-cyano-6-[(1-methylethyl)oxy]pyrimidin-4-yl}-N-[3-(trifluoromethyl)phenyl]-L-alaninamide | D | | |
| 123 | $N^5$-acetyl-$N^2$-[2-amino-5-cyano-6-(methylthio)pyrimidin-4-yl]-N-[3-(trifluoromethyl)phenyl]-L-ornithinamide | D | | |
| 124 | $N^2$-[2-amino-5-cyano-6-(methylthio)pyrimidin-4-yl]-N-(3-aminophenyl)-L-alaninamide | D | | |

TABLE 2-continued

| Entry | Name | p70S6K | Akt-1 | PDK-1 |
|---|---|---|---|---|
| 125 | 3-({N-[2-amino-5-cyano-6-(methylthio)pyrimidin-4-yl]-L-alanyl}amino)-N-[2-(dimethylamino)ethyl]-5-(trifluoromethyl)benzamide | D | | |
| 126 | 2-(methyloxy)ethyl ((4S)-4-{[2-amino-5-cyano-6-(methylthio)pyrimidin-4-yl]amino}-5-oxo-5-{[3-(trifluoromethyl)phenyl]amino}pentyl)carbamate | D | | |
| 127 | 2-[2-amino-5-cyano-6-(ethyloxy)pyrimidin-4-yl]-N-[3-(trifluoromethyl)phenyl]hydrazinecarboxamide | D | | |
| 128 | 1,1-dimethylethyl((4S)-4-{[2-amino-5-cyano-6-(ethyloxy)pyrimidin-4-yl]amino}-5-oxo-5-{[3-(trifluoromethyl)phenyl]amino}pentyl)carbamate | D | | |
| 129 | N$^2$-[2-amino-5-cyano-6-(ethyloxy)pyrimidin-4-yl]-N-[3-(trifluoromethyl)phenyl]-L-ornithinamide | D | D | D |
| 130 | 3-({N-[2-amino5-cyano-6-(methylthio)pyrimidin-4-yl]-N-methyl-L-alanyl}amino)-N-[2-(dimethylamino)ethyl]-5-(trifluoromethyl)benzamide | A | D | D |
| 131 | 3-({N-[2-amino-5-cyano-6-(methylthio)pyrimidin-4-yl]-N-methyl-L-alanyl}amino)-N-[3-(4-methylpiperazin-1-yl)propyl]-5-(trifluoromethyl)benzamide | A | D | D |
| 132 | N~2~-[2-amino-5-cyano-6-(methylthio)pyrimidin-4-yl]-N~2~-methyl-N-{3-[(trifluoromethyl)oxy]phenyl}-L-alaninamide | A | D | D |
| 133 | N~2~-[2-amino-5cyano-6-(methylthio)pyrimidin-4-yl]-N-(3-bromophenyl)-N~2~-methyl-L-alaninamide | A | D | D |
| 134 | N~2~-[2-amino-5-cyano-6-(methylthio)pyrimidin-4-yl]-N-{2-{[2-(dimethylamino)ethyl]oxy}-5-[(trifluoromethyl)oxy]phenyl}-N~2~-methyl-L-alaninamide | A | D | D |
| 135 | 3-({N-[2-amino-5-cyano-6-(methylthio)pyrimidin-4-yl]-N-methyl-L-alanyl]amino)-N-(2-morpholin-4-ylethyl)-5-(trifluoromethyl)benzamide | A | D | D |
| 136 | N~2~-[2-amino-5-cyano-6-(ethyloxy)pyrimidin-4-yl]-N~2~-methyl-N-[3-(trifluoromethyl)phenyl]-L-lysinamide | A | D | D |
| 137 | N~2~-[2-amino-5-cyano-6-(methylthio)pyrimidin-4-yl]-N-[3-{[2-(dimethylamino)ethyl]oxy}-5-(trifluoromethyl)phenyl]-L-alaninamide | A | D | D |
| 138 | (2S0-2-{[2-amino-5-cyano-6-(methylthio)pyrimidin-4-yl]amino}-3-oxo-3-{[3-(trifluoromethyl)phenyl]amino}propyl acetate | B | D | D |
| 139 | N~2~-2-amino-5-cyano-6-(methylthio)pyrimidin-4-yl]-N~1~-[3-(trifluoromethyl)phenyl]-L-glutamamide | B | | |
| 140 | 2-[2-amino-5-cyano-6-(methyloxy)pyrimidin-4-yl]-N-[3-(trifluoromethyl)phenyl]hydrazinecarboxamide | B | D | D |
| 141 | 3-({N-[2-amino-5-cyano-6-(methylthio)pyrimidin-4yl]-L-alanyl}amino)-N-hydroxy-5-(trifluoromethyl)benzamide | B | D | D |
| 142 | N~2~-[2-amino-5-cyano-6-(methylthio)pyrimidin-4-yl]-3-(dimethylamino)-N-[3-(trifluoromethyl)phenyl]-L-alaninamide | B | D | D |
| 143 | N~2~-[2-amino-5-cyano-6-(methylthio)pyrimidin-4-yl]-5-morpholin-4-yl-N-[3-(trifluoromethyl)phenyl]-L-norvalinamide | B | | |
| 144 | N~2~-[2-amino-5-cyano-6-(methylthio)pyrimidin-4-yl]-N~5~-[2-(methyloxy)ethyl]-N-[3-(trifluoromethyl)phenyl]-L-ornithinamide | C | | |
| 145 | 3-({N-[2-amino-5-cyano-6-(methylthio)pyrimidin-4-yl]-L-alanyl{amino)-5-(trifluoromethyl)benzoic acid | C | | |
| 146 | methyl N~2~-[2-amino-5-cyano-6-(methylthio0pyrimidin-4-yl]-N-'-(trifluoromethyl)phenyl]-L-alpha-glutaminate | C | | |
| 147 | N~5~-(aminocarbonyl)-N~2~-[2-amino-5-cyano-6-(methylthio)pyrimidin-4-yl]-N-[3-(trifluoromethyl)phenyl]-L-omithinamide | C | D | |
| 148 | N~2~-[2-amino-5-cyano-6-(ethyloxy)pyrimidin-4-yl]-N-[3-(trifluoromethyl)phenyl]-L-omithinamide | C | D | |
| 149 | N~2~-[2-amino-5-cyano-6-(methylthio)pyrimidin-4-yl]-N-[3-(trifluoromethyl)phenyl]-Lalpha-glutamine | C | | |
| 150 | N~2~-[2-amino-5-cyano-6-(ethyloxy)pyrimidin-4-yl]-N-[3-(trifluoromethyl)phenyl]-L-serinamide | C | | |
| 151 | N~2~-[2-amino-5-cyano-6-(ethyloxy)pyrimidin-4-yl]-O-(phenylmethyl)-N-[3-(trifluoromethyl)phenyl]-L-serinamide | D | | |
| 152 | N~2~-[2-amino-5-cyano-6-(ethyloxy)pyrimidin-4-yl]-N-[3-(trifluoromethyl)phenyl]-L-argininamide | D | | |
| 153 | N~2~-[2-amino-5-cyano-6-(methylthio)pyrimidin-4-yl]-N~2~-methyl-N~6~-{[(phenylmethyl)oxy]carbonyl}-N-[3-(trifluoromethyl)phenyl]-L-lysinamide | D | | |
| 154 | Nalpha-[2-amino-5-cyano-6-(ethyloxy)pyrimidin-4-yl]-N-[3-(trifluoromethyl)phenyl]-L-tyrosinamide | D | | |
| 155 | N~5~-[2-amino-5-cyano-6-(methylthio)pyrimidin-4-yl]-N-[3-(trifluoromethyl)phenyl]-L-ornithinamide | D | | |
| 156 | N~2~-[2-amino-5-cyano-6-(ethyloxy)pyrimidin-4-yl]-N~6~,N~6~-dimethyl-N-[3-(trifluoromethyl)phenyl]-L-lysinamide | D | | |
| 157 | N~2~-[2-amino-5-cyano-6-(ethyloxy)pyrimidin-4-yl]-N-[3-[(4-methylpiperazin-1-yl)carbonyl]-5-(trifluoromethyl)phenyl]-L-alaninamide | D | | |

TABLE 2-continued

| Entry | Name | p70S6K | Akt-1 | PDK-1 |
|---|---|---|---|---|
| 158 | 3-({N-[2-amino-5-cyano-6-(ethyloxy)pyrimidin-4-yl]-L-alanyl}amino)-N-(3-pyrrolidin-1-ylpropyl)-5-(trifluoromethyl)benzamide | D | | |
| 159 | 3-({N-[2-amino-5-cyano-6-(ethyloxy)pyrimidin-4-yl]-L-alanyl}amino)-N-(2-morpholin-4-ylethyl)-5-(trifluoromethyl)benzamide | D | | |
| 160 | 3-({N-[2-amino-5-cyano-6-(ethyloxy)pyrimidin-4-yl]-L-alanyl}amino)-N-[2-(dimethylamino)ethyl]-5-(trifluoromethyl)benzamide | D | D | |
| 161 | 3-({N-[2-amino-5-cyano-6-(ethyloxy)pyrimidin-4-yl]-L-alanyl{amino)-N-[3-(4-methylpiperazin-1-yl)propyl]-5-(trifluoromethyl)benzamide | D | | |
| 162 | N~2~-[2-amino-5-cyano-6-(ethyloxy)pyrimidin-4-yl]-N~2~-methyl-N~6~-{[(phenylmethyl)oxy]carbonyl}-N-[3-(trifluoromethyl)phenyl]-L-lysinamide | D | | |
| 163 | 1,1-dimethylethyl ((4S)-4-{[2-amino-5-cyano-6-(ethyloxy)pyrimidin-4-yl]amino}-5-oxo-5-{[3-(triflouromethyl)phenyl]amino}pentyl)carbamate | D | | |
| 164 | (2S)-2-{[2-amino-5-cyano-6-(ethyloxy)pyrimidin-4-yl]amino}-3-oxo-3-{[3-(trifluoromethyl)phenyl]amino}propyl acetate | D | | |
| 165 | phenylmethyl N~2~-[2-amino-5-cyano-6-(ethyloxy)pyrimidin-4-yl]-N-[3-(trifluoromethyl)phenyl]-L-apha-glutaminate | D | | |
| 166 | N~2~,N~5~-diacetyl-N~2~-[2-(acetylamino)-5-cyano-6-(methylthio)pyrimidin-4-yl]-N-[3-(trifluoromethyl)phenyl]-L-ornithinamide | D | | |
| 167 | 2-(methyloxy)ethyl ((4S)-4-{[2-amino-5-cyano-6-(methylthio)pyrimidin-4-yl]amino}-5-oxo-5-{[3-(trifluoromethyl)phenyl]amino}pentyl)carbamate | D | | |
| 168 | N~2~-[2-amino-5-cyano-6-(ethyloxy)pyrimidin-4-yl]-5-morpholin-4-yl-N-[3-(trifluoromethyl)phenyl]-L-norvalinamide | D | | |
| 169 | N-((4S)-4-{[2-amino-5-cyano-6-(ethyloxy)pyrimidin-4-yl]amino}-5-oxo-5-{[3-(trifluoromethyl)phenyl]amino}pentyl)-N,N-dimethylmethanaminium | D | | |
| 170 | Methyl N~2~-[2-amino-5-cyano-6-(ethyloxy)pyrimidin-4-yl]-N-[3-(trifluoromethyl)phenyl]-L-alpha-glutaminate | D | | |
| 171 | N~2~-[2-amino-5-cyano-6-(methylthio)pyrimidin-4-yl]-N~6~,N~6~-dimethyl-N-[3-(trifluoromethyl)phenyl]-L-lysinamide | D | | |
| 172 | N~2~-[2-amino-5-cyano-6-(ethyloxy)pyrimidin-4-yl]-N~2~-methyl-N-{3-[(trifluoromethyl)oxy]phenyl}-L-alaninamide | D | D | |
| 173 | N~2~-[2-amino-5-cyano-6-(ethyloxy)pyrimidin-4-yl]-N-[3-(trifluoromethyl)phenyl]-L-alpha-glutamine | D | | |
| 174 | N~2~-[2-amino-5-cyano-6-(ethyloxy)pyrimidin-4-yl]-N-(3-bromophenyl)-N~2~-methyl-L-alaninamide | D | | |
| 175 | N~2~-[2-amino-5-cyano-6-(ethyloxy)pyrimidin-4-yl]-N~1~-[3-(trifluoromethyl)phenyl]-L-glutamamide | D | | |
| 176 | N~2~-[2-amino-5-cyano-6-(ethyloxy)pyrimidin-4-yl]-3-(dimethylamino)-N-[3-(trifluoromethyl)phenyl]-L-alaninamide | D | | |
| 177 | Structure possibly contains amino acid derivative which is not supported in current version! | D | | |
| 178 | N~2~-[2-amino-5-cyano-6-(methyloxy)pyrimidin-4-yl]-3-(dimethylamino)-N-[3-(trifluoromethyl)phenyl]-L-alaninamide | D | | |
| 179 | N~2~-[2-amino-5-cyano-6-(methyloxy)pyrimidin-4-yl]-N-[3-{[2-(dimethylamino)ethyl]oxy}-5-(trifluoromethyl)phenyl]-L-alaninamide | D | | |
| 180 | N~2~-[2-amino-5-cyano-6-(ethyloxy)pyrimidin-4-yl]-N-[3-{[2-(dimethylamino)ethyl]oxy}-5-(trifluoromethyl)phenyl]-L-alaninamide | D | | |
| 181 | N~2~-[2-amino-5-cyano-6-(methyloxy)pyrimidin-4-yl]-N-(3-bromophenyl)-N~2~-methyl-L-alaninamide | D | | |
| 182 | phenylmethyl N~2~-[2-amino-5-cyano-6-(methylthio)pyrimidin-4-yl]-N-[3-(trifluoromethyl)phenyl]-L-alpha-glutaminate | D | | |
| 183 | N~2~-[2-amino-5-cyano-6-(methylthio)pyrimidin-4-yl]-O-(phenylmethyl)-N-[3-(trifluoromethyl)phenyl]-L-serinamide | D | | |
| 184 | N~2~-[2-amino-5-cyano-6-(methylthio)pyrimidin-4-yl]-N~5~,N~5~-bis[2-(methyloxy)ethyl]-N-[3-(trifluoromethyl)phenyl]-L-ornithinamide | D | | |
| 185 | 1,1-dimethylethyl ((4S)-4-{[2-amino-5-cyano-6-(methyloxy)pyrimidin-4-yl]amino}-5-oxo-5-{[3-(trifluoromethyl)phenyl]amino}pentyl)carbamate | D | | |
| 186 | N~5~-acetyl-N~2~-[2-amino-5-cyano-6-(ethyloxy)pyrimidin-4-yl]-N-[3-(trifluoromethyl)phenyl]-L-ornithinamide | D | | |
| 187 | N~5~-acetyl-N~2~-[2-amino-5-cyano-6-(methylthio)pyrimidin-4-yl]-N-[3-(trifluoromethyl)phenyl]-L-ornithinamide | D | | |
| 188 | N~2~-[2-amino-5-cyano-6-(methyloxy)pyrimidin-4-yl]-N~2~-methyl-N-{3-[(trifluoromethyl)oxy]phenyl}-L-alaninamide | D | | |
| 189 | methyl 3-({N-[2-amino-5-cyano-6-(methyloxy)pyrimidin-4-yl]-L-alanyl}amino)-5-(trifluoromethyl)benzoate | D | | |

TABLE 2-continued

| Entry | Name | p70S6K | Akt-1 | PDK-1 |
|---|---|---|---|---|
| 190 | 3-({N-[2-amino-5-cyano-6-(methyloxy)pyrimidin-4-yl]-L-alanyl}amino)-N-[2-(dimethylamino)ethyl]-5-(trifluoromethyl)benzamide | D | | |
| 191 | N~2~-[2-amino-5-cyano-6-(methylthio)pyrimidin-4-yl]-3-morpholin-4-yl-N-[3-(trifluoromethyl)phenyl]-L-alaninamide | D | | |
| 192 | N~2~-[2-amino-5-cyano-6-(methyloxy)pyrimidin-4-yl]-3-morpholin-4-yl-N-[3-(trifluoromethyl)phenyl]-L-alaninamide | D | | |
| 193 | N~2~-[2-amino-5-cyano-6-(ethyloxy)pyrimidin-4-yl]-3-morpholin-4-yl-N-[3-(trifluoromethyl)phenyl]-L-alaninamide | D | | |
| 194 | N~5~-(aminocarbonyl)-N~2~-[2-amino-5-cyano-6-(ethyloxy)pyrimidin-4-yl]-N-]3-(trifluoromethyl)phenyl]-L-ornithinamide | D | D | |
| 195 | N~2~-[2-amino-5-cyano-6-(methylthio)pyrimidin-4-yl]-N-]3-(trifluoromethyl)phenyl]-D-lysinamide | D | D | |
| 196 | N~2~-[2-amino-5-cyano-6-(ethyloxy)pyrimidin-4-yl]-N-[3-(trifluoromethyl)phenyl]-D-lysinamide | D | D | |
| 197 | N~2~-[2-amino-5-cyano-6-(ethyloxy)pyrimidin-4-yl]-O-methyl-N-[3-(trifluoromethyl)phenyl]-L-serinamide | D | | |
| 198 | N~2~-[2-amino-5-cyano-6-(methylthio)pyrimidin-4-yl]-N~5~-(methylsulfonyl)-N-[3-(trifluoromethyl)phenyl]-L-ornithinamide | D | | |

What is claimed is:

1. A compound according to Formula III,

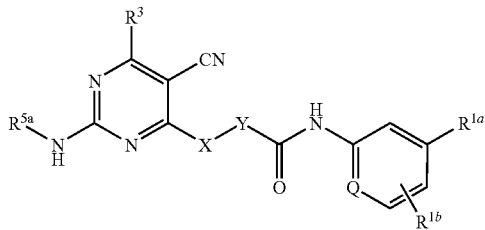

III or a pharmaceutically acceptable salt thereof, wherein:

$R^{1a}$ is selected from halogen, lower perfluoroalkyl, —$NO_2$, and optionally substituted $C_{1-4}$alkyl;

and $R^{1b}$ is selected from halogen, —$N(R^5)R^5$, —$SR^5$, perfluoroalkyl, and optionally substituted lower alkyl;

$R^3$ is independently selected from —H, halogen, trihalomethyl, —CN, —$NO_2$, —$OR^5$, —$N(R^5)OR^5$, —$ON(R^5)R^5$, —$N(R^5)N(R^5)R^5$, —$N(R^5)R^5$, —$S(O)_{0-2}R^5$, —$SO_2N(R^5)R^5$, —$CO_2R^5$, —$C(O)N(R^5)R^5$, —$N(R^5)SO_2R^5$, —$N(R^5)C(O)R^5$, —$N(R^5)CO_2R^5$, —$C(O)R^5$, —$C(=NR^7)N(R^5)R^5$, —$C(=NR^7)R^5$, —$C(=NR^7)OR^5$, —$N(R^5)C(=NR^7)N(R^5)R^5$, optionally substituted lower alkyl, optionally substituted lower alkenyl, optionally substituted lower alkynyl, optionally substituted aryl, optionally substituted heterocyclyl, optionally substituted heterocyclylalkyl, and optionally substituted arylalkyl;

$R^{5a}$ is H;

each $R^5$ is independently selected from —H, optionally substituted lower alkyl, optionally substituted aryl, optionally substituted lower arylalkyl, optionally substituted heterocyclyl, and optionally substituted lower heterocyclylalkyl; or two of $R^5$, together with the atom or respective atoms to which they are attached, can combine to form an optionally substituted three- to seven-membered heterocyclic;

each $R^6$ is independently selected from —H, halogen, trihalomethyl, —CN, —$NO_2$, —$NH_2$, —$OR^5$, —$N(R^5)R^5$, —$S(O)_{0-2}R^5$, —$SO_2N(R^5)R^5$, —$CO_2R^5$, —$C(O)N(R^5)R^5$, —$N(R^5)SO_2R^5$, —$N(R^5)C(O)R^5$, —$N(R^5)CO_2R^5$, —$C(O)R^5$, optionally substituted lower alkyl, optionally substituted aryl, optionally substituted heterocyclyl, optionally substituted heterocyclylalkyl, and optionally substituted arylalkyl; or two of $R^6$, together with the atom or atoms to which they are attached, can combine to form one of an optionally substituted three to seven-membered alicylic, and an optionally substituted three to seven-membered heteroalicylic;

each $R^7$ is independently selected from —H, —CN, —$NO_2$, —$N(R^5)R^5$, —$OR^5$, —$S(O)_{0-2}R^5$, —$SO_2N(R^5)R^5$, —$CO_2R^5$, optionally substituted lower alkyl, optionally substituted lower alkenyl, and optionally substituted lower alkynyl; or $R^5$ and $R^7$, together with the atom or atoms to which they are attached, can combine to form a five- to seven-membered optionally substituted heterocyclyl;

each of X and Y is independently selected from —C(=O)—, —C($R^6$)$R^6$—, —O—, —N($R^5$)—, —C(=$NR^7$)—, and —S(O)$_{0-2}$—; provided when X is —O— or —N($R^5$)—, then Y cannot contain phenyl, napthyl, cyclohexyl, dihydronapthyl tetrahydronapthyl, or a five- to six-membered heteroaryl, each optionally substituted; and Q is either =N— or =C(H)—.

2. The compound according to claim 1, wherein $R^{1a}$ is selected from —$NO_2$, halogen, perfluoroalkyl, haloalkyl, and optionally substituted $C_{1-2}$alkyl.

3. The compound according to claim 2, wherein $R^3$ is selected from optionally substituted —O—$C_{1-4}$alkyl, —O—$C_{1-4}$perfluoroalkyl, optionally substituted —N(H)$C_{1-4}$alkyl, optionally substituted —N($C_{1-4}$alkyl)$C_{1-4}$alkyl, optionally substituted —S(O)$_{0-2}$—$C_{1-4}$alkyl, and optionally substituted —S(O)$_{0-2}$—$C_{1-4}$perfluoroalkyl.

4. The compound according to claim 3, wherein Y is either —N(H)— or —C($R^6$)$R^6$—.

5. The compound according to claim 4, wherein X is selected from —O—, —N($R^5$)— and —S—.

6. The compound according to claim 5, wherein Y is —C($R^6$)$R^6$—; wherein each $R^6$ is independently selected from —H, halogen, trihalomethyl, —$NH_2$, optionally substituted —O—$C_{1-4}$alkyl, optionally substituted —N(H)$C_{1-4}$alkyl, optionally substituted —S—$C_{1-4}$alkyl, optionally substituted lower alkyl, optionally substituted heterocyclyl, and optionally substituted heterocyclylalkyl.

7. The compound according to claim 6, wherein Y is —C(H)R[6]—; wherein R[6] is independently selected from —H, halogen, trihalomethyl, —NH$_2$, optionally substituted —O—C$_{1-4}$alkyl, optionally substituted —N(H)C$_{1-4}$alkyl, optionally substituted —S—C$_{1-4}$alkyl, optionally substituted lower alkyl, optionally substituted heterocyclyl, and optionally substituted heterocyclylalkyl.

8. The compound according to claim 7, wherein Q is =C(H)—.

9. The compound according to claim 1, wherein R$^{1a}$ is selected from halo, lower perfluoroalkyl, —NO$_2$, and optionally substituted C$_{1-4}$alkyl.

10. A compound selected from Table 3:

TABLE 3

| Entry | Name | Structure |
|---|---|---|
| 5 | N$^2$-[2-amino-6-(methylthio)pyrimidin-4-yl]-N-[3-(trifluoromethyl)phenyl]glycinamide | 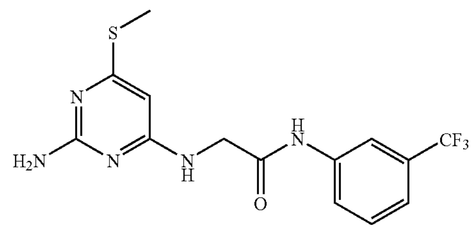 |
| 7 | 2-{[2-amino-5-cyano-6-(methylthio)pyrimidin-4-yl]thio}-N-[3-(methyloxy)phenyl]acetamide | 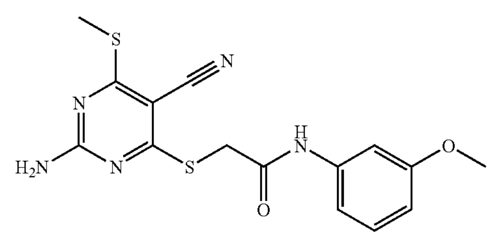 |
| 9 | 2-{[2-amino-5-cyano-6-(methylthio)pyrimidin-4-yl]thio}-N-(4-chlorophenyl)acetamide | 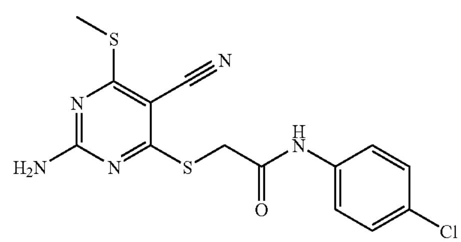 |
| 11 | 2-{[2-amino-5-cyano-6-(methylthio)pyrimidin-4-yl]thio}-N-(3-chlorophenyl)acetamide | 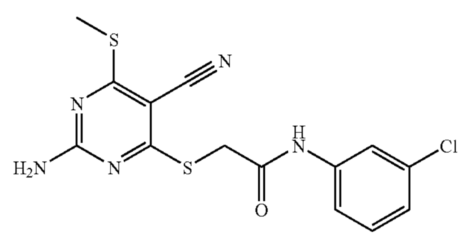 |
| 14 | 2-[2-amino-5-cyano-6-(methylthio)pyrimidin-4-yl]oxy}-N-[3-(trifluoromethyl)phenyl]acetamide | 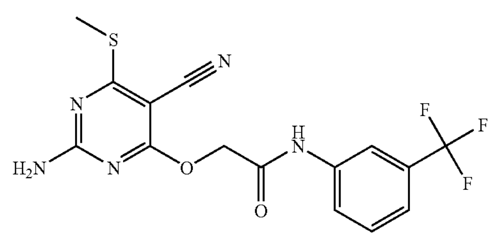 |
| 16 | 2-{[2-amino-5-cyano-6-(methylthio)pyrimidin-4-yl]thio}-N-methyl-N-[3-(trifluoromethyl)phenyl]acetamide | 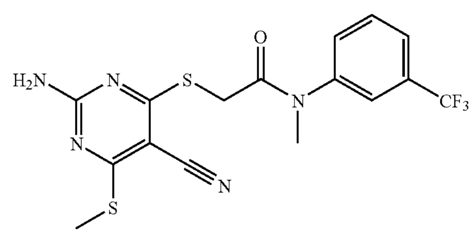 |

TABLE 3-continued

| Entry | Name | Structure |
|---|---|---|
| 20 | N²-[2-amino-5-cyano-6-(methylthio)pyrimidin-4-yl]-N-[3-(trifluoromethyl)phenyl]glycinamide | 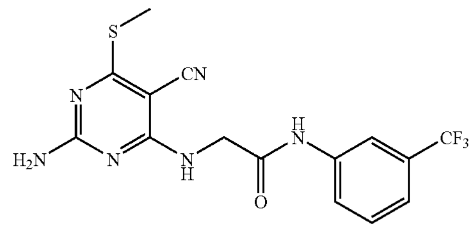 |
| 30 | 2-amino-4-({2-[2,5-bis(methyloxy)phenyl]-2-oxoethyl}thio)-6-(methylthio)pyrimidine-5-carbonitrile | 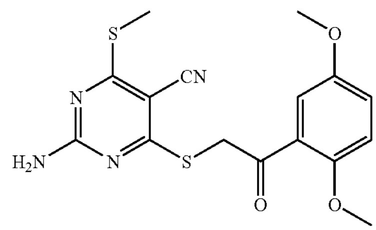 |
| 31 | 2-{[2-amino-5-cyano-6-(methylthio)pyrimidin-4-yl]thio}-N-[4-fluoro-3-(trifluoromethyl)phenyl]acetamide | 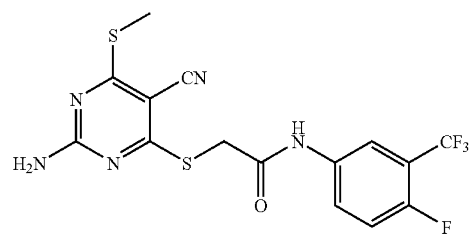 |
| 34 | 2-{[2-amino-5-cyano-6-(methylthio)pyrimidin-4-yl]thio}-N-[4-chloro-3-(trifluoromethyl)phenyl]acetamide | 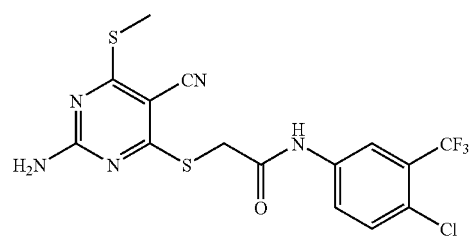 |
| 35 | 2-amino-4-(methylthio)-6-({2-oxo-1-[3-(trifluoromethyl)phenyl]pyrrolidin-3-yl}thio)pyrimidine-5-carbonitrile | 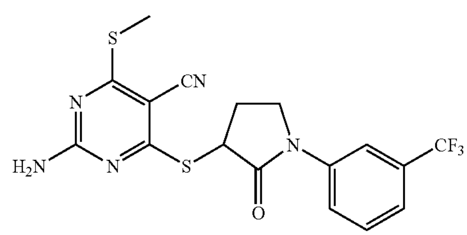 |
| 36 | 2-{[2-amino-5-cyano-6-(methylthio)pyrimidin-4-yl]thio}-N-[6-(trifluoromethyl)pyridin-2-yl]acetamide | 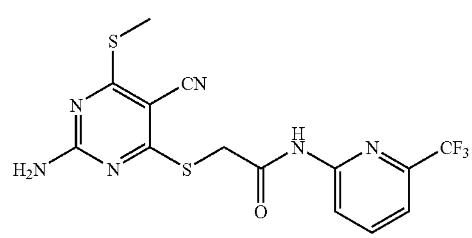 |

TABLE 3-continued

| Entry | Name | Structure |
|---|---|---|
| 37 | 2-{[2-amino-5-cyano-6-(methylthio)pyrimidin-4-yl]thio}-N-[4-(trifluoromethyl)pyridin-2-yl]acetamide | 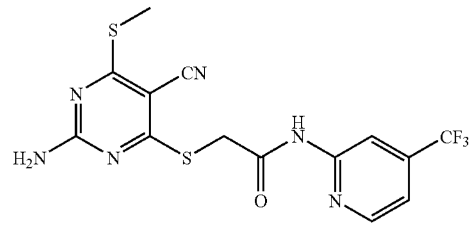 |
| 41 | 2-{[2-(acetylamino)-5-cyano-6-(methylthio)pyrimidin-4-yl]thio}-N-[3-(trifluoromethyl)phenyl]acetamide | 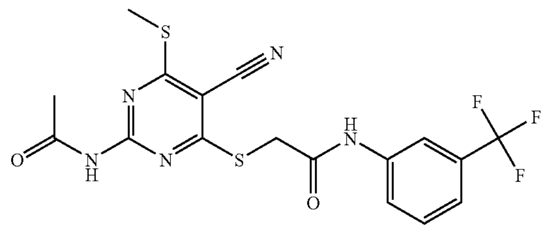 |
| 42 | (2S)-2-{[2-amino-5-cyano-6-(methylthio)pyrimidin-4-yl]oxy}-N-[3-(trifluoromethyl)phenyl]propanamide | 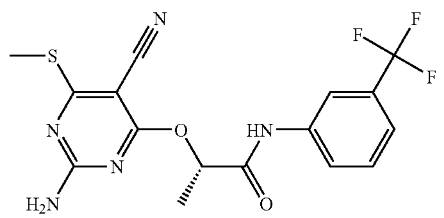 |
| 46 | 2-{[2-amino-5-formyl-6-(methylthio)pyrimidin-4-yl]oxy}-N-[3-(trifluoromethyl)phenyl]acetamide | 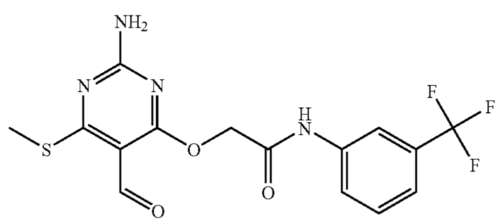 |
| 54 | 2-{[2-amino-5-cyano-6-(methylthio)pyrimidin-4-yl]thio}-N-[2-(methyloxy)-5-(trifluoromethyl)phenyl]acetamide | 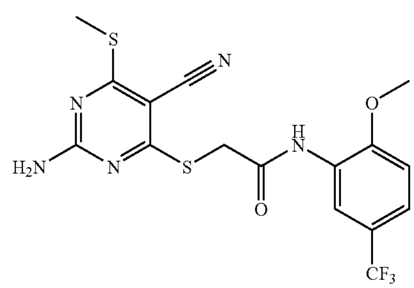 |
| 55 | 2-{[2-amino-5-cyano-6-(methylthio)pyrimidin-4-yl]thio}-N-[2-chloro-5-(trifluoromethyl)phenyl]acetamide | 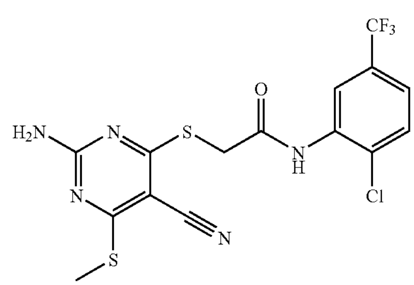 |

TABLE 3-continued

| Entry | Name | Structure |
|---|---|---|
| 58 | N²-[2-amino-5-[(E)-hydrazonomethyl]-6-(methylthio)pyrimidin-4-yl]-N-[3-(trifluoromethyl)phenyl]glycinamide | 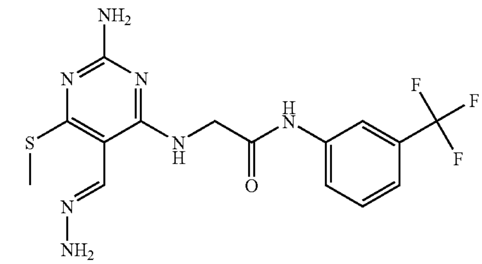 |
| 59 | N²-[2-amino-5-[(E)-(hydroxyimino)methyl]-6-(methylthio)pyrimidin-4-yl]-N-[3-(trifluoromethyl)phenyl]glycinamide | 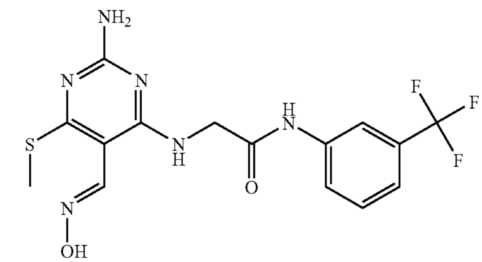 |
| 60 | N²-[2-amino-5-cyano-6-(methylthio)pyrimidin-4-yl]-N-[3-(trifluoromethyl)phenyl]-L-alaninamide | 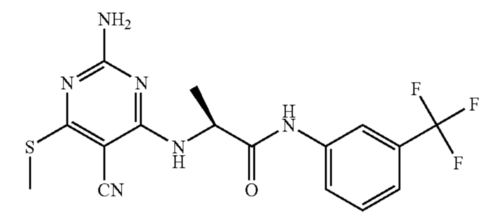 |
| 61 | 2-{[2-amino-5-cyano-6-(methylamino)pyrimidin-4-yl]thio}-N-[3-(trifluoromethyl)phenyl]acetamide | 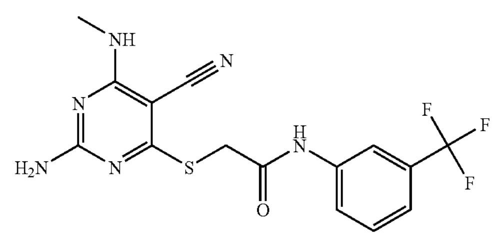 |
| 62 | 2-{[2-amino-5-cyano-6-(methylthio)pyrimidin-4-yl]thio}-N-[2-amino-5-(trifluoromethyl)phenyl]acetamide | 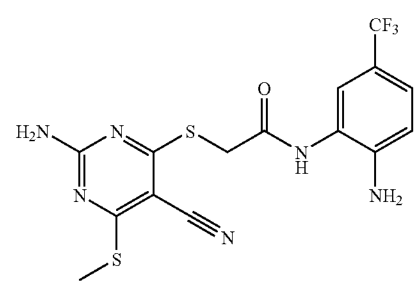 |
| 63 | 2-amino-4-(methylthio)-6-({[6-(trifluoromethyl)-1H-benzimidazol-2-yl]methyl}thio)pyrimidine-5-carbonitrile | 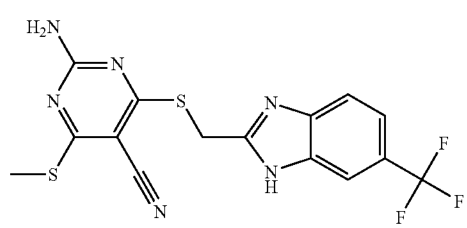 |

TABLE 3-continued

| Entry | Name | Structure |
|---|---|---|
| 64 | 2-[2-amino-5-cyano-6-(methylthio)pyrimidin-4-yl]-N-[3-(trifluoromethyl)phenyl]hydrazine-carboxamide | 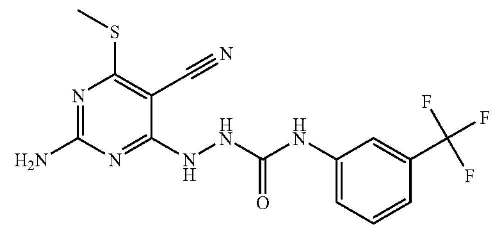 |
| 65 | N²-[5-cyano-2-(methylamino)-6-(methylthio)pyrimidin-4-yl]-N-[3-(trifluoromethyl)phenyl]glycinamide | 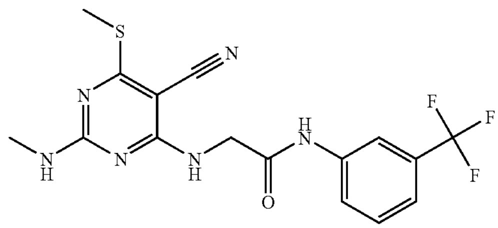 |
| 66 | 2-{[2-amino-5-cyano-6-(dimethylamino)pyrimidin-4-yl]thio}-N-[3-(trifluoromethyl)phenyl]acetamide | 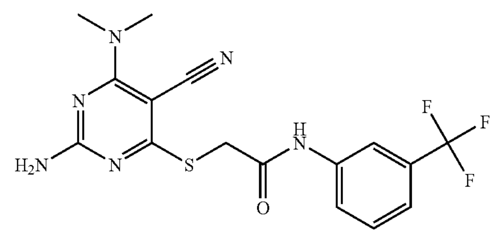 |
| 67 | (S)-1-[2-amino-5-cyano-6-(methylthio)pyrimidin-4-yl]-N-[3-(trifluoromethyl)phenyl]prolinamide | 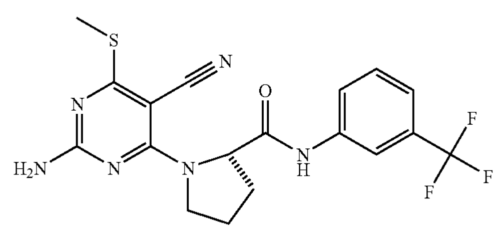 |
| 68 | (2R)-2-{[2-amino-5-cyano-6-(methylthio)pyrimidin-4-yl]oxy}-N-[3-(trifluoromethyl)phenyl]propanamide | 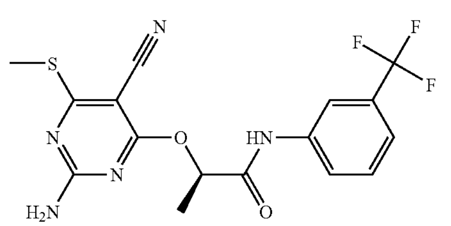 |
| 69 | 1-{[2-amino-5-cyano-6-(methylthio)pyrimidin-4-yl]oxy}-N-[3-(trifluoromethyl)phenyl]cyclopropanecarboxamide | 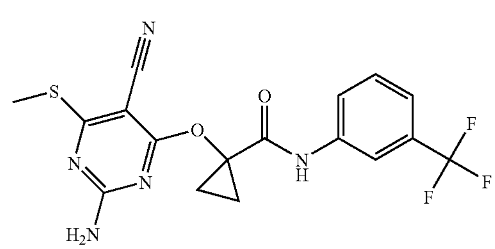 |

TABLE 3-continued

| Entry | Name | Structure |
|---|---|---|
| 70 | (2S)-2-{[2-amino-5-cyano-6-(methylthio)pyrimidin-4-yl]oxy}-3-methyl-N-[3-(trifluoromethyl)phenyl]butanamide | 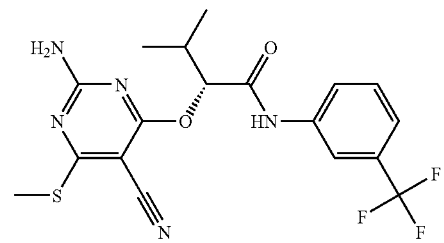 |
| 72 | $N^2$-[2-amino-5-cyano-6-(methylthio)pyrimidin-4-yl]-N-2-methyl-N-[3-(trifluoromethyl)phenyl]glycinamide | 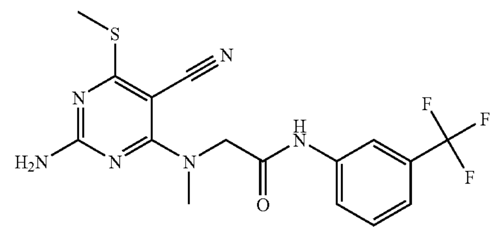 |
| 73 | 1-{[2-amino-5-cyano-6-(methylthio)pyrimidin-4-yl]amino}-N-[3-(trifluoromethyl)phenyl]cyclopropane carboxamide | 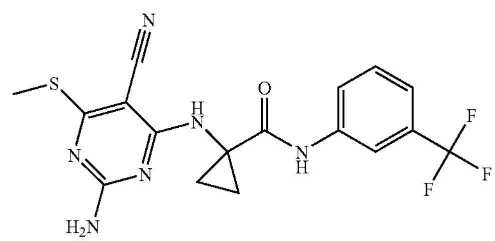 |
| 74 | $N^2$-[2-amino-5-cyano-6-(methylsulfinyl)pyrimidin-4-yl]-N-[3-(trifluoromethyl)phenyl]-L-alaninamide | 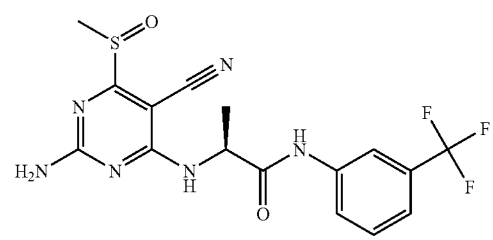 |
| 75 | $N^2$-[2-amino-5-cyano-6-(methylsulfonyl)pyrimidin-4-yl]-N-[3-(trifluoromethyl)phenyl]-L-alaninamide | 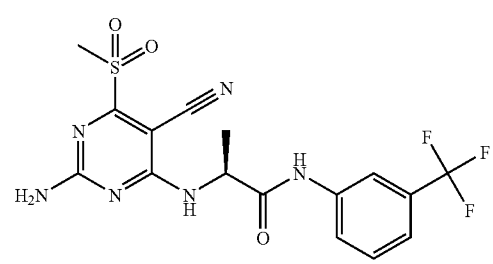 |
| 76 | $N^2$-(5-cyano-2-morpholin-4-ylpyrimidin-4-yl)-N-[3-(trifluoromethyl)phenyl]glycinamide | 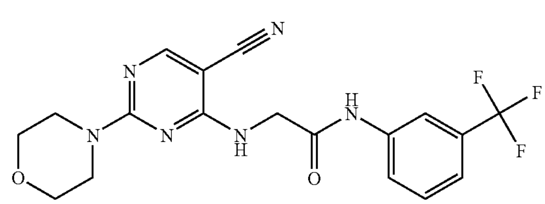 |

TABLE 3-continued

| Entry | Name |
|---|---|
| 78 | N²-[2-amino-5-cyano-6-(methyloxy)pyrimidin-4-yl]-N-[3-(trifluoromethyl)phenyl]-L-alaninamide |
| 79 | N²-[2-amino-5-cyano-6-(methylthio)pyrimidin-4-yl]-N-[2-(methyloxy)-5-(trifluoromethyl)phenyl]-L-alaninamide |
| 80 | N²-[2-amino-5-cyano-6-(methlylthio)pyrimidin-4-yl]-N-[2-chloro-5-(trifluoromethyl)phenyl]-L-alaninamide |
| 83 | N²-[2-amino-5-cyano-6-(methylthio)pyrimidin-4-yl]-N-[3-(trifluoromethyl)phenyl]-D-alaninamide |
| 84 | 2-[(2-amino-5-cyano-6-morpholin-4-ylpyrimidin-4-yl)thio]-N-[3-(trifluoromethyl)phenyl]acetamide |
| 85 | (R)-1-[2-amino-5-cyano-6-(methylthio)pyrimidin-4-yl]-N-[3-(trifluoromethyl)phenyl]prolinamide |

TABLE 3-continued

| Entry | Name | Structure |
|---|---|---|
| 86 | N²-[2-amino-5-cyano-6-(methylthio)pyrimidin-4-yl]-N-[3-(trifluoromethyl)phenyl]-L-ornithinamide | 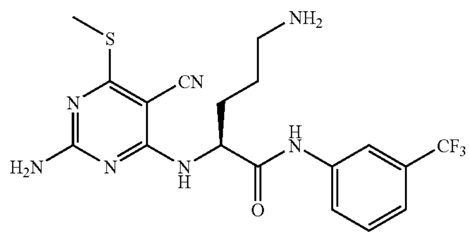 |
| 87 | N²-[2-amino-5-cyano-6-(methylthio)pyrimidin-4-yl]-N-2-[2-(dimethylamino)ethyl]-N-[3-(trifluoromethyl)phenyl]glycinamide | 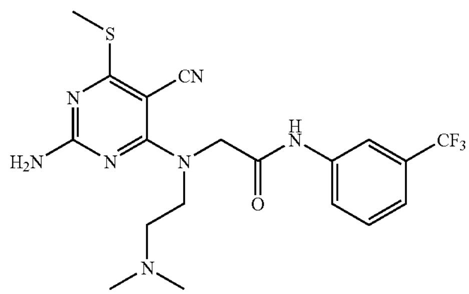 |
| 88 | N²-[2-amino-5-cyano-6-(ethyloxy)pyrimidin-4-yl]-N-[3-(trifluoromethyl)phenyl]-L-alaninamide | 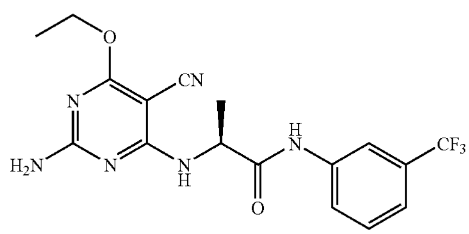 |
| 89 | N²-(2,6-diamino-5-cyanopyrimidin-4-yl)-N-[3-(trifluoromethyl)phenyl]-L-alaninamide | 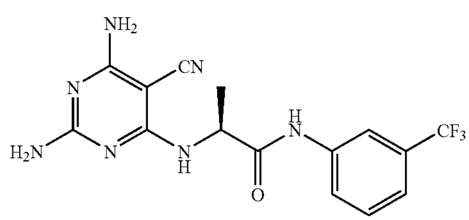 |
| 90 | N²-(2-amino-5-cyanopyrimidin-4-yl)-N-[3-(trifluoromethyl)phenyl]-L-alaninamide | 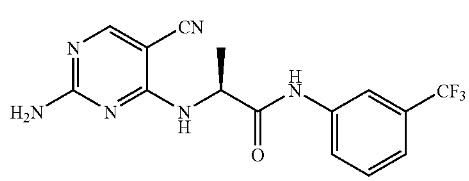 |
| 91 | N²-[2-amino-5-cyano-6-(methylthio)pyrimidin-4-yl]-N-2-methyl-N-[3-(trifluoromethyl)phenyl]-L-alaninamide | 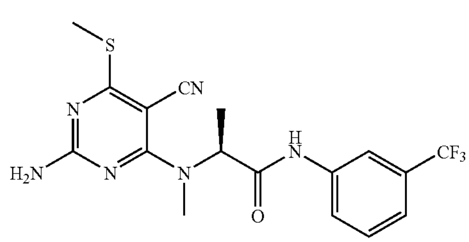 |

TABLE 3-continued

| Entry | Name |
|---|---|
| 93 | 2-[2-amino-5-cyano-6-(methylthio)pyrimidin-4-yl]-1,2-dimethyl-N-[3-(trifluoromethyl)phenyl]hydrazine-carboxamide |
| 94 | N²-[2-amino-5-cyano-6-(methylthio)pyrimidin-4-yl]-N-[3-amino-5-(trifluoromethyl)phenyl]-L-alaninamide |
| 95 | ethyl [1-[2-amino-5-cyano-6-(methylthio)pyrimidin-4-yl]-2-({[3-(trifluoromethyl)phenyl]amino}carbonyl)hydrazino]acetate |
| 96 | 2-[2-amino-5-cyano-6-(methylthio)pyrimidin-4-yl]-2-methyl-N-[3-(trifluoromethyl)phenyl]hydrazine-carboxamide |
| 100 | N²-[5-cyano-2-(methylthio)pyrimidin-4-yl]-N-[3-(trifluoromethyl)phenyl]glycinamide |
| 101 | N²-(2-amino-5-cyano-6-(methylthio)pyrimidin-4-yl]-N-2-(tetrahydro-2H-pyran-4-ylmethyl)-N-[3-(trifluoromethyl)phenyl]glycinamide |

TABLE 3-continued

| Entry | Name |
|---|---|
| 102 | N²-(2-amino-5-cyano-6-{[2-(dimethylamino)ethyl]oxy}pyrimidin-4-yl)-N-[3-(trifluoromethyl)phenyl]-L-alaninamide |
| 103 | N²-[2-amino-5-cyano-6-(methylthio)pyrimidin-4-yl]-N-6-{[(1,1-dimethylethyl)oxy]carbonyl}-N-[3-(trifluoromethyl)phenyl]-L-lysinamide |
| 104 | 2-amino-4-(methylthio)-6-(methyl{(1S)-1-[6-(trifluoromethyl)-1H-benzimidazol-2-yl]ethyl}amino)pyrimidine-5-carbonitrile |
| 105 | N²-[2-amino-5-cyano-6-(methylthio)pyrimidin-4-yl]-N-2-[2-(tetrahydro-2H-pyran-4-yl)ethyl]-N-[3-(trifluoromethyl)phenyl]glycinamide |
| 106 | N²-[2-amino-5-cyano-6-(methylthio)pyrimidin-4-yl]-N-[3-{[2-(diethylamino)ethyl]amino}-5-(trifluoromethyl)phenyl]-L-alaninamide |

TABLE 3-continued

| Entry | Name |
|---|---|
| 107 | 2-amino-4-(methylthio)-6-({(1S)-1-[6-(trifluoromethyl)-1H-benzimidazol-2-yl]ethyl}amino)pyrimidine-5-carbonitrile |
| 108 | 2-{2-amino-5-cyano-6-[1-(3-trifluoromethyl-phenylcarbamoyl)-1S-ethylamino]-pyrimidin-4-ylamino}-N-(3-trifluoromethyl-phenyl)-2S-propionamide |
| 109 | N²-[2-amino-5-cyano-6-(methylthio)pyrimidin-4-yl]-N-2-methyl-N-(3-methylphenyl)glycinamide |
| 110 | N²-[2-amino-5-cyano-6-(methylthio)pyrimidin-4-yl]-N-2-methyl-N-[3-(1-methylethyl)phenyl]glycinamide |
| 111 | N²-[2-amino-5-cyano-6-(methylthio)pyrimidin-4-yl]-N-5-[imino(nitroamino)methyl]-N-[3-(trifluoromethyl)phenyl]-L-ornithinamide |
| 112 | methyl 3-({N-[2-amino-5-cyano-6-(methylthio)pyrimidin-4-yl]-L-alanyl}amino)-5-(trifluoromethyl)benzoate |

TABLE 3-continued

| Entry | Name | Structure |
|---|---|---|
| 113 | N²-[2-amino-5-cyano-6-(methylthio)pyrimidin-4-yl]-N-(3-nitrophenyl)-L-alaninamide | 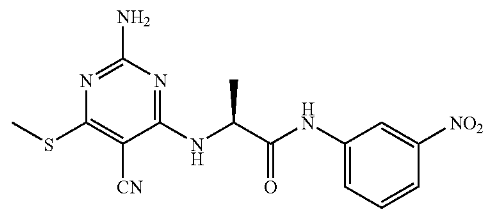 |
| 114 | N²-[2-amino-5-cyano-6-(methylthio)pyrimidin-4-yl]-N-]3-(trifluoromethyl)phenyl]-L-lysinamide | 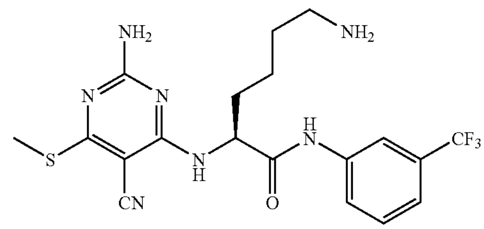 |
| 115 | N²-[2-amino-5-cyano-6-(propyloxy)pyrimidin-4-yl]-N-[3-(trifluoromethyl)phenyl]-L-alaninamide | 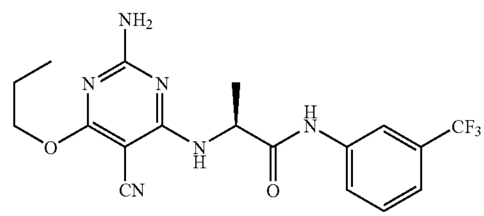 |
| 117 | N²-[2-amino-5-cyano-6-(methylthio)pyrimidin-4-yl]-N-[3-(trifluoromethyl)phenyl]-L-argininamide | 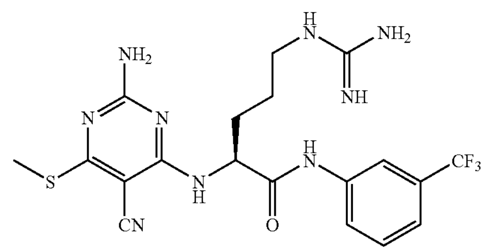 |
| 118 | N²-[2-amino-5-cyano-6-(methylsulfinyl)pyrimidin-4-yl]-N-2-methyl-N-[3-(trifluoromethyl)phenyl]-L-alaninamide | 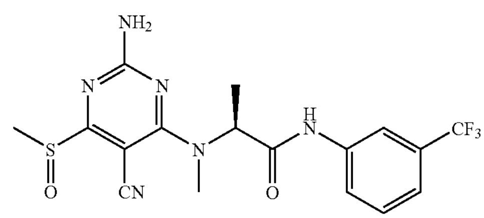 |
| 119 | N²-[2-amino-5-cyano-6-(methyloxy)pyrimidin-4-yl]-N-2-methyl-N-[3-(trifluoromethyl)phenyl]-L-alaninamide | 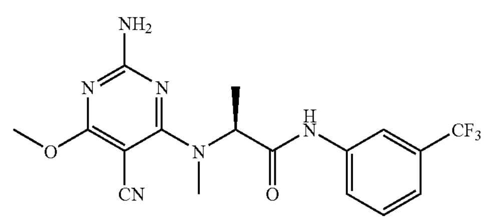 |
| 120 | N²-[2-amino-5-cyano-6-(propyloxy)pyrimidin-4-yl]-N-2-methyl-N-[3-(trifluoromethyl)phenyl]-L-alaninamide | 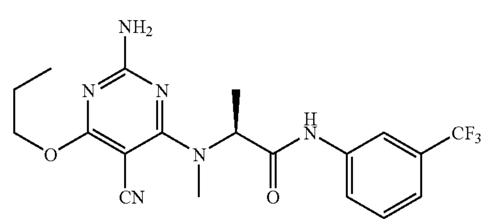 |

TABLE 3-continued

| Entry | Name | Structure |
|---|---|---|
| 121 | N²-[2-amino-5-cyano-6-(ethyloxy)pyrimidin-4-yl]-N-2-methyl-N-[3-(trifluoromethyl)phenyl]-L-alaninamide | 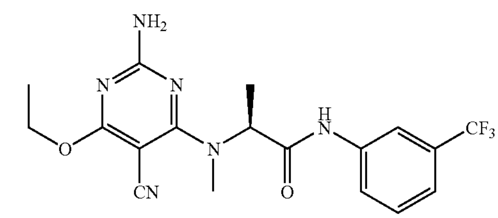 |
| 122 | N²-[2-amino-5-cyano-6-[(1-methylethyl)oxy]pyrimidin-4-yl}-N-[3-(trifluoromethyl)phenyl]-L-alaninamide | 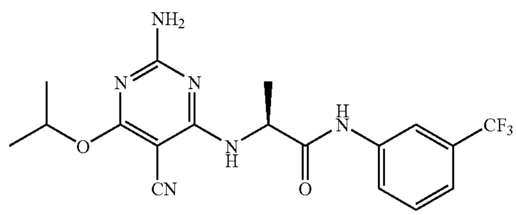 |
| 123 | N-5-acetyl-N-2-[2-amino-5-cyano-6-(methylthio)pyrimidin-4-yl]-N-[3-(trifluoromethyl)phenyl]-L-ornithinamide | 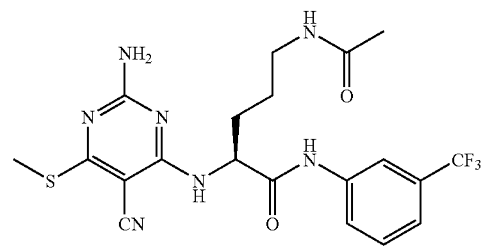 |
| 124 | N²-[2-amino-5-cyano-6-(methylthio)pyrimidin-4-yl]-N-(3-aminophenyl)-L-alaninamide | 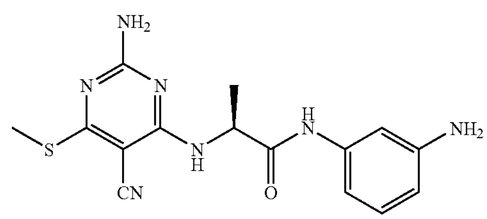 |
| 125 | 3-({N-[2-amino-5-cyano-6-(methylthio)pyrimidin-4-yl]-L-alanyl}amino)-N-[2-(dimethylamino)ethyl]-5-(trifluoromethyl)benzamide | 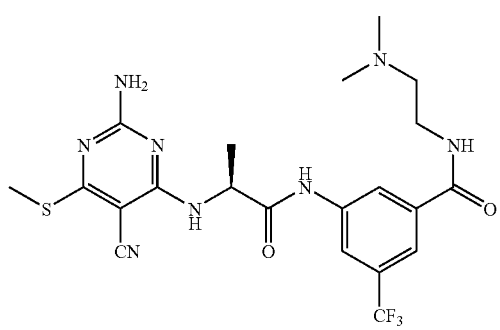 |
| 126 | 2-(methyloxy)ethyl ((4S)-4-{[2-amino-5-cyano-6-(methylthio)pyrimidin-4-yl]amino)-5-oxo-5-{[3-(trifluoromethyl)phenyl]amino}pentyl) carbamate | 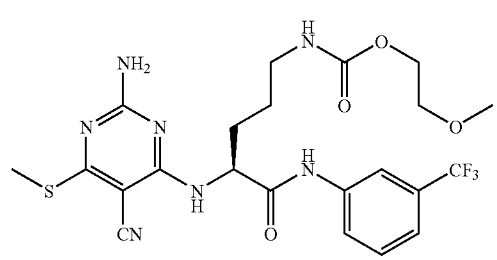 |

TABLE 3-continued

| Entry | Name | Structure |
|-------|------|-----------|
| 127 | 2-[2-amino-5-cyano-6-(ethyloxy)pyrimidin-4-yl]-N-[3-(trifluoromethyl)phenyl]hydrazinecarboxamide | 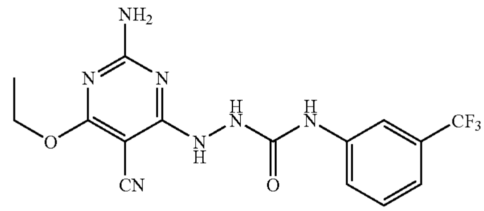 |
| 128 | 1,1-dimethylethyl ((4S)-4-{[2-amino-5-cyano-6-(ethyloxy)pyrimidin-4-yl]amino}-5-oxo-5-{[3-(trifluoromethyl)phenyl]amino}pentyl)carbamate | 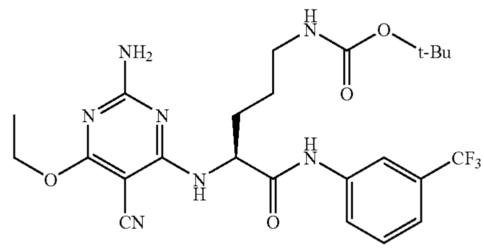 |
| 130 | 3-({N-[2-amino-5-cyano-6-(methylthio)pyrimidin-4-yl]-N-methyl-L-alanyl}amino)-N-[2-(dimethylamino)ethyl]-5-(trifluoromethyl)benzamide | Chiral |
| 131 | 3-({N-[2-amino-5-cyano-6-(methylthio)pyrimidin-4-yl]-N-methyl-L-alanyl}amino)-N-[3-(4-methylpiperazin-1-yl)propyl]-5-(trifluoromethyl)benzamide | Chiral |

TABLE 3-continued

| Entry | Name | Structure |
|---|---|---|
| 132 | N²-[2-amino-5-cyano-6-(methylthio)pyrimidin-4-yl]-N~2~-methyl-N-{3-](trifluoromethyl)oxy]phenyl}-L-alaninamide | Chiral |
| 133 | N²-[2-amino-5-cyano-6-(methylthio)pyrimidin-4-yl]-N-(3-bromophenyl)-N~2~-methyl-L-alaninamide | Chiral |
| 134 | N²-[2-amino-5-cyano-6-(methylthio)pyrimidin-4-yl]-N-{2-{[2-(dimethylamino)ethyl]oxy}-5-[(trifluoromethyl)oxy]phenyl}-N~2~-methyl-L-alaninamide | Chiral |
| 135 | 3-({N-[2-amino-5-cyano-6-(methylthio)pyrimidin-4-yl]-N-methyl-L-alanyl}amino)-N-(2-morpholin-4-ylethyl)-5-(trifluoromethyl)benzamide | Chiral |

TABLE 3-continued

| Entry | Name | Structure |
|---|---|---|
| 136 | $N^2$-[2-amino-5-cyano-6-(ethyloxy)pyrimidin-4-yl]-N~2~-methyl-N-[3-(trifluoromethyl)phenyl]-L-lysinamide | Chiral |
| 137 | $N^2$-[2-amino-5-cyano-6-(methylthio)pyrimidin-4-yl]-N-[3-{[2-(dimethylamino)ethyl]oxy}-5-(trifluoromethyl)phenyl]-L-alaninamide | Chiral |
| 138 | (2S)-2-{[2-amino-5-cyano-6-(methylthio)pyrimidin-4-yl]amino}-3-oxo-3-{[3-(trifluoromethyl)phenyl]amino}propyl acetate | Chiral |
| 139 | $N^2$-[2-amino-5-cyano-6-(methylthio)pyrimidin-4-yl]-N~1~-[3-(trifluoromethyl)phenyl]-L-glutamamide | Chiral |
| 140 | 2-[2-amino-5-cyano-6-(methyloxy)pyrimidin-4-yl]-N-[3-(trifluoromethyl)phenyl]hydrazinecarboxamide | 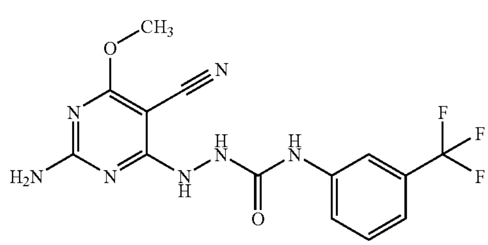 |

TABLE 3-continued

| Entry | Name | Structure |
|---|---|---|
| 141 | 3-({N-[2-amino-5-cyano-6-(methylthio)pyrimidin-4-yl]-L-alanyl}amino)-N-hydroxy-5-(trifluoromethyl)benzamide | Chiral |
| 142 | N²-[2-amino-5-cyano-6-(methylthio)pyrimidin-4-yl]-3-(dimethylamino)-N-[3-(trifluoromethyl)phenyl]-L-alaninamide | Chiral |
| 143 | N²-[2-amino-5-cyano-6-(methylthio)pyrimidin-4-yl]-5-morpholin-4-yl-N-[3-(trifluoromethyl)phenyl]-L-norvalinamide | Chiral |
| 144 | N²-[2-amino-5-cyano-6-(methylthio)pyrimidin-4-yl]-N~5~-[2-(methyloxy)ethyl]-N-[3-(trifluoromethyl)phenyl]-L-ornithinamide | Chiral |
| 145 | 3-({N-[2-amino-5-cyano-6-(methylthio)pyrimidin-4-yl]-L-alanyl}amino)-5-(trifluoromethyl)benzoic acid | Chiral |

TABLE 3-continued

| Entry | Name | Structure |
|---|---|---|
| 146 | methyl N~2~-[2-amino-5-cyano-6-(methylthio)pyrimidin-4-yl]-N-[3-(trifluoromethyl)phenyl]-L-alpha-glutaminate | Chiral |
| 147 | N5-(aminocarbonyl)-N~2~-[2-amino-5-cyano-6-(methylthio)pyrimidin-4-yl]-N-[3-(trifluoromethyl)phenyl]-L-ornithinamide | Chiral |
| 148 | N2-[2-amino-5-cyano-6-(ethyloxy)pyrimidin-4-yl]-N-[3-(trifluoromethyl)phenyl]-L-ornithinamide | Chiral |
| 149 | N2-[2-amino-5-cyano-6-(methylthio)pyrimidin-4-yl]-N-[3-(trifluoromethyl)phenyl]-L-alpha-glutamine | Chiral |
| 150 | N2-[2-amino-5-cyano-6-(ethyloxy)pyrimidin-4-yl]-N-[3-(trifluoromethyl)phenyl]-L-serinamide | Chiral |

TABLE 3-continued

| Entry | Name | Structure |
|---|---|---|
| 151 | N²-[2-amino-5-cyano-6-(ethyloxy)pyrimidin-4-yl]-O-(phenylmethyl)-N-[3-(trifluoromethyl)phenyl]-L-serinamide | Chiral |
| 152 | N²-[2-amino-5-cyano-6-(ethyloxy)pyrimidin-4-yl]-N-[3-(trifluoromethyl)phenyl]-L-argininamide | Chiral |
| 153 | N²-[2-amino-5-cyano-6-(methylthio)pyrimidin-4-yl]-N~2~-methyl-N~6~-{[(phenylmethyl)oxy]carbonyl}-N-[3-(trifluoromethyl)phenyl]-L-lysinamide | Chiral |
| 154 | N-α-[2-amino-5-cyano-6-(ethyloxy)pyrimidin-4-yl]-N-[3-(trifluoromethyl)phenyl]-L-tyrosinamide | Chiral |

TABLE 3-continued

| Entry | Name | Structure |
|---|---|---|
| 155 | N⁵-[2-amino-5-cyano-6-(methylthio)pyrimidin-4-yl]-N-[3-(trifluoromethyl)phenyl]-L-ornithinamide | 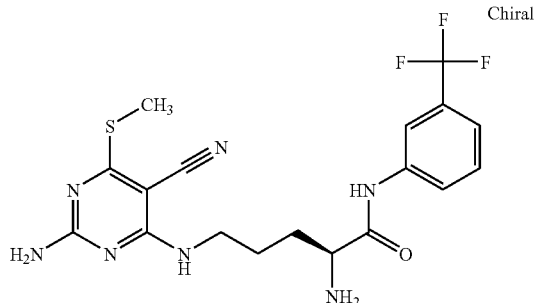 Chiral |
| 156 | N²-[2-amino-5-cyano-6-(ethyloxy)pyrimidin-4-yl]-N~6~,N~6~-dimethyl-N-[3-(trifluoromethyl)phenyl]-L-lysinamide | 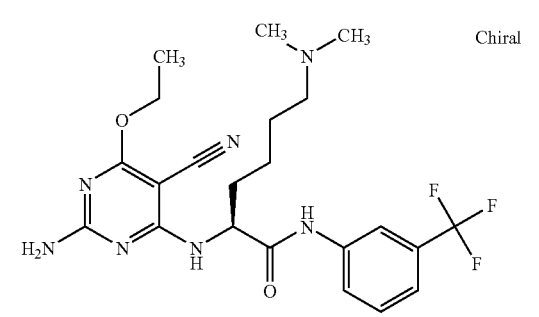 Chiral |
| 157 | N²-[2-amino-5-cyano-6-(ethyloxy)pyrimidin-4-yl]-N-[3-[(4-methylpiperazin-1-yl)carbonyl]-5-(trifluoromethyl)phenyl]-L-alaninamide | 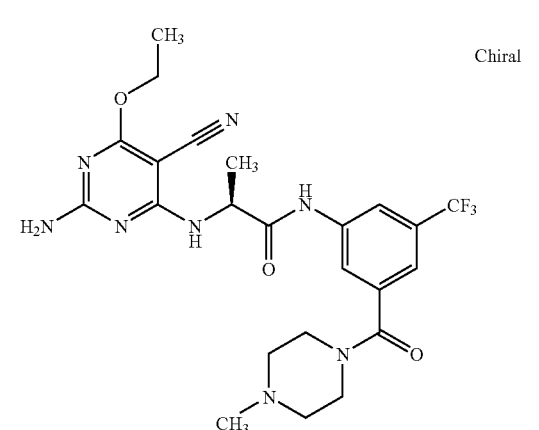 Chiral |
| 158 | 3-({N-[2-amino-5-cyano-6-(ethyloxy)pyrimidin-4-yl]-L-alanyl}amino)-N-(3-pyrrolidin-1-ylpropyl)-5-(trifluoromethyl)benzamide | 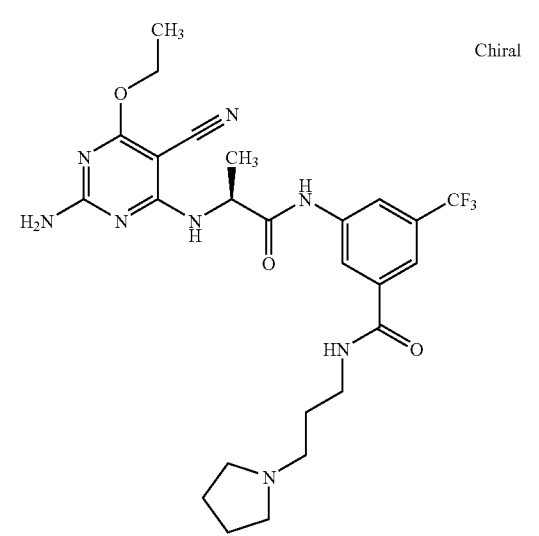 Chiral |

TABLE 3-continued

| Entry | Name | Structure |
|---|---|---|
| 159 | 3-({N-[2-amino-5-cyano-6-(ethyloxy)pyrimidin-4-yl]-L-alanyl}amino)-N-(2-morpholin-4-ylethyl)-5-(trifluoromethyl)benzamide | Chiral |
| 160 | 3-({N-[2-amino-5-cyano-6-(ethyloxy)pyrimidin-4-yl]-L-alanyl}amino)-N-[2-(dimethylamino)ethyl]-5-(trifluoromethyl)benzamide | Chiral |
| 161 | 3-({N-[2-amino-5-cyano-6-(ethyloxy)pyrimidin-4-yl]-L-alanyl}amino)-N-[3-(4-methylpiperazin-1-yl)propyl]-5-(trifluoromethyl)benzamide | Chiral |

TABLE 3-continued

| Entry | Name | Structure |
|---|---|---|
| 162 | N²-[2-amino-5-cyano-6-(ethyloxy)pyrimidin-4-yl]-N~2~-methyl-N⁶-{[(phenylmethyl)oxy]carbonyl}-N-[3-(trifluoromethyl)phenyl]-L-lysinamide | Chiral |
| 163 | 1,1-dimethylethyl ((4S)-4-{[2-amino-5-cyano-6-(ethyloxy)pyrimidin-4-yl]amino}-5-oxo-5-{[3-(trifluoromethyl)phenyl]amino}pentyl)carbamate | Chiral |
| 164 | (2S)-2-{[2-amino-5-cyano-6-(ethyloxy)pyrimidin-4-yl]amino}-3-oxo-3-{[3-(trifluoromethyl)phenyl]amino}propyl acetate | Chiral |
| 165 | phenylmethyl N~2~-[2-amino-5-cyano-6-(ethyloxy)pyrimidin-4-yl]-N-[3-(trifluoromethyl)phenyl]-L-alpha-glutaminate | Chiral |

TABLE 3-continued

| Entry | Name |
|---|---|
| 166 | N²,N⁵-diacetyl-N~2~-[2-(acetylamino)-5-cyano-6-(methylthio)pyrimidin-4-yl]-N-[3-(trifluoromethyl)phenyl]-L-ornithinamide |
| 167 | 2-(methyloxy)ethyl ((4S)-4-{[2-amino-5-cyano-6-(methylthio)pyrimidin-4-yl]amino}-5-oxo-5-{[(3-(trifluoromethyl)phenyl]amino}pentyl)carbamate |
| 168 | N~2~-[2-amino-5-cyano-6-(ethyloxy)pyrimidin-4-yl]-5-morpholin-4-yl-N-[3-(trifluoromethyl)phenyl]-L-norvalinamide |
| 169 | N-((4S)-4-{[2-amino-5-cyano-6-(ethyloxy)pyrimidin-4-yl]amino}-5-oxo-5-{[3-(trifluoromethyl)phenyl]amino}pentyl)-N,N-dimethylmethanaminium |
| 170 | Methyl N²-[2-amino-5-cyano-6-(ethyloxy)pyrimidin-4-yl]-N-[3-(trifluoromethyl)phenyl]-L-alpha-glutaminate |

TABLE 3-continued

| Entry | Name | Structure |
|---|---|---|
| 171 | N²-[2-amino-5-cyano-6-(methylthio)pyrimidin-4-yl]-N~6~,N~6~-dimethyl-N-[3-(trifluoromethyl)phenyl]-L-lysinamide | Chiral |
| 172 | N²-[2-amino-5-cyano-6-(ethyloxy)pyrimidin-4-yl]-N~2~-methyl-N-{3-[(trifluoromethyl)oxy]phenyl}-L-alaninamide | Chiral |
| 173 | N²-[2-amino-5-cyano-6-(ethyloxy)pyrimidin-4-yl]-N-[3-(trifluoromethyl)phenyl]-L-alpha-glutamine | Chiral |
| 174 | N~2~-[2-amino-5-cyano-6-(ethyloxy)pyrimidin-4-yl]-N-(3-bromophenyl)-N~2~-methyl-L-alaninamide | Chiral |
| 175 | N²-[2-amino-5-cyano-6-(ethyloxy)pyrimidin-4-yl]-N¹-[3-(trifluoromethyl)phenyl]-L-glutamamide | Chiral |

TABLE 3-continued

| Entry | Name | Structure | |
|---|---|---|---|
| 176 | N²-[2-amino-5-cyano-6-(ethyloxy)pyrimidin-4-yl]-3-(dimethylamino)-N-[3-(trifluoromethyl)phenyl]-L-alaninamide | 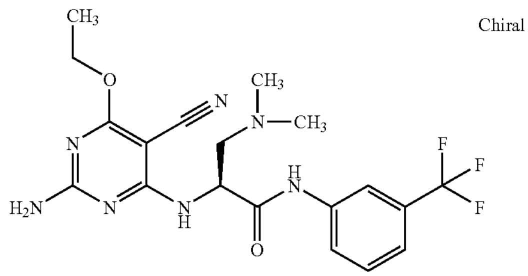 | Chiral |
| 177 | Structure possibly contains amino acid derivative which is not supported in current version! | 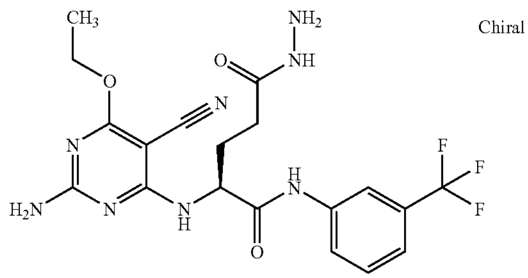 | Chiral |
| 178 | N²-[2-amino-5-cyano-6-(methyloxy)pyrimidin-4-yl]-3-(dimethylamino)-N-[3-(trifluoromethyl)phenyl]-L-alaninamide | 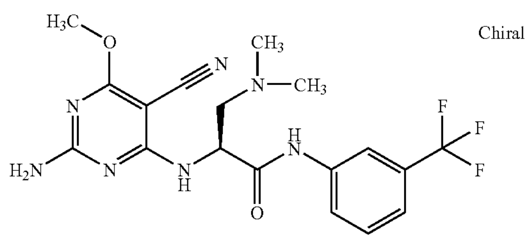 | Chiral |
| 179 | N²-[2-amino-5-cyano-6-(methyloxy)pyrimidin-4-yl]-N-(3-{(2-(dimethylamino)ethyl]oxy}-5-(trifluoromethyl)phenyl]-L-alaninamide | 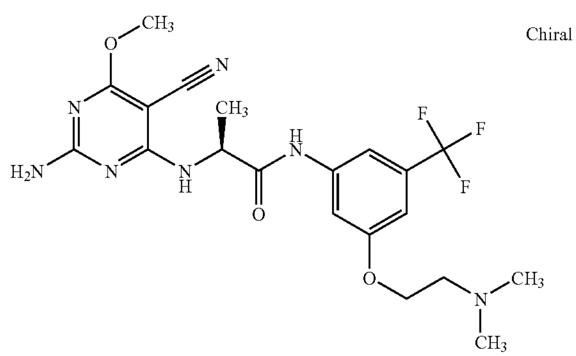 | Chiral |
| 180 | N²-[2-amino-5-cyano-6-(ethyloxy)pyrimidin-4-yl]-N-[3-{[2-(dimethylamino)ethyl]oxy}-5-(trifluoromethyl)phenyl]-L-alaninamide | 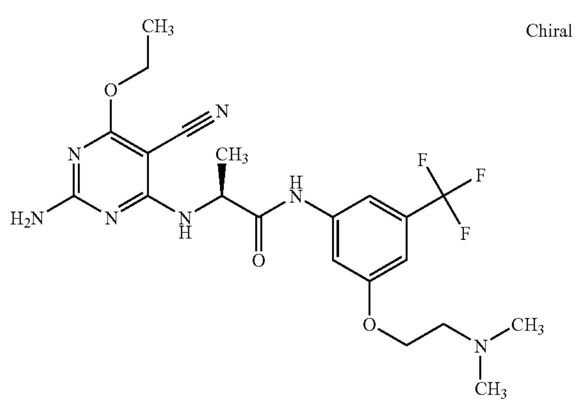 | Chiral |

TABLE 3-continued

| Entry | Name | Structure |
|---|---|---|
| 181 | N²-[2-amino-5-cyano-6-(methyloxy)pyrimidin-4-yl]-N-(3-bromophenyl)-N²-methyl-L-alaninamide | Chiral |
| 182 | phenylmethyl N~2~-[2-amino-5-cyano-6-(methylthio)pyrimidin-4-yl]-N-[3-(trifluoromethyl)phenyl]-L-alpha-glutaminate | Chiral |
| 183 | N²-[2-amino-5-cyano-6-(methylthio)pyrimidin-4-yl]-O-(phenylmethyl)-N-[3-(trifluoromethyl)phenyl]-L-serinamide | Chiral |
| 184 | N²-[2-amino-5-cyano-6-(methylthio)pyrimidin-4-yl]-N~5~,N~5~-bis[2-(methyloxy)ethyl]-N-[3-(trifluoromethyl)phenyl]-L-ornithinamide | Chiral |
| 185 | 1,1-dimethylethyl ((4S)-4-{[2-amino-5-cyano-6-(methyloxy)pyrimidin-4-yl]amino}-5-oxo-5-{[3-(trifluoromethyl)phenyl]amino}pentyl)carbamate | Chiral |

TABLE 3-continued

| Entry | Name | Structure |
|---|---|---|
| 186 | $N^5$-acetyl-$N^2$-[2-amino-5-cyano-6-(ethyloxy)pyrimidin-4-yl]-N-(3-(trifluoromethyl)phenyl]-L-ornithinamide | Chiral |
| 187 | $N^5$-acetyl-$N^2$-[2-amino-5-cyano-6-(methylthio)pyrimidin-4-yl]-N-[3-(trifluoromethyl)phenyl]-L-ornithinamide | Chiral |
| 188 | $N^2$-[2-amino-5-cyano-6-(methyloxy)pyrimidin-4-yl]-$N^2$-methyl-N-{3-[(trifluoromethyl)oxy]phenyl}-L-alaninamide | 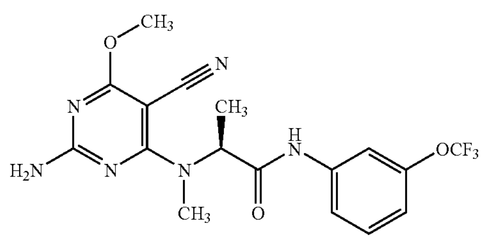 |
| 189 | methyl 3-({N-[2-amino-5-cyano-6-(methyloxy)pyrimidin-4-yl]-L-alanyl}amino)-5-(trifluoromethyl)benzoate | 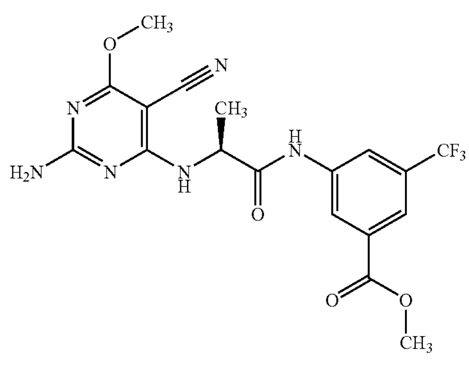 |

TABLE 3-continued

| Entry | Name | Structure |
|---|---|---|
| 190 | 3-({N-[2-amino-5-cyano-6-(methyloxy)pyrimidin-4-yl]-L-alanyl}amino)-N-[2-(dimethylamino)ethyl]-5-(trifluoromethyl)benzamide | Chiral |
| 191 | $N^2$-{2-amino-5-cyano-6-(methylthio)pyrimidin-4-yl]-3-morpholin-4-yl-N-[3-(trifluoromethyl)phenyl]-L-alaninamide | Chiral |
| 192 | $N^2$-[2-amino-5-cyano-6-(methyloxy)pyrimidin-4-yl]-3-morpholin-4-yl-N-[3-(trifluoromethyl)phenyl]-L-alaninamide | Chiral |
| 193 | $N^2$-[2-amino-5-cyano-6-(ethyloxy)pyrimidin-4-yl]-3-morpholin-4-yl-N-[3-(trifluoromethyl)phenyl]-L-alaninamide | Chiral |
| 194 | $N^5$-(aminocarbonyl)-$N^2$-[2-amino-5-cyano-6-(ethyloxy)pyrimidin-4-yl]-N-[3-(trifluoromethyl)phenyl]-L-ornithinamide | Chiral |

TABLE 3-continued

| Entry | Name | Structure | |
|---|---|---|---|
| 195 | N~2~-[2-amino-5-cyano-6-(methylthio)pyrimidin-4-yl]-N-[3-(trifluoromethyl)phenyl]-D-lysinamide | 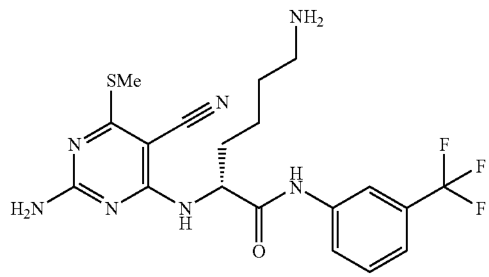 | Chiral |
| 196 | N²-[2-amino-5-cyano-6-(ethyloxy)pyrimidin-4-yl]-N-[3-(trifluoromethyl)phenyl]-D-lysinamide | 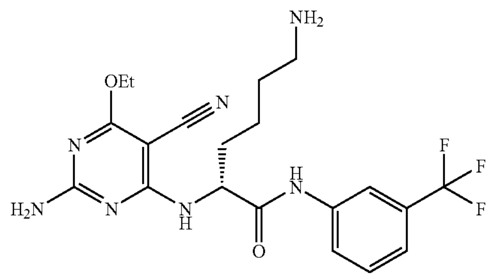 | Chiral |
| 197 | N²-[2-amino-5-cyano-6-(ethyloxy)pyrimidin-4-yl]-O-methyl-N-[3-(trifluoromethyl)phenyl]-L-serinamide | 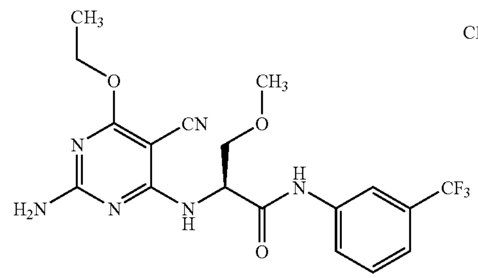 | Chiral |
| 198 | N²-[2-amino-5-cyano-6-(methylthio)pyrimidin-4-yl]-N~5~-(methylsulfonyl)-N-[3-(trifluoromethyl)phenyl]-L-ornithinamide | 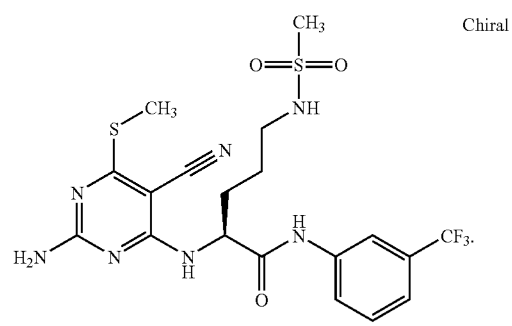 | Chiral |

11. A pharmaceutical composition comprising the compound according to claim 1 and a pharmaceutically acceptable carrier.

* * * * *